(12) United States Patent
Ingman et al.

(10) Patent No.: US 11,110,272 B2
(45) Date of Patent: Sep. 7, 2021

(54) APPARATUS FOR STIMULATING HAIR GROWTH AND/OR PREVENTING HAIR LOSS

(71) Applicant: PILOGICS L.P., Haifa (IL)

(72) Inventors: Dov Ingman, Haifa (IL); Erez Manor, Herzlia (IL)

(73) Assignee: PILOGICS L.P., Haifa (IL)

( * ) Notice: Subject to any disclaimer, the term of this patent is extended or adjusted under 35 U.S.C. 154(b) by 163 days.

(21) Appl. No.: 15/944,168

(22) Filed: Apr. 3, 2018

(65) Prior Publication Data

US 2018/0326208 A1   Nov. 15, 2018

Related U.S. Application Data

(63) Continuation-in-part of application No. 14/739,832, filed on Jun. 15, 2015, now abandoned, and a
(Continued)

(51) Int. Cl.
| | |
|---|---|
| *A61N 1/32* | (2006.01) |
| *A61N 1/05* | (2006.01) |

(Continued)

(52) U.S. Cl.
CPC ........... *A61N 1/325* (2013.01); *A61N 1/0502* (2013.01); *A61N 1/36017* (2013.01);
(Continued)

(58) Field of Classification Search
CPC .............. A61H 15/0092; A61H 15/02; A61M 37/0015; A61M 2037/0023;
(Continued)

(56) References Cited

U.S. PATENT DOCUMENTS

| | | | |
|---|---|---|---|
| 5,961,483 A | 10/1999 | Sage et al. | |
| 5,964,729 A | * 10/1999 | Choi | .................... A61B 17/205 |
| | | | 604/47 |

(Continued)

FOREIGN PATENT DOCUMENTS

| | | |
|---|---|---|
| CN | 2901984 Y | 5/2007 |
| CN | 2019996809 | 2/2016 |

(Continued)

*Primary Examiner* — Bhisma Mehta
*Assistant Examiner* — James D Ponton
(74) *Attorney, Agent, or Firm* — Marc Van Dyke; Momentum IP

(57) ABSTRACT

A device to stimulate a scalp comprises an array of stimulating elements, the stimulating elements arranged along a circumference of at least one wheel, the wheel adapted to roll over the scalp. A method of treating/preventing a hair-condition comprises: subjecting the scalp to at least 200 distinct electrode-scalp contact events during a time-interval of at most one minute and dividable into 5 non-overlapping equal-duration sub-intervals covering the time-interval, method performed such that i. for at least a majority of the electrode-scalp contact events, no electrode of the event enters into the dermis; ii. a duration of each electrode contact event is at most 100 milliseconds; and iii. for each electrode contact event, an electrical current flows between the electrode and the scalp so as to deposit electrode-released ions of a first metal or of a second metal on the scalp, thereby forming a respective metal-ion-deposition island on the user's scalp.

14 Claims, 54 Drawing Sheets

Related U.S. Application Data continuation-in-part of application No. 14/361,742, filed as application No. PCT/IB2012/057041 on Dec. 6, 2012, now abandoned.

(60) Provisional application No. 62/011,705, filed on Jun. 13, 2014, provisional application No. 61/568,202, filed on Dec. 8, 2011.

(51) Int. Cl.
 *A61N 1/36* (2006.01)
 *A61M 37/00* (2006.01)

(52) U.S. Cl.
 CPC . *A61M 37/0092* (2013.01); *A61M 2037/0007* (2013.01); *A61M 2205/3317* (2013.01); *A61N 1/0526* (2013.01); *A61N 1/322* (2013.01); *A61N 1/326* (2013.01)

(58) Field of Classification Search
 CPC ........... A61M 2037/003; A61N 1/0476; A61N 1/0502; A61N 1/26; A61N 1/306; A61N 1/322; A61N 1/325; A61N 1/326; A61N 1/327; A61N 1/328; A61Q 7/00
 See application file for complete search history.

(56) References Cited

U.S. PATENT DOCUMENTS

| | | | |
|---|---|---|---|
| 5,975,090 A | 11/1999 | Taylor et al. | |
| 6,678,554 B1* | 1/2004 | Sun | A61N 1/044 604/20 |
| 6,834,206 B1 | 12/2004 | Pitzen et al. | |
| D500,854 S | 1/2005 | Eichel | |
| 7,194,316 B2 | 3/2007 | Bousfield et al. | |
| 7,238,375 B1* | 7/2007 | Perry | A61K 36/16 424/522 |
| D568,473 S | 5/2008 | Ashiwa et al. | |
| 7,597,692 B2 | 10/2009 | Weaver et al. | |
| D645,204 S | 9/2011 | Platek | |
| 8,048,019 B2 | 11/2011 | Nisato et al. | |
| D664,295 S | 7/2012 | Grabes et al. | |
| D665,128 S | 8/2012 | Kling et al. | |
| D678,614 S | 3/2013 | Mu | |
| D678,783 S | 3/2013 | Wilcox et al. | |
| D686,370 S | 7/2013 | Mu | |
| D696,778 S | 12/2013 | Liao et al. | |
| D719,651 S | 12/2014 | Hoffmann et al. | |
| D724,726 S | 3/2015 | Prokop | |
| 9,566,431 B2 | 2/2017 | Ingman et al. | |
| D787,055 S | 5/2017 | Ingman et al. | |
| 2002/0010414 A1* | 1/2002 | Coston | A61B 5/14514 604/20 |
| 2004/0006374 A1 | 1/2004 | Mondin | |
| 2004/0147984 A1 | 7/2004 | Altshuler et al. | |
| 2004/0267169 A1 | 12/2004 | Sun et al. | |
| 2005/0004509 A1 | 1/2005 | Sun et al. | |
| 2005/0004550 A1 | 1/2005 | Sun et al. | |
| 2005/0010161 A1 | 1/2005 | Sun et al. | |
| 2005/0010192 A1 | 1/2005 | Sun et al. | |
| 2006/0084894 A1 | 4/2006 | Anderson | |
| 2006/0253079 A1 | 11/2006 | McDonough et al. | |
| 2007/0038275 A1* | 2/2007 | Kim | A61N 1/326 607/90 |
| 2007/0049901 A1 | 3/2007 | Wu et al. | |
| 2007/0060862 A1 | 3/2007 | Sun et al. | |
| 2007/0073217 A1* | 3/2007 | James | A61B 17/205 604/46 |
| 2007/0078376 A1* | 4/2007 | Smith | A61M 37/0015 604/21 |
| 2008/0058783 A1 | 3/2008 | Altshuler et al. | |
| 2008/0161746 A1 | 7/2008 | Visco et al. | |
| 2008/0221504 A1* | 9/2008 | Aghion | A61H 7/008 604/20 |
| 2009/0005801 A1* | 1/2009 | Eastman | A61B 17/205 606/186 |
| 2009/0069740 A1 | 3/2009 | Visco et al. | |
| 2009/0118698 A1 | 5/2009 | Liebl | |
| 2009/0254076 A1 | 10/2009 | Altshuler et al. | |
| 2009/0312691 A1* | 12/2009 | Kim | A61H 15/0092 604/22 |
| 2010/0036295 A1 | 2/2010 | Altshuler et al. | |
| 2010/0262081 A1 | 10/2010 | Lee et al. | |
| 2010/0272827 A1* | 10/2010 | Imran | A61K 9/0009 424/604 |
| 2010/0286673 A1 | 11/2010 | Altshuler et al. | |
| 2011/0009782 A1 | 1/2011 | Pampalone et al. | |
| 2011/0040236 A1 | 2/2011 | Isaacs et al. | |
| 2011/0118655 A1* | 5/2011 | Fassih | A61N 1/205 604/20 |
| 2011/0172574 A1* | 7/2011 | Han | A61H 15/0092 601/119 |
| 2011/0172745 A1 | 7/2011 | Na et al. | |
| 2011/0218464 A1 | 9/2011 | Iger | |
| 2012/0184894 A1 | 7/2012 | Imran et al. | |
| 2013/0013028 A1 | 1/2013 | Kriksunov et al. | |
| 2014/0005644 A1 | 1/2014 | Karni et al. | |
| 2014/0005658 A1 | 1/2014 | Rosenbegr | |
| 2014/0025062 A1 | 1/2014 | Rosenberg et al. | |
| 2014/0121730 A1 | 5/2014 | Kalev et al. | |
| 2014/0214022 A1 | 7/2014 | Adanny et al. | |
| 2014/0228834 A1 | 8/2014 | Adanny et al. | |
| 2014/0249522 A1 | 9/2014 | Adanny et al. | |
| 2014/0276370 A1 | 9/2014 | Iger | |
| 2014/0296852 A1 | 10/2014 | Adanny et al. | |
| 2014/0303546 A1 | 10/2014 | Badiavas et al. | |
| 2014/0324035 A1 | 10/2014 | Iger et al. | |
| 2014/0330196 A1 | 11/2014 | Ingman et al. | |
| 2015/0038965 A1 | 2/2015 | Iger | |
| 2015/0073402 A1 | 3/2015 | Iger | |
| 2015/0157388 A1 | 6/2015 | Mehta et al. | |
| 2015/0202007 A1 | 7/2015 | Manstein et al. | |
| 2015/0283377 A1 | 10/2015 | Ingman et al. | |
| 2015/0297283 A1 | 10/2015 | Adanny et al. | |
| 2015/0306419 A1 | 10/2015 | Domankevitz | |
| 2015/0351825 A1 | 12/2015 | Adanny et al. | |
| 2016/0001073 A1 | 1/2016 | Ingman et al. | |
| 2016/0038591 A1 | 2/2016 | Wu et al. | |
| 2016/0045409 A1 | 2/2016 | Ingman et al. | |

FOREIGN PATENT DOCUMENTS

| | | |
|---|---|---|
| EP | 3788810 A2 | 8/1997 |
| JP | 2000140131 A | 5/2000 |
| JP | 2004215950 A | 8/2004 |
| JP | 2011045610 A | 3/2011 |
| JP | 2012075543 A | 4/2012 |
| JP | 2739091 B2 | 8/2013 |
| JP | 2013158363 A | 8/2013 |
| KR | 20080100569 A | 11/2008 |
| RU | 2003123515 A | 1/2005 |
| WO | 9300959 A1 | 1/1993 |
| WO | 0113988 A1 | 3/2001 |
| WO | 2006056055 A2 | 6/2006 |
| WO | 2007088348 A2 | 8/2007 |
| WO | 2008004818 A1 | 1/2008 |
| WO | 2013084189 A2 | 6/2013 |

\* cited by examiner

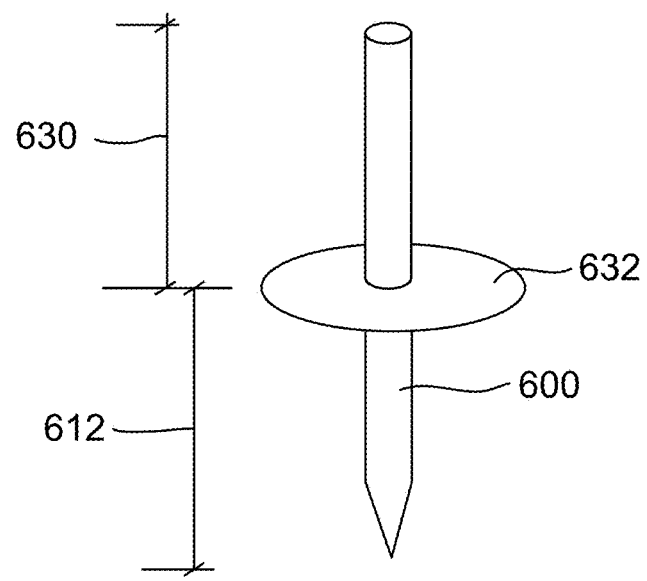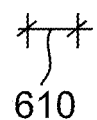
FIG. 6A

FIG. 22

+ Zinc-containing deposition island
* Copper-containing deposition island

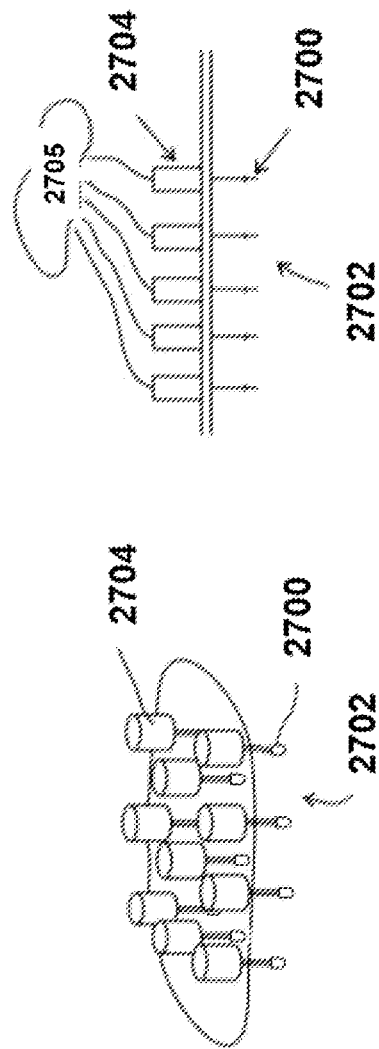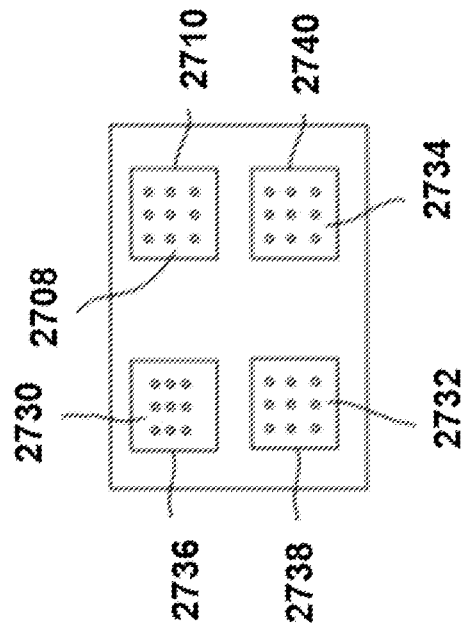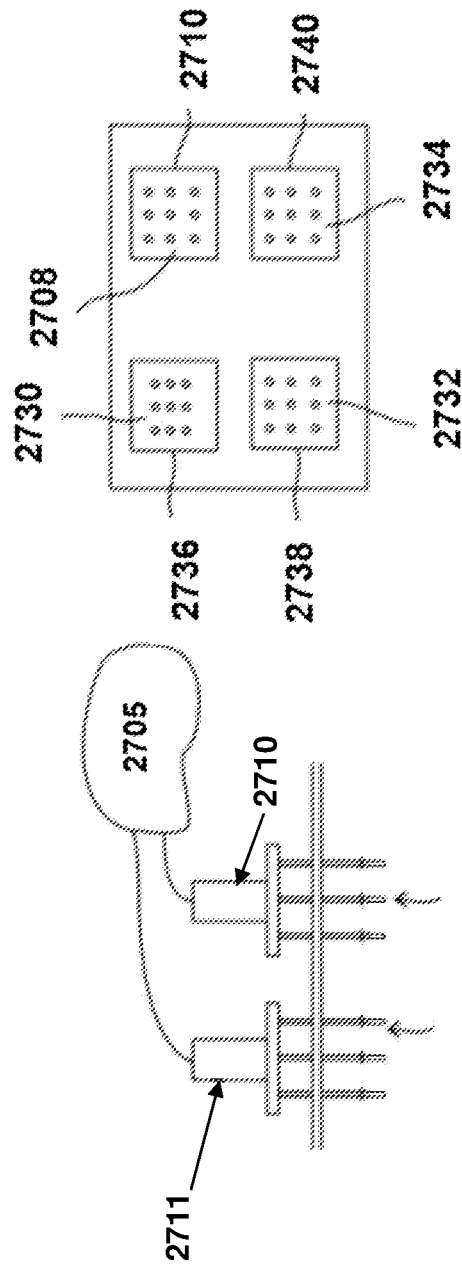
FIG. 27A
FIG. 27B
FIG. 27C
FIG. 27D

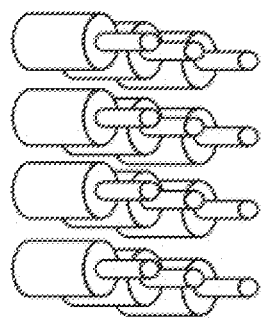
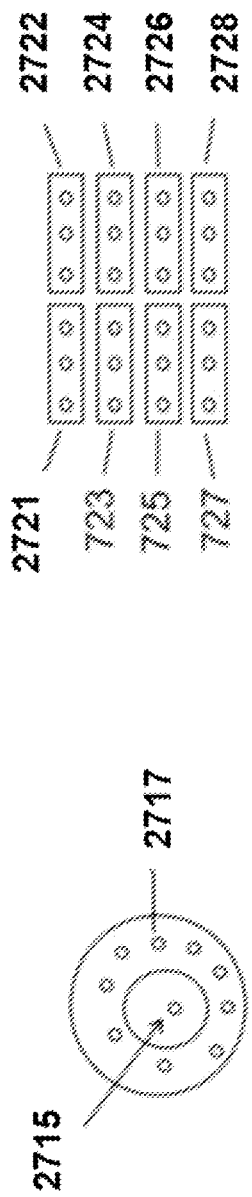
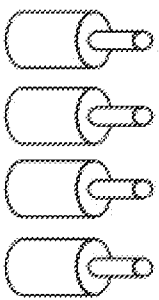
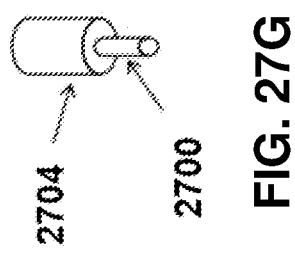

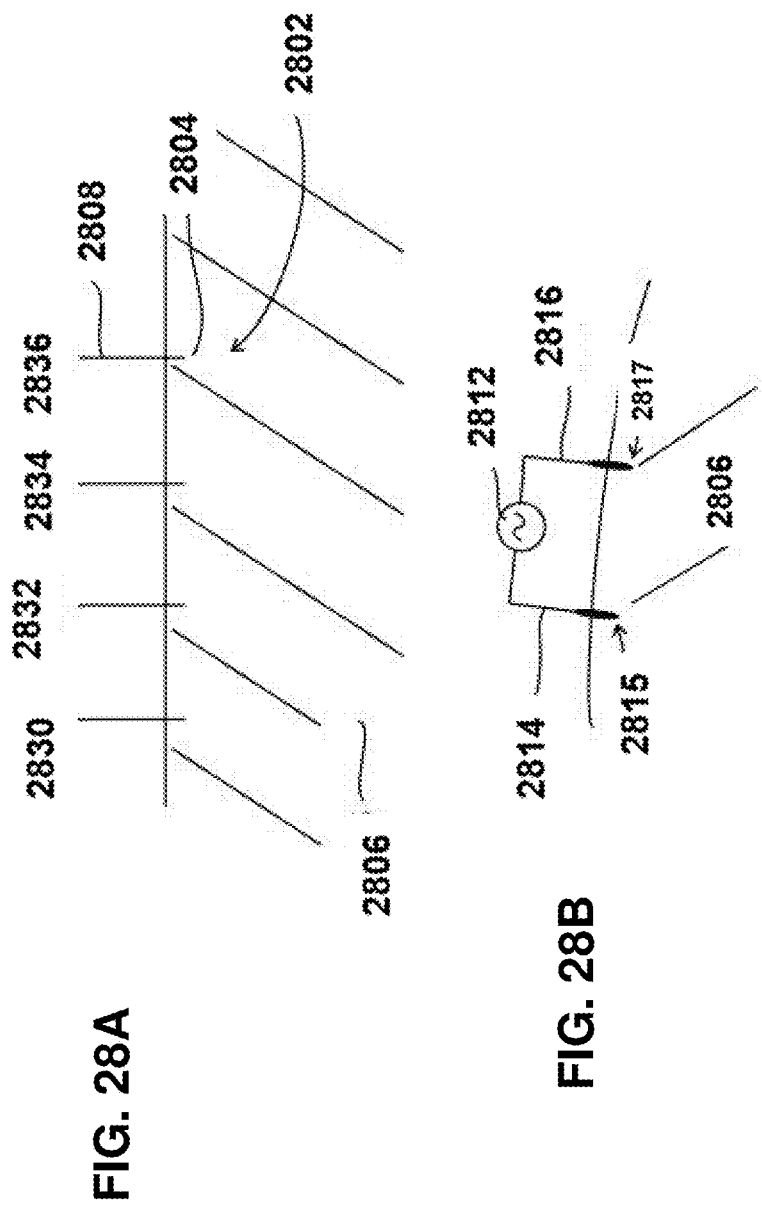

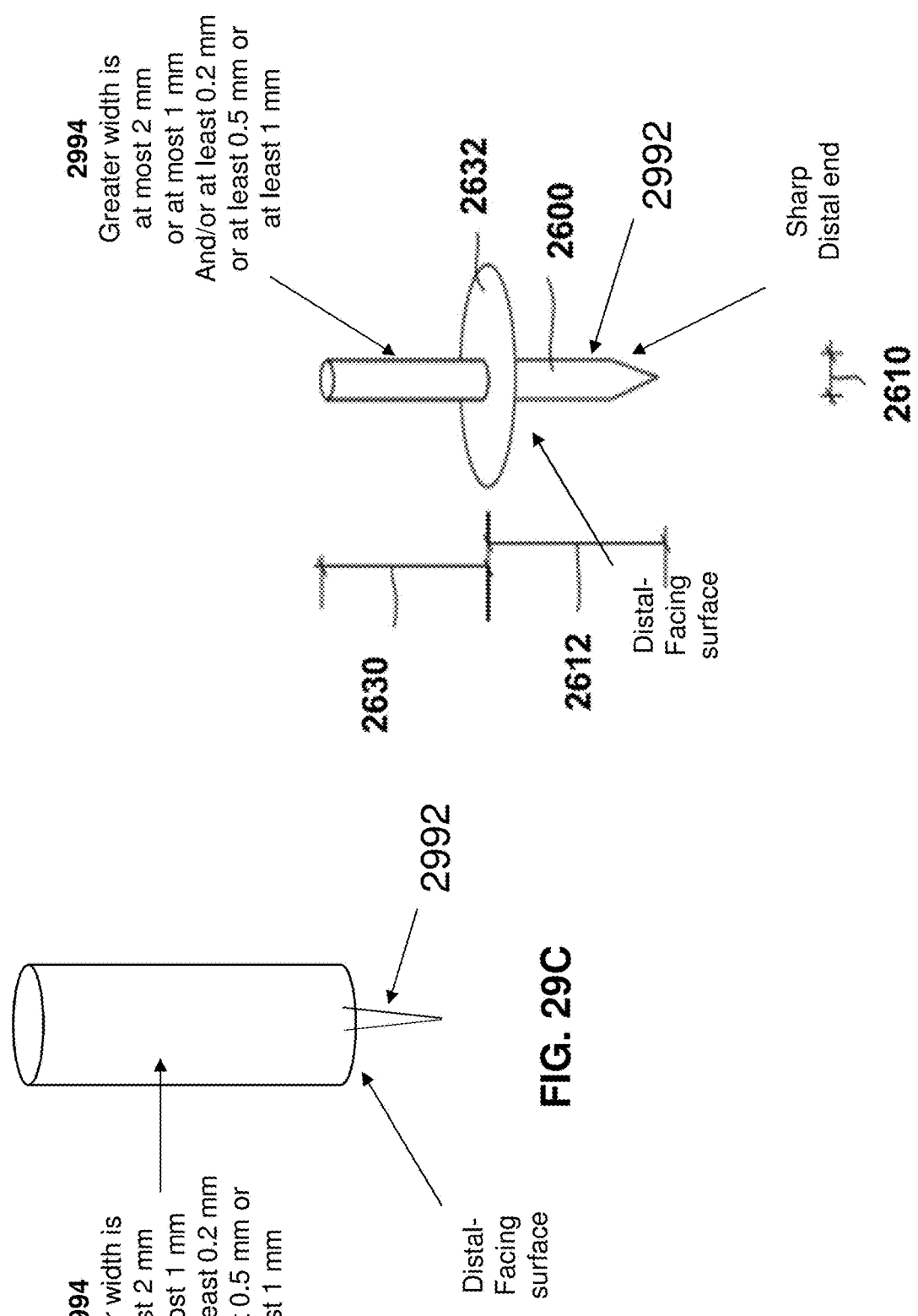

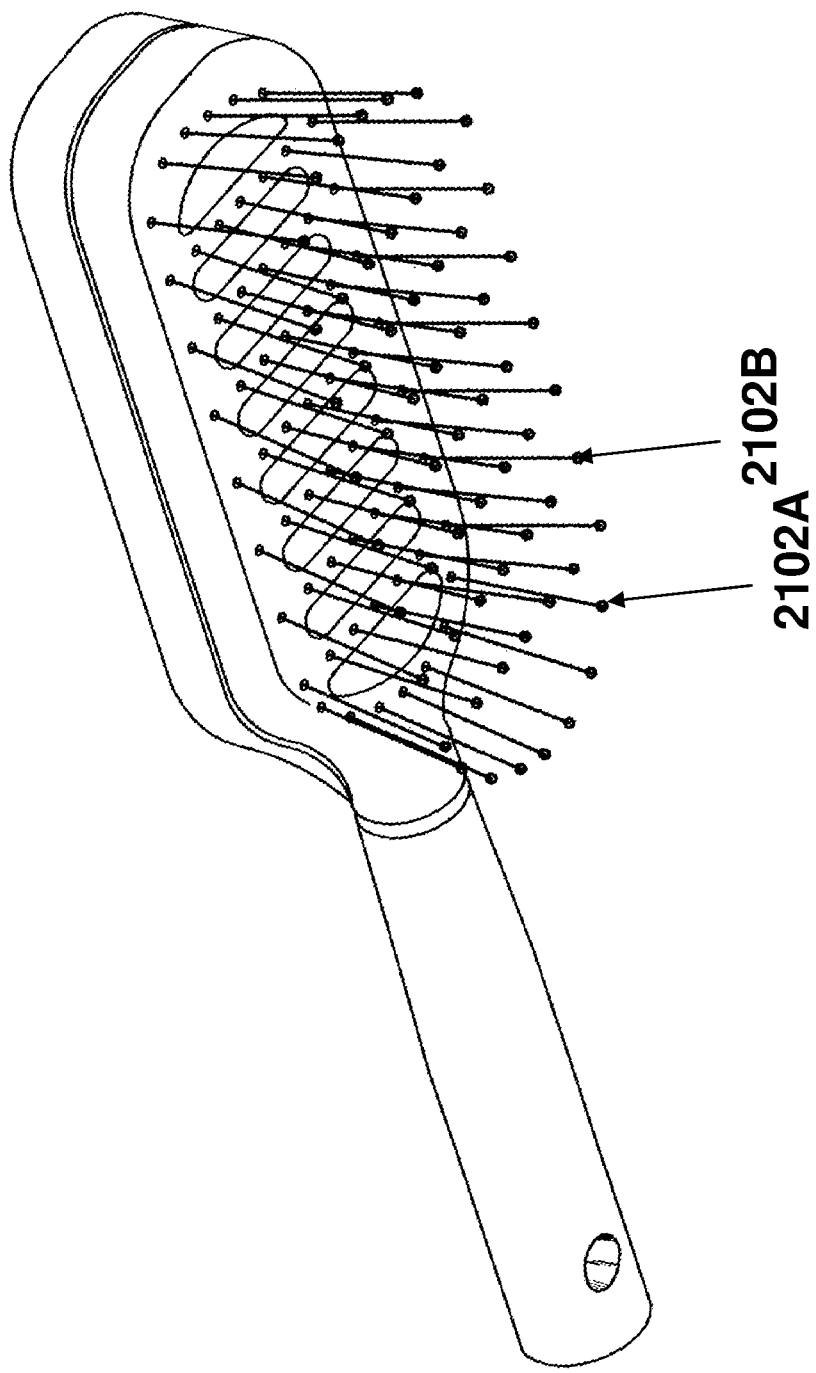

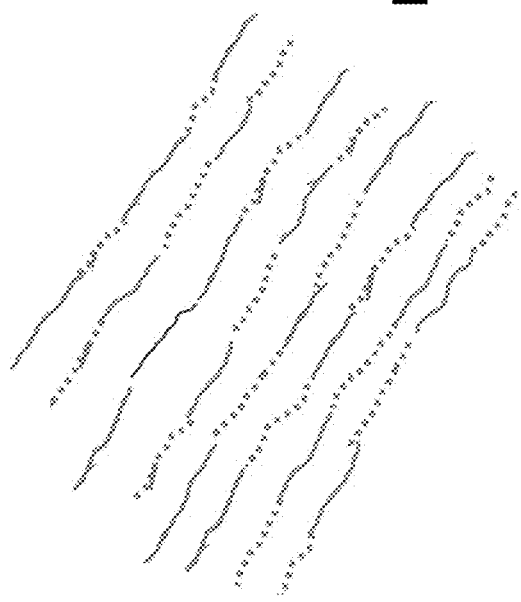
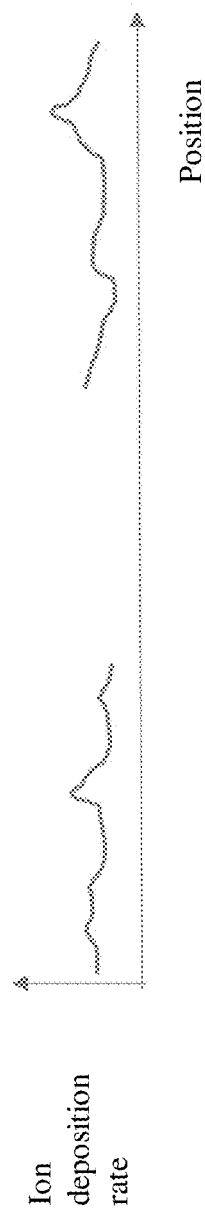
FIG. 30B
FIG. 30C

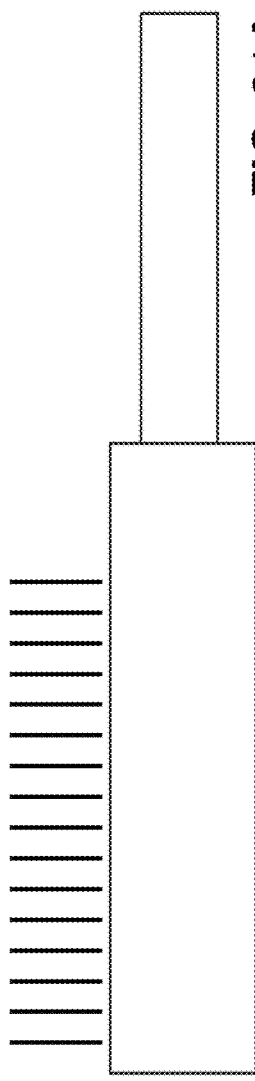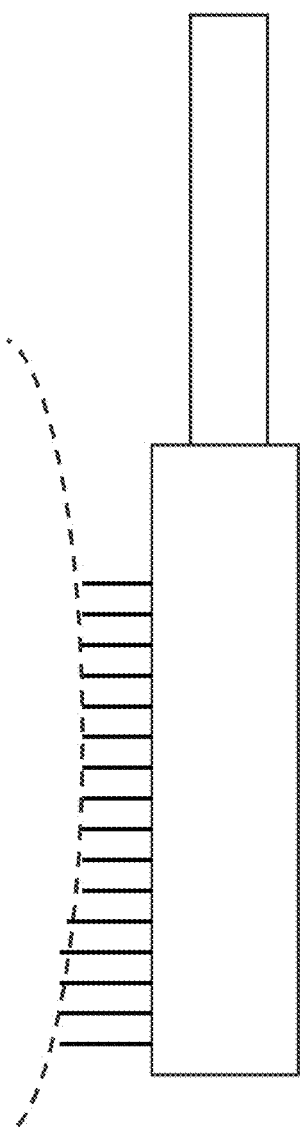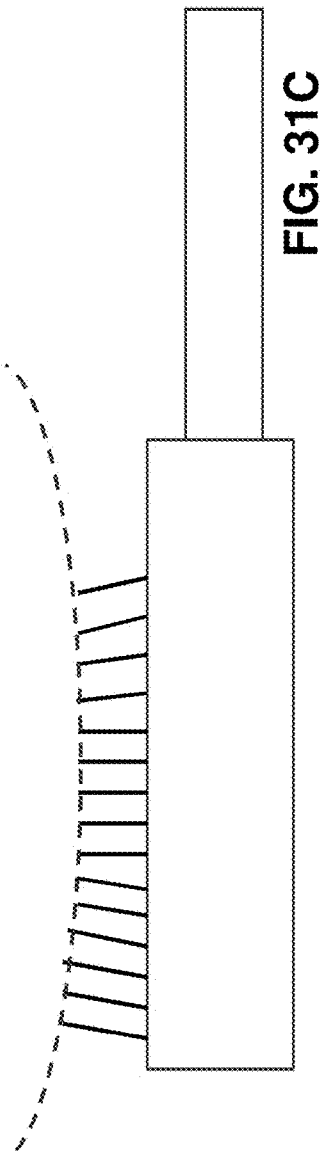

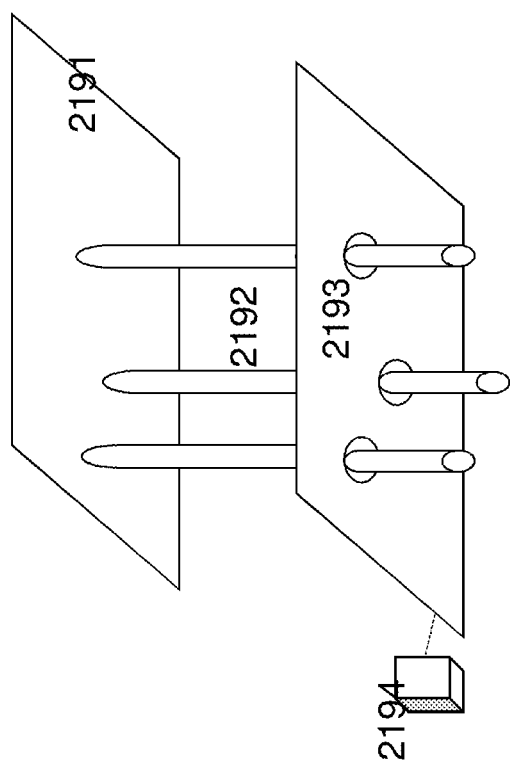

| case # | Initial Hair Count per cm2 | Final Hair Count per cm2 | Initial Terminal Hair Count per cm2 | Final Terminal Hair Count per cm2 | Treatment Period in days | Hair Count Change | Terminal Hair Count Change | Hair Count % Change | Terminal Hair Count % Change | age |
|---|---|---|---|---|---|---|---|---|---|---|
| 1 | 143 | 165 | 64 | 142 | 189 | 22 | 78 | 15 | 123 | 54 |
| 2 | 65 | 124 | 49 | 101 | 143 | 59 | 52 | 91 | 105 | 54 |
| 3 | 96 | 162 | 74 | 121 | 109 | 66 | 48 | 69 | 65 | 37 |
| 4A | 140 | 218 | 90 | 114 | 193 | 78 | 24 | 56 | 27 | 26 |
| 4B | 129 | 172 | 96 | 118 | 193 | 43 | 21 | 33 | 22 | 26 |
| 5 | 43 | 121 | 39 | 92 | 133 | 78 | 53 | 184 | 137 | 24 |
| 6 | 213 | 259 | 160 | 210 | 140 | 46 | 50 | 21 | 31 | 22 |
| 7 | 228 | 241 | 167 | 185 | 133 | 13 | 18 | 6 | 11 | 23 |
| 8 | 187 | 206 | 113 | 118 | 140 | 20 | 5 | 11 | 4 | 38 |
| 9 | 131 | 140 | 80 | 96 | 161 | 10 | 15 | 8 | 19 | 42 |
| 10 | 176 | 211 | 134 | 134 | 140 | 35 | -1 | 20 | -1 | 43 |
| 11 | 139 | 156 | 81 | 86 | 165 | 17 | 5 | 13 | 6 | 23 |
| 12 | 122 | 197 | 99 | 133 | 117 | 74 | 33 | 61 | 34 | 58 |
| 13A | 178 | 219 | 115 | 116 | 196 | 41 | 1 | 23 | 1 | 55 |
| 13B | 162 | 219 | 90 | 111 | 196 | 57 | 21 | 36 | 24 | 55 |
| 14 | 109 | 117 | 81 | 89 | 126 | 8 | 8 | 7 | 9 | 26 |
| 15 | 162 | 197 | 112 | 136 | 105 | 35 | 24 | 21 | 22 | 47 |
| 16 | 179 | 181 | 93 | 122 | 116 | 3 | 29 | 1 | 31 | 39 |
| 17 | 130 | 164 | 71 | 134 | 105 | 34 | 62 | 26 | 87 | 30 |
| 18 | 140 | 235 | 54 | 131 | 112 | 94 | 77 | 67 | 142 | 26 |

FIG. 43A

| case # | Initial Hair Count per cm2 | Final Hair Count per cm2 | Initial Terminal Hair Count per cm2 | Final Terminal Hair Count per cm2 | Treatment Period in days | Hair Count Change | Terminal Hair Count Change | Hair Count % Change | Terminal Hair Count % Change | age |
|---|---|---|---|---|---|---|---|---|---|---|
| 19  | 169 | 187 | 140 | 155 | 91  | 19 | 15 | 11  | 11 | 24 |
| 20A | 138 | 177 | 93  | 103 | 70  | 39 | 11 | 28  | 11 | 54 |
| 20B | 94  | 128 | 69  | 79  | 70  | 33 | 10 | 35  | 14 | 54 |
| 21  | 137 | 172 | 108 | 135 | 77  | 34 | 27 | 25  | 25 | 46 |
| 22  | 170 | 201 | 127 | 145 | 135 | 31 | 18 | 18  | 14 | 32 |
| 23  | 171 | 203 | 127 | 156 | 126 | 33 | 29 | 19  | 23 | 46 |
| 24A | 140 | 147 | 86  | 86  | 126 | 8  | 0  | 5   | 0  | 59 |
| 24B | 155 | 198 | 106 | 126 | 126 | 43 | 20 | 28  | 19 | 59 |
| 24C | 131 | 188 | 84  | 118 | 126 | 58 | 34 | 44  | 41 | 59 |
| 25A | 72  | 87  | 52  | 64  | 132 | 15 | 12 | 21  | 23 | 59 |
| 25B | 60  | 71  | 45  | 52  | 132 | 11 | 8  | 18  | 17 | 59 |
| 25C | 15  | 43  | 12  | 28  | 132 | 27 | 16 | 180 | 132 | 59 |
| 26A | 217 | 244 | 115 | 194 | 63  | 27 | 78 | 12  | 68 | 44 |
| 26B | 231 | 228 | 108 | 129 | 63  | -3 | 21 | -1  | 20 | 44 |

FIG. 43B

APPARATUS FOR STIMULATING HAIR GROWTH AND/OR PREVENTING HAIR LOSS

RELATED APPLICATION

This application is a continuation in part of U.S. patent application Ser. No. 14/739,832, which was filed on Jun. 15, 2015, and published as US Patent Publication 2016/0001073 on Jan. 7, 2016, and which is incorporated herein by reference.

FIELD AND BACKGROUND OF THE INVENTION

The present invention, in some embodiments thereof, relates to a device and method for stimulating skin and, more particularly, but not exclusively, to a device and method for directly stimulating the skin below the surface of the scalp to promote hair growth.

McDonough et al, in US patent application 2006/0253079 disclose "The present invention features a stratum corneum-piercing device including a microprotrusion member having a skin-contacting surface and plurality of stratum corneum piercing microprotrusions thereon, the device being adapted to move the microprotrusion member lateral to the surface of the skin surface upon contact with the skin."

Laubach, H.-J. T. (2006, February). Skin responses to fractional photothermolysis. Lasers in Surgery and Medicine. Lasers in Surgery and Medicine, 38(2), 142-149, disclose "A single treatment with fractional photothermolysis induces a wound healing response in the dermis."

Mayumi Ito, Z. Y. (2007, May). Wnt-dependent de novo hair follicle regeneration in adult mouse skin after wounding. Nature (447), 316-320, discloses "Here we show that, after wounding, hair follicles form de novo in genetically normal adult mice."

Chuong, C.-M. (2007, May). Regenerative biology: New hair from healing wounds. Nature (447), 265-266, discloses "It now seems that, as they heal, open skin wounds in adult mice form new hair follicles that follow similar developmental paths to those of embryos."

Sugimoto Y, L.-S. I.-T. (1995, May). Cations inhibit specifically type I 5 alpha-reductase found in human skin. J Invest Dermatol (104(5)), 775-778, discloses "The results showed that type I 5a-reductase was strongly inhibited by Cd, Cu, and Zn and moderately inhibited by Ni and Fe . . . . The data showed that cations could specifically control 5a-reductase activity expression, which is more strongly inhibited in a target tissue, especially the skin."

Additional background art includes:
Hiroyuki Hori, G. M. (1972). The Thickness of Human Scalp: Normal and Bald, Journal of Investigative Dermatology (58), 396-399.
Groux et al, in U.S. Pat. No. 5,800,477 disclose "Hair growth method and apparatus".
Whang et al, in U.S. Pat. No. 7,559,944 disclose "Hair growth apparatus".
Kim et al, in US patent application 2007/0038275 disclose "High-frequency electrotherapy apparatus".
Pitzen et al, in U.S. Pat. No. 6,834,206 disclose "Method for the electrical stimulation of human tissue to encourage hair growth".
Hans-Joachim et al, Skin Responses to Fractional Photothermolysis, Lasers in Surgery and Medicine 38:142-149 (2006), disclose "A single treatment with fractional photothermolysis induces a wound healing response in the dermis."
Nisato et al in U.S. Pat. No. 8,048,019 disclose "Multiple Nozzle Transdermal Drug Delivery System."
Chizmadzhev et al, "Electrical Properties of Skin at Moderate Voltages: Contribution of Appendageal Macropores," Biophysical Journal Volume 74 February 1998 843-856.
Maulsby et al, The interrelationship between the galvanic skin response, basal resistance, and temperature, Journal of Comparative and Physiological Psychology, Vol 53(5), October 1960, 475-479.
Taberner et al, Needle-free jet injection using real-time controlled linear Lorentz-force actuators, Medical Engineering & Physics—November 2012 (Vol. 34, Issue 9, Pages 1228-1235).
Rhodes W., Shallow Dermal Delivery of Vaccines Using Jet Injectors, Drug Development and Delivery, Vol. 3 No. 1 January/February 2003. Grimnes, Pathways of Ionic Flow through Human Skin in vivo, Department of Biomedical Engineering, Acta Derm Venereol, (Stockh) 1984; 64: 93-98.

SUMMARY OF THE INVENTION

Some embodiments of the present invention relate to methods and apparatus that were disclosed in PCT/IB2012/057041 which (i) was filed on Dec. 12, 2012; (ii) was published on Jun. 13, 2013 as WO/2013/084189; and (iii) is incorporated herein by reference in its entirety. In some embodiments, any feature or combination of features described in the present document may be combined with any feature of combination of features described in application PCT/IB2012/057041. US national phase application Ser. No. 14/361,742, filed on May 30, 2014, and published as US Patent Publication 20140330196 on Nov. 6, 2014, is also incorporated herein by reference.

An aspect of some embodiments of the invention relates to an apparatus and a method for selectively applying at least one stimulation modality to the skin in-situ. In an exemplary embodiment of the invention, stimulation is applied directly to at least one deeper layer of the skin of the scalp. Optionally, mechanical stimulation is applied, for example by at least one wheel comprising an array of needles. Optionally or alternatively, vibrational stimulation is applied, for example by vibration of the needle wheel. Alternatively or additionally, thermal stimulation is applied, for example by the needles. Alternatively or additionally, ions having 5-alpha-reductase inhibiting properties are directly deposited below the skin surface, for example by the needles.

In some embodiments, light stimulation is applied, for example using optical fibers to direct light to under the skin.

According to an aspect of some embodiments of the present invention, there is provided a device to stimulate a scalp comprising an array of stimulating elements adapted to pierce skin of said scalp no deeper than a thickness of a dermis, wherein the stimulating elements are arranged along a circumference of at least one wheel, wherein the wheel is adapted to roll over said scalp.

According to some embodiments of the invention, the stimulating elements comprise needles.

According to some embodiments of the invention, the stimulating elements release ions.

According to some embodiments of the invention, the stimulating elements are further adapted to additionally stimulate the scalp to enhance movement of the ions to a level sufficient to cause a biological effect.

According to some embodiments of the invention, a first group of stimulating elements of the array comprises a first metal; a second group of stimulating elements of the array comprises a second metal and the electrochemical gradient is sufficient to cause ions to travel in an amount sufficient to cause a biological effect.

According to some embodiments of the invention, the stimulating elements of the arrays comprise at least one metal and the metal comprises sufficient polarity and sufficient power with suitable polarity to cause ion injection.

According to some embodiments of the invention, the ions comprise at least one of copper ions and zinc ions.

According to some embodiments of the invention, the stimulating elements are arranged to part hair on the scalp during piercing by the stimulating elements; the arranged to part hair comprises stimulating elements separated from one another along a dimension to form a gap sufficiently wide to avoid trapping hairs; and the dimension comprises between 2 mm and 5 mm.

According to some embodiments of the invention, the stimulating elements of the array are separated by 0.1 mm to 1 mm along an axis; the stimulating elements are adapted to pierce skin to at least one depth between 100 micrometers and 1700 micrometers and the stimulating elements have a shape that forms a wound with a cross sectional area between 0.00001 $mm^2$ and 0.1 $mm^2$ at the dermis.

According to some embodiments of the invention, the device further comprises at least one element to vibrate at least one stimulating element.

According to some embodiments of the invention, vibrate comprises vibrating to increase a cross section of a wound under the scalp by the stimulating element by a factor ranging from 2×-20×.

According to some embodiments of the invention, vibrate comprises vibrating at a frequency ranging from 50 Hz-120 Hz and at an amplitude of 0.05 mm to 0.2 mm.

According to some embodiments of the invention, at least one stimulating element is electrically coupled to a power source.

According to some embodiments of the invention, the device further comprises ion injecting electrodes that touch the scalp connected to one terminal of the power source and an electrode that does not touch the scalp connected to a second terminal of the power source.

According to some embodiments of the invention, at least one stimulating element is configured to provide heat adapted to maintain a temperature of the stimulating elements during the piercing of the scalp.

According to some embodiments of the invention, the device further comprises a controller for regulating the application of at least one of: temperature of the stimulating elements, number of the piercings of the skin by the stimulating elements, vibration of the stimulating elements, and application of electrical current by the stimulating elements to the skin.

According to some embodiments of the invention, the device further comprises a memory, the memory coupled to the controller, the memory containing data correlating stimulation parameters with a treatment and a sensor, the sensor coupled to the controller, the sensor configured to monitor the piercing of the skin by the stimulating elements.

According to some embodiments of the invention, the device further comprises a drug reservoir comprising at least one drug to administer to the scalp.

According to some embodiments of the invention, the device further comprises at least one of a motor and a handle, each configured to displace the array across the scalp.

According to some embodiments of the invention, the device further comprises an encoder operable to count revolutions or partial revolutions of the wheel.

According to some embodiments of the invention, the stimulation comprises light.

According to some embodiments of the invention, the light is delivered through at least one of transparent discs, needles and optical fibers.

According to some embodiments of the invention, the stimulating elements comprise optical fibers acting as needles to pierce skin.

According to some embodiments of the invention, the stimulating elements comprise at least one injector configured to deliver stimulation directly into skin without needles.

According to an aspect of some embodiments of the present invention, there is provided a device to stimulate a scalp comprising an array of stimulating elements adapted to pierce skin of the scalp no deeper than a thickness of a dermis.

According to some embodiments of the invention, the stimulating elements are independently displaceable along a long axis of the stimulating elements to pierce the scalp in synchronized motion.

According to some embodiments of the invention, the stimulating elements comprise needles and the device further comprises a power source in electrical communication with at least two of the needles, the power source coupled to apply a voltage across the at least two needles; a vibrational element coupled to the array, the vibrational element operable to vibrate the needles along at least one axis; and a heat source thermally coupled to the needles, the heat source operable to raise needles to a temperature sufficient to raise a temperature of a volume of skin to within a range of 45-70 degrees Celsius.

According to some embodiments of the invention, at least one of the needles is coated or made from a first material that discharges zinc ions and at least one of the needles is coated or made from a second material that discharges copper ions.

According to an aspect of some embodiments of the present invention, there is provided a method of stimulating a scalp comprising forming channels at least below an epidermal layer of skin of the scalp; providing at least one stimulation from inside the channels; effecting tissue adjacent to the channels; and controlling the providing.

According to some embodiments of the invention, stimulating comprises wounding the skin in a non-contiguous pattern.

According to some embodiments of the invention, the wounding comprises wounding the skin at a density of 5-10 wounds per $mm^2$.

According to some embodiments of the invention, the controlling comprises wounding the skin in a period of time ranging from 0.01 seconds to 0.1 seconds per wound, to reduce a pain level.

According to some embodiments of the invention, the wounding comprises sufficiently wounding the skin to induce a wound healing response that regenerates hair follicles.

According to some embodiments of the invention, the wounding comprises selectively wounding at a depth selected according to a stage of baldness.

According to some embodiments of the invention, the stimulation is provided at multiple depths in the epidermis and/or dermis, ranging between 100 micrometers and 1700 micrometers.

According to some embodiments of the invention, the stimulating comprises applying a vibration under the skin.

According to some embodiments of the invention, the controlling comprises applying a vibration to increase the cross sectional size of a wound under the skin by a factor of 2-20×.

According to some embodiments of the invention, the stimulating comprises applying light under the skin.

According to some embodiments of the invention, the stimulating comprises applying heat sufficiently to induce a wound healing response that increases collagen production.

According to some embodiments of the invention, the controlling comprises applying sufficient heat to raise a temperature of a volume of skin to within a range of 45-70 degrees Celsius.

According to some embodiments of the invention, the stimulating comprises applying at least one voltage gradient to an area of the skin.

According to some embodiments of the invention, the stimulating comprises applying voltage in an opposite polarity to release copper ions under the skin.

According to some embodiments of the invention, the stimulation comprises forming a galvanic current that releases zinc ions under the skin.

According to some embodiments of the invention, the stimulating comprises applying an alternating current to alternate deposition of copper ions and zinc ions under the skin and a waveform of the alternating current is selected according to the ratio of the desired deposition of copper ions and zinc ions.

According to some embodiments of the invention, the stimulating comprises depositing a selected amount of at least one of copper ions and zinc ions under the skin to inhibit type I 5-alpha-reductase to stimulate hair growth; the selected amount of zinc ions ranges from 0.001 to 1 nanogram/$cm^2$ per treatment; the maximum total weekly dosage is between 2 nanograms/cm2 and 4 nanograms/cm2; and the selected amount of the copper ions ranges from 1% to 50% of the selected zinc ion amount.

According to some embodiments of the invention, controlling comprises applying the stimulation according to a position on the scalp and adjusting the providing according to hair growth.

According to some embodiments of the invention, controlling comprises measuring an impedance to determine contact of at least one needle with the skin.

According to some embodiments of the invention, a treatment session of the stimulating the scalp is repeated at least once daily and controlling comprises applying the stimulation during a particular treatment session to an area on the scalp smaller than the entire area being treated.

According to some embodiments of the invention, hair loss is treated by the stimulation of the scalp and the method further comprises comparing the providing to a treatment plan.

According to some embodiments of the invention, the stimulating comprises depositing at least one of copper ions and zinc ions under the skin to enrich the scalp with mineral nutrients in an amount sufficient to cause a biological effect; and create electrical fields.

An aspect of some embodiments of the invention relates to a kit for stimulating hair growth on a scalp comprising at least one wheel having an array of needles arranged along a circumference of the wheel, the wheel adapted for replacement in an apparatus for stimulating hair growth; and a power source for providing power to the apparatus.

In an exemplary embodiment of the invention, the kit further comprises a device for stimulating hair growth on a scalp, the device adapted to couple to the wheel.

In an exemplary embodiment of the invention, the kit further comprises software for communicating with a controller of the device for at least one of programming and monitoring a treatment of the device on the scalp.

In an exemplary embodiment of the invention, the kit further comprises an additive for applying to a scalp by a subject.

An aspect of some embodiments of the invention relates to a device to stimulate a scalp comprising an array of needles to pierce skin of the scalp no deeper than a thickness of a dermis, the needles are independently displaceable along a long axis of the needles.

In an exemplary embodiment of the invention, at least some needles are displaced along the long axis to pierce the scalp in synchronized motion.

An aspect of some embodiments of the invention relates to a device to stimulate a scalp comprising:

a. An array of needles adapted to piece skin of the scalp no deeper than a thickness of a dermis;

b. a power source in electrical communication with at least two of the needles, the power source coupled to apply a voltage across the at least two needles;

c. a vibrational element coupled to the array, the vibrational element operable to vibrate the needles along at least one axis; and d. a heat source thermally coupled to the needles, the heat source operable to raise needles to a temperature.

In an exemplary embodiment of the invention, at least one of the needles is coated or made from a first material that discharges zinc ions and at least one of the needles is coated or made from a second material that discharges copper ions. Optionally, the needles are arranged along a circumference of a wheel adapted to roll over the scalp.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

SUMMARY OF ADDITIONAL EMBODIMENTS

Apparatus for treating the scalp comprises a plurality of ion-releasing electrode protrusions configured so that when first and second of the protrusions are simultaneously in contact with human skin, at least partially-ionic current flows between the first and second electrode protrusions via the skin so as to deposit ions, released from the first and/or second electrode protrusions, on the skin.

Apparatus for treating the scalp comprises a plurality of ion-releasing electrode protrusions configured so that when first and second of the protrusions are simultaneously in contact with human skin, at least partially-ionic current flows between the first and second electrode protrusions via the skin so as to deposit on the skin, a ion and a counter-ion thereof, the ion and counter-ion being released from the first and/or second electrode protrusions.

In some embodiments, the plurality comprises at least 2 or at least at least 5 or at least 10 or at least 20 or at least 30 or at least 50 or at least 75 or at least 100 or at least 150 or at least 200 or at least 300 protrusions.

In some embodiments each electrode of the plurality is respectively associated with a respective counter-electrode of the electrode plurality, optionally a lateral displacement between the electrode and its respective counter-electrode being at most 1 cm or at most 7.5 mm or at most 5 mm, to define a respective electrode-pair such that when both electrodes of the respective electrode-pair are simultaneously in contact with human skin, at least partially-ionic current flows between the electrode protrusions of the respective electrode-pair via the skin so as to deposit ions, released from any one or both electrodes of the respective electrode-pair on the skin.

In some embodiments each electrode of the plurality is respectively associated with a respective counter-electrode of the electrode plurality, optionally a lateral displacement between the electrode and its respective counter-electrode being at most 1 cm or at most 7.5 mm or at most 5 mm, to define a respective electrode-pair such that when both electrodes of the respective electrode-pair are simultaneously in contact with human skin, at least partially-ionic current flows between the electrode protrusions of the respective electrode-pair via the skin so as to deposit at least two counter-ions, released from any one or both electrodes of the respective electrode-pair on the skin.

In some embodiments the plurality is operatively coupled to mechanical actuator(s) configured to repeatedly bring pairs of the electrode into and out of contact with a surface of skin so as to form ion-deposition islands thereon.

In some embodiments each electrode of the protrusion extends from a base-surface selected from the group consisting of (i) a surface of a wheel or cylindrical roller or spherical roller or disc; (ii) a rigid flat surface; and (iii) a conformable surface that is -flat in at least one configuration. In some embodiments, the roller is a cylindrical roller having a limited roll-range, for example, at most 270 degrees or at most 180 degrees or at most 135 degrees or at most 90 degrees or at most 60 degrees or at most 45 degrees.

In some embodiments a separation distance between the first and second protrusions is at most 1 cm or at most 5 mm.

A scalp-brush apparatus comprises a protrusion-base surface having at least one configuration where the protrusion-base surface is substantially flat; a plurality of ion-releasing electrode protrusions extending from the protrusion-base surface such that for at least one configuration of the protrusion-base surface: i. the ion-releasing electrode-protrusions are generally parallel to each other to pass through a common plane above the protrusion-base surface; and ii. for a patch-set of at least A non-overlapping square patches within the common-plane, each square-patch having an area of B mm2, respective first and second ion-releasing electrode-protrusions respectively pass through each square patch of the patch-set such that, for each patch of the patch-set, when the respective first and second ion-releasing electrode-protrusions are simultaneously in contact with human skin, an at least partially-ionic current flows between the respective first and second electrode-protrusions to deposit, onto the skin, ions that are respectively released from the respective first and/or second electrode-protrusions, wherein a value of A is selected from the group consisting of 3, 5, 7, 10, 12, 15, 20, 30, 50, 75, 100 and a value of B is selected from the group consisting of 10, 20, 30, 40, 50, 60, 70, 80, 100, 150, 200, 250, and 300.

A scalp-brush apparatus comprises a protrusion-base surface having at least one configuration where the protrusion-base surface is substantially flat; a plurality of ion-releasing electrode protrusions extending from the protrusion-base surface such that for at least one configuration of the protrusion-base surface: i. the ion-releasing electrode-protrusions are generally parallel to each other to pass through a common plane above the protrusion-base surface; and ii. for a patch-set of at least A non-overlapping square patches within the common-plane, each square-patch having an area of B mm2, respective first and second ion-releasing electrode-protrusions respectively pass through each square patch of the patch-set such that, for each patch of the patch-set, when the respective first and second ion-releasing electrode-protrusions are simultaneously in contact with human skin, an at least partially-ionic current flows between the respective first and second electrode-protrusions to deposit, onto the skin, a ion and a counter-ion thereof, the ion and counter-ion being released from the respective first and/or second electrode protrusions wherein a value of A is selected from the group consisting of 3, 5, 7, 10, 12, 15, 20, 30, 50, 75, 100 and a value of B is selected from the group consisting of 10, 20, 30, 40, 50, 60, 70, 80, 100, 150, 200, 250, and 300.

In some embodiments, the set of patches cover at least a rectangular region of the common plane having a length of X mm and a width of Y mm, wherein (I) a value of X of is at least 10 mm, or at least 20 mm or at least 30 mm or at least 40 mm and/or at most 100 mm or at most 75 mm or at most 50 mm or at most 40 mm or at most 30 mm or at most 20 mm and (ii) a value of Y is at least 30 mm or at least 40 mm or at least 50 mm or at least 60 mm or at least 70 mm or at least 80 mm or at least 90 mm or at 100 mm and/or at most 150 mm or at most 120 mm or at most 100 mm or at most 80 mm or at most 60 mm or at most 50 mm or at most 40 mm.

In some embodiments, protrusion-base surface has a first configuration where the protrusion-base surface is flat so that electrode-protrusions extending therefrom are parallel to each other and a second configuration where the protrusion-base is concave at least in one direction so that electrode-protrusions extending therefrom converge, an angle of convergence being at least 15 degrees. Alternatively, the base of the brush from which the protrusions extend may be concave in contrast to FIG. 14A to obtain a distal-end shape like in FIG. 15C

A scalp-treatment apparatus comprises a round roller (e.g. cylindrical or spherical) or a plurality of ion-releasing electrode protrusions extending from a surface of the round roller to pass through a round common-surface above the surface of the round roller such that, for a patch-set of at least A non-overlapping patches within the round common-surface, each patch being square within the round common-surface relative to the curvilinear coordinates defined by the common surface, each curvilinear-coordinate-relative-square-patch having an area of B mm2, respective first and second ion-releasing electrode-protrusions respectively pass through each curvilinear-coordinate-relative-square patch of the patch-set such that, for each patch of the patch-set, when the respective first and second ion-releasing electrode-protrusions are simultaneously in contact with human skin, an at least partially-ionic current flows between the respective first and second electrode-protrusions to deposit, onto the skin, ions that are respectively released from the respective first and/or second electrode-protrusions, a value of A is selected from the group consisting of 3, 5, 7, 10, 12, 15, 20, 30, 50, 75, 100 and a value of B is selected from the group consisting of 10, 20, 30, 40, 50, 60, 70, 80, 100, 150, 200, 250, and 300.

A scalp-treatment apparatus comprises a round roller (e.g. cylindrical or spherical) or a plurality of ion-releasing electrode protrusions extending from a surface of the round roller to pass through a round common-surface above the surface of the round roller such that, for a patch-set of at least A non-overlapping patches within the round common-surface, each patch being square within the round common-surface relative to the curvilinear coordinates defined by the common surface, each curvilinear-coordinate-relative-square-patch having an area of B mm2, respective first and second ion-releasing electrode-protrusions respectively pass through each curvilinear-coordinate-relative-square patch of the patch-set such that, for each patch of the patch-set, when the respective first and second ion-releasing electrode-protrusions are simultaneously in contact with human skin, an at least partially-ionic current flows between the respective first and second electrode-protrusions to deposit, onto the skin, a ion and a counter-ion thereof, the ion and counter-ion being released from the respective first and/or second electrode protrusions wherein, (I) a value of A is selected from the group consisting of 3, 5, 7, 10, 12, 15, 20, 30, 50, 75, 100 and (II) a value of B is selected from the group consisting of 10, 20, 30, 40, 50, 60, 70, 80, 100, 150, 200, 250, and 300.

In some embodiments wherein the roller is continuous along its central axis. In some embodiments wherein the roller comprises a disc-array of at least two or at least 3 or at least 4 or at least 5 or at least 10 thin co-axial discs spaced along a roller central axis, the electrode-protrusions being disposed around a circumference of each of the discs and radially protruding therefrom.

In some embodiments, a thickness of the each thin-disc is 0.75 mm or at most 0.5 mm or at most 0.25 mm or at most 0.1 mm.

In some embodiments wherein all discs of the disc-array rotate in-tandem with each other.

In some embodiments wherein for each pair of neighboring discs, inter-disc distance therebetween along the roller central axis is (i) at least 2 mm and/or (ii) at most 1 cm or at most 8 cm at most 6 mm and/or (iii) at least 5 times or at least 10 times or at least 20 time a thickness of a thickest disc of the disc-array.

In some embodiments wherein each disc has a diameter of at least 10 mm, or at least 20 mm, or at least 30 mm, or at least 40 mm, or at least 50 mm, or at least 60 mm, or at least 70 mm.

In some embodiments wherein configured so that for at least one pair of neighboring discs, an annular portion of an inter-disc region therebetween is substantially void, wherein (i) a length of the annular portion is at 20% or at least 30% or at least 40% or at least 50% an inter-disc distance between the neighboring discs; and (ii) an outer diameter of the annular portion is at least that of the neighboring discs; and (iii) an inner diameter of the annular portion is at most 5 mm or at most 10 mm less than that the of the neighboring discs.

A scalp-treatment apparatus comprises a disc-array of at least two or at least 3 or at least 4 or at least 5 or at least 10 co-axial discs (e.g. thin discs) spaced along a roller central axis; ion-releasing electrode-protrusions being disposed around a circumference of each of the discs and radially protruding therefrom such that when first and second of the protrusions are simultaneously in contact with human skin, at least partially-ionic current flows between the first and second electrode protrusions via the skin so as to deposit ions, released from the first and/or second electrode protrusions, on the skin.

A scalp-treatment apparatus comprises a disc-array of at least two or at least 3 or at least 4 or at least 5 or at least 10 co-axial discs (e.g. thin discs) spaced along a roller central axis;

b. ion-releasing electrode-protrusions being disposed around a circumference of each of the discs and radially protruding therefrom such that when first and second of the protrusions are simultaneously in contact with human skin, at least partially-ionic current flows between the first and second electrode protrusions via the skin so as to deposit on the skin, a ion and a counter-ion thereof, the ion and counter-ion being released from the first and/or second electrode protrusions.

In some embodiments wherein the roller is continuous along its central axis.

In some embodiments wherein the roller comprises a disc-array of at least two or at least 3 or at least 4 or at least 5 or at least 10 thin co-axial discs spaced along a roller central axis, the electrode-protrusions being disposed around a circumference of each of the discs and radially protruding therefrom.

In some embodiments, a thickness of the each thin-disc is 0.75 mm or at most 0.5 mm or at most 0.25 mm or at most 0.1 mm.

In some embodiments wherein all discs of the disc-array rotate in-tandem with each other.

In some embodiments wherein for each pair of neighboring discs, inter-disc distance there between along the roller central axis is at least 2 mm and/or at most 1 cm or at most 8 cm at most 6 mm and/or at least 5 times or at least 10 times or at least 20 time a thickness of a thickest disc of the disc-array.

In some embodiments wherein each disc has a diameter of at least 10 mm, or at least 20 mm, or at least 30 mm, or at least 40 mm, or at least 50 mm, or at least 60 mm, or at least 70 mm.

In some embodiments wherein configured so that for at least one pair of neighboring discs, an annular portion of an inter-disc region there between is substantially void, wherein a length of the annular portion is at 20% or at least 30% or at least 40% or at least 50% an inter-disc distance between the neighboring discs; and an outer diameter of the annular portion is at least that of the neighboring discs; and an inner diameter of the annular portion is at most 5 mm or at most 10 mm less than that the of the neighboring discs.

In some embodiments wherein there is a round-roller (e.g. cylinder but not only) comprising the cylindrical roller and/or wherein the one or more discs along the common rotation axes so that outer diameters thereof substantially lie along a common geometrical cylinder, thereby defining a cylindrical roller, wherein the cylindrical roller has a limited roll-range, for example, at most 270 degrees or at most 180 degrees or at most 135 degrees or at most 90 degrees or at most 60 degrees or at most 45 degrees.

In some embodiments wherein at least sensor configured to sense at least one parameter related to operation of the apparatus and/or to a status of skin treated by the apparatus; and (ii) at least one response-element configured to generate a response, responsively to the results of the sensing.

In some embodiments, at least one sensor(s) is selected from the group consisting of an ion-deposition rate sensor configured to sense a rate of deposition of ions on the skin by the at least partially-ionic current; a force or pressure sensor configured to sense an amount of force or pressure between the electrode-protrusion(s) and skin; skin-color sensor, a current sensor configured to sense a magnitude of current via the skin via electrode-protrusions; a trapped or tangled hair sensor configured to sense a presence or absence or amount of hair trapped within or entangled to the roller (e.g. mechanical and/or optical); a skin wetness sensor; a skin temperature sensor (e.g. based on IR); a scalp thickness sensor (e.g. based on ultrasound); a roll counter; and an accelerometer.

In some embodiments wherein at least one response-element is selected from the group consisting of a vibration controller configured to control at least one of an amplitude, frequency, direction, relative-amplitude of mechanical vibrations of the electrode-protrusion(s); an alert-signal generator configured to generate an alert signal (e.g. visual and/or audio and/or tactile); a session-duration regulator configured to regulate a duration of a treatment session (e.g. by signaling a 'session alert' alert or by shutting off the vibrations and/or the light and/or the electrical current driving ion deposition); an inter-protrusion voltage-regulator configured to regulate a voltage between electrode protrusions (e.g to increase a voltage by a factor of at least 2 or at least 5 or at least 10; e.g. to generate a series of pulses); a roller-resistance or disc-rolling-resistance controller (e.g. mechanical and/or electrical) configured to regulate a degree of resistance to rolling of the disc and/or roller (e.g. to increase the resistance if the 'effectiveness of treatment'— e.g. current between electrodes—is too low; a depth-penetration controller configured to regulate a depth to which tips of the electrode-protrusions penetrate the skin (e.g. by regulating a length of the mini-needle or a location of the stopper); a base-surface shape-regulator configured to regulate an extent of a deviation from flatness of the generally-flat base-surface from which the protrusions extend.

In some embodiments the response element responds to the results of the sensing in accordance with a number of previous sessions that the device has been used.

In some embodiments the plurality of electrode protrusions configured, when at least two of the protrusions are simultaneously in contact with human skin, at least partially-ionic electric current flows between first and second protrusions via the skin, wherein the protrusions are disposed around the circumference of a wheel or roller having only partial rotational freedom.

In some embodiments wherein at least one of, or at least a plurality of, or at least a majority of the electrode protrusions are blunt at distal ends thereof.

In some embodiments wherein at least one of, or at least a plurality of, or at least a majority of the electrode protrusions are sharp at distal ends thereof.

In some embodiments wherein at least one, or at least a plurality of, or at least a majority of the electrode-protrusion comprises an electrode-protrusion main body (for example, characterized by a greater-thickness of at most 2 mm and/or a length of at least 0.2 mm) the main-body being blunt at its distal end and/or the main-body having a blunt distal-facing surface; and one or more sharp mini-needle(s) extending from the blunt distal end or the blunt distal-facing surface of the main body, the mini-needle being sharp at a distal surface thereof.

In some embodiments, a thickness of the sharp mini-needle is at most 100 microns and/or a length the sharp mini-needles is at least 10 microns or at least 20 microns and/or at most thereof being between 10 and 150 microns.

In some embodiments wherein at a location distanced 50 microns from a tip of the electrode protrusion, a cross-section of the electrode-protrusion is at least 0.001 mm^2, or at least 0.005 mm^2, or at least 0.01 mm^2, or at least 0.02 mm^2, or at least 0.05 mm^2.

In some embodiments wherein when a tip of the electrode-scalp is brought into contact with a healthy human scalp, an electrode-scalp contact area for each electrode-scalp contact event is at most 10 mm2.

In some embodiments wherein configured to regulate a maximum skin-penetration-depth of electrode-protrusions to at most 100 microns or at most 75 microns or at most 50 microns or at most 20 microns when a tip of the electrode-protrusion is pressed against a healthy human scalp at a pressure of 0.1 to 5 MPa.

In some embodiments wherein at least one of, or at least a plurality of, or at least a majority of the electrode protrusions are flexible, for example, to provide a variation in a base-tip distance of at least 1 mm or at least 2 mm or least 3 mm or at least 5 mm or at least 7 mm or at least 10 mm and/or at least 10% of (or at least 25% of, or at least 50% of) a length of the electrode-protrusion. In some embodiments wherein an electrical power source configured to at least partially drive the at least partially-ionic current between electrode-protrusions via the skin to at least partially drive the ion deposition thereon.

In some embodiments, the electrical power source produces time varying current between the electrodes, for example, alternating current, for example, at a frequency of at least 0.1 Hz and/or at most 10 Hz.

In some embodiments wherein each of the electrode-protrusions is laterally distanced from its nearest neighbor by at most 1 cm or at most 5 mm.

In some embodiments wherein an onboard source(s) of mechanical vibration to vibrate each of the electrode-protrusions in at least one or in both lateral-directions and/or along a lateral direction defined by the electrode-protrusion.

In some embodiments wherein a light source, for example, configured to emit primarily light having a wavelength of at least about 620 nm and at most about 680 nm, for example, a LED or laser or source of coherent light.

In some embodiments wherein the ion-releasing electrodes are configured as hybrid light guide:ion-releasing electrodes so that light received from the light source longitudinally travels within the hybrid light guide:ion-releasing electrodes, for example, so that the light exits from the hybrid light guide:ion-releasing electrodes along the longitudinal direction of the hybrid light guide:ion-releasing electrode—for example, constructed of a transparent polymer either electrically conducting or coated by an electrically-conducting substance—e.g. comprising metal ions.

In some embodiments wherein employing the apparatus to deposit metal ions on the scalp and/or to provide a massage thereto and/or to illuminate the scalp.

In some embodiments wherein employing the apparatus to deposit metal ions on the scalp and/or to provide a massage thereto and/or to illuminate the scalp.

In some embodiments, for treating or preventing a hair-condition of a user, the user's scalp dividable into a scalp-patch-set of n mm×n mm non-overlapping square scalp patches, n being a positive number having a value of at most 5, the apparatus comprises means for subjecting the user's scalp to at least q distinct electrode-scalp contact events within a time-interval of at most one minute, the time interval being dividable into m non-overlapping equal-duration sub-intervals covering the time-interval, m being a positive integer having a value of at least 5, q being a positive integer having a value of at least 200, the method performed such that for at least a majority of the electrode-scalp contact events, no electrode of the event enters into the dermis; a duration of each electrode-scalp contact event is at most 100 milliseconds; an electrode-scalp contact area for each electrode-scalp contact event is at most 10 mm2; for each electrode-scalp contact event, an electrical current flows between the electrode and the scalp so as to deposit electrode-released ions of a first metal or of a second metal on the scalp, thereby forming a respective metal-ion-deposition island on the user's scalp; for each of the m non-overlapping equal-duration sub-intervals, at least p electrode-scalp contact events occur, p being a positive integer having a value of at least 1; at least 5% of the electrode-scalp contact events are first-metal-depositing and at least 5% of the electrode-scalp contact events are second-metal-depositing; and at least one first-metal-deposition-island and at least one second-metal-deposition-island are both respectively and distinctly formed on each n mm×n mm scalp scalp-patch selected from a 10-member scalp-patch sub-set of the scalp-patch set.

In some embodiments, treating or preventing a hair-condition of a user, the user's scalp dividable into a scalp-patch-set of n mm×n mm non-overlapping square scalp patches, n being a positive number having a value of at most 5, the method comprises subjecting the user's scalp to at least q distinct electrode-scalp contact events within a time-interval of at most one minute, the time interval being dividable into m non-overlapping equal-duration sub-intervals covering the time-interval, m being a positive integer having a value of at least 5, q being a positive integer having a value of at least 200, the method performed such that for at least a majority of the electrode-scalp contact events, no electrode of the event enters into the dermis; a duration of each electrode-scalp contact event is at most 100 milliseconds; an electrode-scalp contact area for each electrode-scalp contact event is at most 10 mm2; for each electrode-scalp contact event, an electrical current flows between the electrode and the scalp so as to deposit electrode-released ions of a first metal or of a second metal on the scalp, thereby forming a respective metal-ion-deposition island on the user's scalp;

v. for each of the m non-overlapping equal-duration sub-intervals, at least p electrode-scalp contact events occur, p being a positive integer having a value of at least 1; at least 5% of the electrode-scalp contact events are first-metal-depositing and at least 5% of the electrode-scalp contact events are second-metal-depositing; and at least one first-metal-deposition-island and at least one second-metal-deposition-island are both respectively and distinctly formed on each n mm×n mm scalp scalp-patch selected from a 10-member scalp-patch sub-set of the scalp-patch set.

In some embodiments wherein during at least some of the electrode-scalp contact events, externally-generated electrical current is respectively forced between the electrode and the scalp so as to respectively deposit or increase a deposition-rate of electrode-released ions of the first or second metal onto the scalp.

In some embodiments wherein a value of q is at least 1000.

In some embodiments wherein a value of p is at least 5.

In some embodiments wherein a value of m is at least 10.

In some embodiments wherein a value of p is at least 5.

In some embodiments wherein for at least 75% of the electrode-scalp contact events, no electrode enters into the dermis.

In some embodiments wherein at least 20% of the events are first-metal-depositing.

In some embodiments wherein at least 20% of the events are second-metal-depositing.

In some embodiments wherein at least four metal-deposition-islands are respectively and distinctly formed on each n mm×n mm scalp-patch selected from a 10-member scalp-patch sub-set of the scalp-patch set, the four metal-deposition islands comprising at least two first-metal-depositing islands and at least two second-metal-depositing-islands.

In some embodiments wherein a duration of each electrode contact event is at most 50 milliseconds.

In some embodiments wherein a duration of each electrode contact event is at most 25 milliseconds.

In some embodiments wherein an electrode-scalp contact area for each electrode-scalp contact event is at most 5 mm2.

In some embodiments wherein during each of a majority of the electrode-scalp contact events, the scalp is respectively subjected to an electrode-applied pressure of at least 0.5 mega-Pascals.

In some embodiments wherein during each of at least 75% of the electrode-scalp contact events, the scalp is respectively subjected to an electrode-applied pressure of at least 0.5 mega-Pascals.

In some embodiments wherein during each of a majority of the electrode-scalp contact events, the scalp is respectively subjected to an electrode-applied pressure of at least 1 mega-Pascal.

In some embodiments wherein during each of at least 75% of the electrode-scalp contact events, the scalp is respectively subjected to an electrode-applied pressure of at least 1 mega-Pascal.

In some embodiments wherein a value of q is at least 250, and wherein for each of the electrode-scalp contact events, at least some of the released metal-ions deposited on the scalp are provided from an electrode interior of the electrode and/or from an electrode metal-coating that is integrally formed with the electrode.

In some embodiments wherein during a majority of the electrode-scalp contact events, externally-generated electrical current is forced between the electrode and the scalp so as to deposit or increase a deposition-rate of electrode-released ions of the first or second metal onto the scalp.

Apparatus for Treating the Scalp Comprising:

a plurality of ion-releasing electrode protrusions configured so that when first and second of the protrusions are simultaneously in contact with human skin, at least partially-ionic current flows between the first and second electrode protrusions via the skin so as to deposit ions, released from the first and/or second electrode protrusions, on the skin.

Apparatus for Treating the Scalp Comprising:

a plurality of ion-releasing electrode protrusions configured so that when first and second of the protrusions are simultaneously in contact with human skin, at least partially-ionic current flows between the first and second electrode protrusions via the skin so as to deposit (e.g. sequentially) on the skin, a ion and a counter-ion thereof (for example, to cycle back and forth between a first-mode where the ion is deposited without the counter ion and a second mode where the counter ion is deposited without simultaneously depositing the ion), the ion and counter-ion being released from the first and/or second electrode protrusions. In some embodiments, a separation distance between the first and second protrusions is at most 1 cm or at most 5 mm.

Embodiments of the invention relate to a device and method whereby the scalp is rapidly and repeatedly touched by ion-releasing electrodes. During each 'ion-depositing electrode-scalp contact event' an electrode (e.g. through which externally generated electrical current flows) is very briefly brought into and out of contact with the scalp—e.g. in contact with the scalp for at most 100 milliseconds. During each brief contact event, the electrode is briefly brought into and out of contact with the scalp so as to deposit metal on the scalp to form a small (e.g. at most 15 mm2 in area) metal-deposition island on the scalp. In some embodiments, each brief contact event is effective to apply a significant amount of highly-localized pressure. e.g at least 0.5 megapascals [MPa] localized over a contact area of at least 0.1 mm2 and at most 10 mm2. The rapid application of non-wounding but significant pressure subjects the scalp to a 'micromassage.'

The method is performed so that: (i) a large number of such electrode-events are sequentially performed within a relatively short period of time; (ii) at least two types of metal-deposition islands are formed on the scalp (e.g. a first type comprising zinc and a second type comprising copper); and (iii) both types of metal-deposition islands are distributed over a significant portion of the scalp. As discussed below, it is possible to quantify the extent of distribution of metal-islands on the scalp and the proximity of first and second types of metal islands (e.g. 'cathode-islands' and 'anode-islands'), in terms of 'scalp patches.'

Not wishing to be bound by theory, it is believed that the deposition of a relatively large number of very small but distinct metal-ion-deposition-islands on the user's scalp forms a significant number of 'micro-battery-cell' on the user's scalp when both cation islands and anion islands are distributed over a region of the scalp. It is believed that after deposition of the islands, small electrical currents may be sustained between the distinct deposition islands (e.g. due to proximity of distinct cathode-islands and anode-islands) along the user's scalp for some period of time (e.g. at least hours). It is believed that the combination of the time-sustained electrical stimulation together with the mild trauma of the micro-massage obviates the need to employ wounding-based techniques to stimulate the scalp.

Although skin-wounding stimulates cell-growth in the skin (and possibly hair-growth) by inducing a biological 'wound-healing' process, certain users may consider wounding devices as invasive and unpleasant to use. It is believed that the presently-disclosed ion-delivering micro-massage obviates the need for a more severe treatment regimen based on wounding, while still combating baldness.

When metallic-ions are 'released from' an electrode this is in contrast with pre-applying an ion-containing topical agent (e.g. an ion-containing liquid or cream or gel) to the skin and then using an electrode to drive the ions into the skin. When metallic-ions are 'released from', the source of the metallic ions is from the electrode itself. The released metal-ions are provided from an interior of the electrode (e.g. from a reservoir disposed within the electrode) or from actual material of the electrode (i.e. the electrode is at least partially constructed from the metal which is then released) or from an 'integrally-formed' coating on the electrode—i.e. the electrode is pre-coated with the metal so that the metal coating is integrally formed with the electrode and then metal of this coating is released.

By 'releasing' metallic ions from the electrode rather than relying on a topically-applied ion-containing flowable-fluid (e.g. liquid, cream, gel), it is possible to deliver distinct ion-deposition metal-ion deposition islands. After treatment, small electrical currents may flow between these metal-deposition islands to electrically stimulate the skin after the electrode-contacting events have ceased, thereby providing a sustained effect.

A number of techniques are disclosed herein for rapidly bringing electrode into and out of contact with the scalp. In one example, a plurality of electrode-protrusions (e.g. having a rounded tip) are disposed around a roller. As the roller is rolled over the surface of the skin, the electrodes are briefly brought into contact with and out of contact with the skin so that a large number of very brief electrode contact events are performed. A second example relates to a motorized device. In this second example, electrodes (eg. having a rounded tip) are rapidly, reciprocally and vertically brought into contact and out of contact with the scalp.

Despite the very-brief contact periods (i.e. less than 0.1 seconds or even less) between each electrode and the scalp, a therapeutically effective amount of metallic-ions may be deposited in each treatment island. Towards this end, an external electrical power source may boost a rate of ion-delivery to each treatment island, instead of relying only on a galvanic potential between electrodes of different polarity. Not wishing to be bound by theory, externally-driving ion deposition on the scalp may, once again, obviate the need for a more mechanically-aggressive wounding-based treatment where most electrode-contact events lead to penetrating of the dermis.

It is now disclosed a method of treating or preventing a hair-condition of a user, the user's scalp dividable into a scalp-patch-set of n millimeter (mm)×n millimeter (mm) non-overlapping scalp patches, where n a positive number having a value of at most 5. The method comprises subjecting the user's scalp to at least q distinct electrode-scalp contact events within a time-interval of at most one minute and dividable into m non-overlapping equal-duration sub-intervals covering the time-interval, m begin a positive integer having a value of at least 5, q being a positive integer having a value of at least 200. For the non-limiting example where m is 5, the m equal-duration sub-intervals are [0.12 seconds], [12 seconds, 24 seconds], [24 seconds, 36 seconds], [36 seconds, 48 seconds], and [48 seconds, 60 seconds]. Since every moment within the one-minute time interval i within one of the sub-intervals, the sub-intervals may be said to collectively 'cover an entirety of the time-interval.

In some embodiments, for at least a majority of the electrode-scalp contact events, no electrode of the event enters into the dermis;

In some embodiments, a duration of each electrode scalp contact event is at most 100 milliseconds—i.e. for each electrode-scalp no more than 100 milliseconds elapses between (i) a time when the electrode is brought into contact with the scalp; and (ii) a time when the electrode is taken out of contact with the scalp.

In some embodiments, an electrode-scalp contact area for each electrode-scalp contact event is at most 10 mm$^2$.

In some embodiments, for each electrode contact event, an electrical current flows between the electrode and the scalp so as to deposit electrode-released ions of a first metal or of a second metal on the scalp, thereby forming a respective metal-ion-deposition island on the user's scalp. Thus, each contact event deposits either a first metal (e.g. zinc) and a second metal (e.g. copper) but not both.—other metals other than the first and second metal may additionally be deposited along with the first or the second metal.

In some embodiments, for each of the non-overlapping equal-duration sub-intervals, at least p electrode-scalp contact events occur, p being a positive integer having a value of at least 1.

In some embodiments, at least 5% of the events are first-metal-depositing and at least 5% of the events are second-metal-depositing.

In some embodiments, at least one first-metal-deposition-island and at least one second-metal-deposition-island are both respectively and distinctly formed on each n mm×n mm scalp-patch selected from a 10-member scalp-patch sub-set of the scalp-patch set.

In some embodiments, the islands may be 'distinct' from each other for some the islands may form a 'bridge' between the formerly-'distinct' islands. This does not detract from the fact that for at least some period of time, the islands were 'distinct' from each other.

In some embodiments, during at least some of the electrode-scalp contact events, externally-generated electrical current (i.e. as opposed to galvanic current) is forced between the electrode and the scalp (for example, between two different electrodes that are simultaneously in contact with the scalp where due to an externally-maintained electric potential difference between the electrodes, electrical current flows therebetween via the scalp) so as to deposit or increase a deposition-rate of electrode-released ions of the first or second metal onto the scalp. Some galvanic current may be present, but the externally-generated electrical current may boost a rate of metal-ion-deposition.

A cosmetic method of treating or preventing a hair-condition of a user comprising: subjecting the user's scalp to at least 200 distinct electrode-scalp contact events during a time-interval of at most one minute and dividable into 5 non-overlapping equal-duration sub-intervals covering the time-interval, method performed such that i. for at least a majority of the electrode-scalp contact events, no electrode of the event enters into the dermis; ii. a duration of each electrode contact event is at most 100 milliseconds; and iii. for each electrode contact event, an electrical current flows between the electrode and the scalp so as to deposit electrode-released ions of a first metal or of a second metal on the scalp, thereby forming a respective metal-ion-deposition island on the user's scalp.

BRIEF DESCRIPTION OF THE DRAWINGS

Some embodiments of the invention are herein described, by way of example only, with reference to the accompanying drawings and/or images. With specific reference now to the drawings and/or images in detail, it is stressed that the particulars shown are by way of example and for purposes of illustrative discussion of embodiments of the invention. In this regard, the description taken with the drawings and/or images makes apparent to those skilled in the art how embodiments of the invention may be practiced.

In the drawings:

FIGS. 6A-6C are illustrations of embodiments of needles and/or needle arrays, in accordance with some embodiments of the invention;

FIGS. 22 and 25 illustrate patterns of metal-ion-deposition on the scalp.

FIGS. 26A-26I, 27A-27I, 28A-28D, 29A-29D, 30A-30C, 31A-31D, 32A-32D, 33, 34A-34B, 35-42 relate to additional embodiments of treating the scalp.

FIGS. 43A-43B describe some experimental results.

DESCRIPTION OF SPECIFIC EMBODIMENTS OF THE INVENTION

Figure 1A:
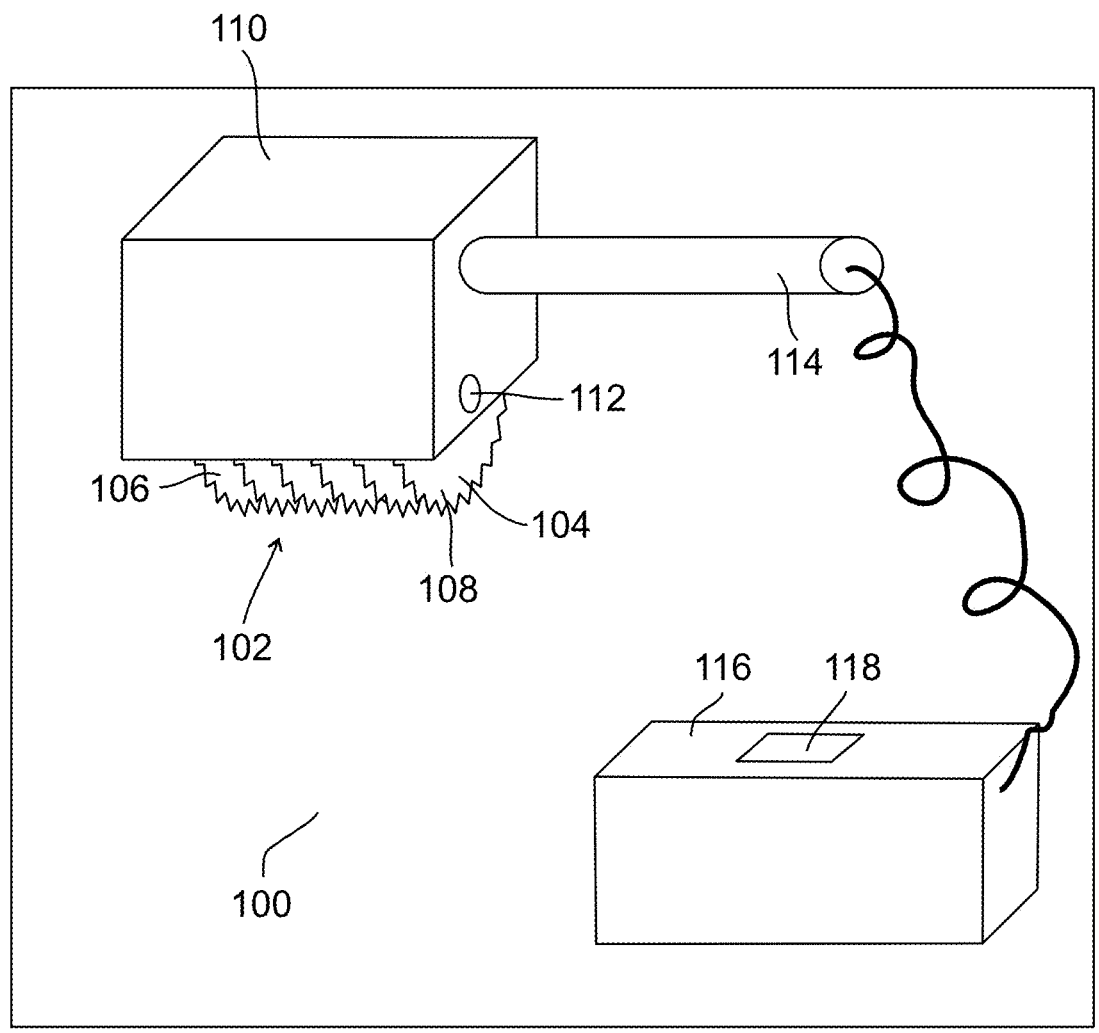
FIG. 1A is an illustration of a device to stimulate hair growth, in accordance with an exemplary embodiment of the invention.

The invention is herein described, by way of example only, with reference to the accompanying drawings. With specific reference now to the drawings in detail, it is stressed that the particulars shown are by way of example and for purposes of illustrative discussion of the preferred embodiments of the exemplary system only and are presented in the cause of providing what is believed to be a useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how several forms of the invention may be embodied in practice and how to make and use the embodiments.

For brevity, some explicit combinations of various features are not explicitly illustrated in the figures and/or described. It is now disclosed that any combination of the method or device features disclosed herein can be combined in any manner—including any combination of features—and any combination of features can be included in any embodiment and/or omitted from any embodiments.

Definitions

For convenience, in the context of the description herein, various terms are presented here. To the extent that definitions are provided, explicitly or implicitly, here or elsewhere in this application, such definitions are understood to be consistent with the usage of the defined terms by those of skill in the pertinent art(s). Furthermore, such definitions are to be construed in the broadest possible sense consistent with such usage.

In the present disclosure 'electrical circuitry' or 'electronic circuitry' is intended broadly to describe any combination of hardware, software and/or firmware.

Electronic circuitry may include may include any executable code module (i.e. stored on a computer-readable medium) and/or firmware and/or hardware element(s) including but not limited to field programmable logic array (FPLA) element(s), hard-wired logic element(s), field programmable gate array (FPGA) element(s), and application-specific integrated circuit (ASIC) element(s). Any instruction set architecture may be used including but not limited to reduced instruction set computer (RISC) architecture and/or complex instruction set computer (CISC) architecture. Electronic circuitry may be located in a single location or distributed among a plurality of locations where various circuitry elements may be in wired or wireless electronic communication with each other.

When metallic-ions are 'released from' an electrode this is in contrast with pre-applying an ion-containing topical agent (e.g. an ion-containing liquid or cream or gel) to the skin and then using an electrode to drive the ions into the skin. When metallic-ions are 'released from', the source of the metallic ions is from the electrode itself. The released metal-ions are provided from an interior of the electrode (e.g. from a reservoir disposed within the electrode) or from actual material of the electrode (i.e. the electrode is at least partially constructed from the metal which is then released) or from an 'integrally-formed' coating on the electrode—i.e. the electrode is pre-coated with the metal so that the metal coating is integrally formed with the electrode and then metal of this coating is released.

When metallic-ions are 'released from' an electrode this is in contrast with pre-applying an ion-containing topical agent (e.g. an ion-containing liquid or cream or gel) to the skin and then using an electrode to drive the ions into the skin. When metallic-ions are 'released from', the source of the metallic ions is from the electrode itself. The released metal-ions are provided from an interior of the electrode (e.g. from a reservoir disposed within the electrode) or from actual material of the electrode (i.e. the electrode is at least partially constructed from the metal which is then released) or from an 'integrally-formed' coating on the electrode—i.e. the electrode is pre-coated with the metal so that the metal coating is integrally formed with the electrode and then metal of this coating is released.

By 'releasing' metallic ions from the electrode rather than relying on a topically-applied ion-containing flowable-fluid (e.g. liquid, cream, gel), it is possible to deliver distinct ion-deposition metal-ion deposition islands. After treatment, small electrical currents may flow between these metal-deposition islands to electrically stimulate the skin after the electrode-contacting events have ceased, thereby providing a sustained effect.

A 'counter-ion' is an ion with a different electrochemical potential relatively to the skin.

Typically, an ion is a 'metal ion.'

A 'Cylindrical Roller' is either continuous—full cylinder—OR a series of discs along a common central axis (straight or conformable) where the circumferences of the discs are substantially disposed along a common 'geometrical-construct' cylinder']

A 'thin disc' having a thickness of at most 1 mm or at most 0.75 mm or at most 0.5 mm or at most 0.25 mm or at most 0.1 mm and/or a diameter of at least 10 mm, or at least 30 mm or at least 40 mm or at least 50 mm or at least 60 mm or at least 70 mm.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

First Set of Embodiments

The present invention, in some embodiments thereof, relates to a device and method for stimulating skin and, more particularly, but not exclusively, to a device and method for directly stimulating the skin below the surface of the scalp.

An aspect of some embodiments of the invention relates to a device and a method for stimulating the skin below the surface, for example to stimulate hair growth. Optionally, the skin is the skin of the scalp. Optionally, the stimulation is directly delivered to the skin, at least to one or more layers below the surface, for example, by needles in-situ. Optionally, at least one stimulation modality is applied to the skin.

In an exemplary embodiment of the invention, stimulating hair growth comprises stimulating new hair growth. Alternatively or additionally, stimulating comprises maintaining the current amount of hair. Alternatively or additionally, stimulating comprises reducing the rate of hair loss. Alternatively or additionally, stimulating comprises enhancing implant success.

In an exemplary embodiment of the invention, the skin below the surface is stimulated by at least one needle, for example the needle piercing the skin and stimulating the skin in-situ below the surface. Optionally, an array of needles is used.

In an exemplary embodiment of the invention, locally delivered ions provide stimulation to the skin. Optionally, the movement of the ions is enhanced during and/or after their delivery beneath the skin. Optionally, the scalp is stimulated to enhance movement of the ions to a level sufficient to cause a biological effect. For example, the scalp is stimulated to enhance movement of the ions to a level exceeding 0.01 nanograms/cm$^2$. For example, an electric field is applied to cause the ions to move more quickly and/or greater distances. Optionally, light, heat and/or another means is applied to cause the ions to move more quickly and/or greater distances. Optionally, the stimulation causes increased blood flow and/or opening of capillaries.

In an exemplary embodiment of the invention, the needles provide mechanical stimulation to the skin, for example by traumatizing and/or wounding the skin. Optionally, the pattern of stimulation is selectable and/or controllable, for example manually by a user and/or automatically by a robot and/or by a user under automatic monitoring and/or guidance.

In an exemplary embodiment of the invention, the needles are shaped to part and/or displace exiting hair on the scalp, for example to allow the needle to penetrate the skin of the scalp covered hair. Optionally, the hairs are pushed into one or more sufficiently wide gaps between the needles. The width of the gap is, for example, at least 2 mm, at least 3 mm, at least 4 mm, or other smaller, intermediate or larger sizes are used. The height of the gap is, for example, at least 2 mm, at least 4 mm, at least 6 mm, at least 10 mm, or other smaller, intermediate or larger heights are used. Non-limiting examples of the arrangement of gaps and/or needles include; bull's eye, clover leaf, alternating rows, checkerboard pattern. Alternatively or additionally, needles and/or groups of needles are individually displaceable along the long axis of the needle, for example, to adjust to a variation in skin surface, for example according to the presence of hairs.

In an exemplary embodiment of the invention, the needles are relatively close together, for example, along one or more regions and/or axes of the array. Needles are spaced, for example, about 0.1 mm apart, about 0.5 mm apart, about 1 mm apart, or other smaller, intermediate or larger distances are used.

In an exemplary embodiment of the invention, the needles penetrate no deeper than the dermis. Optionally, the length of the needle is selected according to the estimated dermis thickness associated with a stage of baldness (e.g., before balding begins, initial stage, advanced stage), for example, as described by Hiroyuki et al, incorporated herein by reference. Needles length is selected to form a wound, for example, about 100 micrometers in depth, about 300 micrometers, about 500 micrometers, about 1000 micrometers, about 1400 micrometers, about 1700 micrometers, or other smaller, intermediate or larger values are used.

In an exemplary embodiment of the invention, the needles are relatively thin. For example, the cross sectional area of the needles forms a wound in the dermis having a cross sectional area of, for example, about 0.00001 mm$^2$, about 0.0001 mm$^2$, about 0.001 mm$^2$, about 0.01 mm$^2$, about 0.1 mm$^2$ about 1 mm$^2$, or other smaller, intermediate or larger values are used.

In an exemplary embodiment of the invention, the needles are inserted into the skin for a relatively short period of time, for example, about 0.01 seconds, about 0.05 seconds, about 0.1 seconds, or other smaller, intermediate or larger values are used.

In an exemplary embodiment of the invention, the array of needles is displaced over the scalp. Optionally, the array is displaced automatically, for example by a motor. Alternatively or additionally, the array is displaced manually, for example by the user. Alternatively, the array of needles is static with respect to the scalp.

In an exemplary embodiment of the invention, stimulation comprises vibrational stimulation, for example vibration of the needles. Optionally, needles are vibrated individually and/or in groups.

In an exemplary embodiment of the invention, needles are vibrated along an axis parallel to the lateral displacement of the needles along the scalp, for example, substantially perpendicular to the long axis. Alternatively or additionally, needles are vibrated along an axis perpendicular to the lateral displacement of the needles. Alternatively or additionally, needles are vibrated in one or more axes, for example omnidirectional. Alternatively or additionally, needles can flex, for example, omnidirectionally.

In some embodiments, needles are vibrated to relatively increase the wound cross section below the surface. Needles are vibrated to increase the size of the wound, for example, to about 2× larger than the cross sectional area of the needles, about 5× larger, about 10× larger, about 20× larger, or other smaller, intermediate or larger dimensions are used.

In an exemplary embodiment of the invention, needles are vibrated along the long axis. Optionally, the peak to peak vibration amplitude comprises of inserting the tip of the needle into the deepest part of the skin and/or removing the needle entirely from the skin. Optionally or additionally, the needles are vibrated once the needles have pierced the skin.

In an exemplary embodiment of the invention, the stimulation comprises applying one or more drugs directly below the skin surface, for example metals to preferably inhibit type I 5-alpha-reductase. Non-limiting examples of metals include copper and/or zinc. Optionally, metals are in ionic form, for example cations.

In an exemplary embodiment of the invention, ions are discharged from the needles, for example during piercing of the skin. Optionally, needles are coupled to the metals, for example coated by the metal.

In an exemplary embodiment of the invention, ions are discharged from the needles by a galvanic cell set-up. Optionally, a power source is electrically connected to at least two needles, wherein each needle is coupled to a different metal (e.g., at least two different types of metals). Alternatively or additionally, the needles are electrically connected without the power source, for example with a conductive wire. Alternatively or additionally, the needles are not directly electrically connected outside the skin, but are connected through the skin itself, for example in a galvanic corrosion set-up.

In an exemplary embodiment of the invention, ions are discharged from the needles by a set-up that does not include a self-defined galvanic cell. Optionally, an electrical power source is electrically connected to at least one needle, wherein the at least one needle is coupled to a metal (e.g., at least one type of metal). For example, the metal comprises sufficient polarity and the power source comprises sufficient voltage to cause ion injection. Optionally, needles are attached to two different metals which are not bridged. For example, a power source separately drives Zn and Cu into the scalp. In some embodiments, the needle is electrically connected without the power source, for example with a conductive wire.

In some embodiments the stimulation is delivered below the skin via an injection without needles. For example, the stimulation is delivered via a jet injection, with the jets optionally formed and/or travel in the air outside the skin. Optionally, the stimulation delivered by injection without needles comprises a cream. Optionally, the stimulation delivered by injection without needles comprises ions. In an exemplary embodiment of the invention, ions are deposited below the scalp by jet injection carried out by at least one jet. For example, one jet injects Zn ions and a second jet injects Cu ions.

In some embodiments, jet injectors are used to speed the process of the delivery of stimulation, for example, ion deposition, optionally in addition to needles, optionally or alternatively with a plurality operating simultaneously, for example, at least 2, 4, 10, 20 or smaller or intermediate or greater number of needles. Optionally or alternatively, the jet injectors form an array of injectors. Optionally or alternatively, the array of jet injectors form an array of injectors comprises jet injectors located close to each other, for example, in rows, columns and/or other formations.

Optionally or alternatively, jet injectors are used to inject other types of ions and/or materials, such as vitamins Optionally, at least some jet contains a different solution from others. Optionally, each jet deposits one type of ions at a specific location.

In some embodiments, the material in the jet is heated to cause micro-burns. Optionally, ions are deposited below the scalp by direct injection using a hollow needle containing ionized solution. In this case, a slower jet speed may be used, for example, just fast enough to exit the needle at a desired volume, but not enough to overpenetrate the skin, if at all.

In some embodiments the stimulation is delivered below the skin via an injection without needles together with stimulation delivered by needles. For example, jet injection delivery augments needle delivery. For example, stimulation may be delivered by an array of jet injectors alternating with needles.

In an exemplary embodiment of the invention, the dose of ions is selectable, for example, per needle. Optionally, the type of ion deposited is selectable, for example by controlling the polarity of the voltage at the needle. Optionally or additionally, the approximate amount (e.g., number) of ions deposited (e.g., per needle) is selectable, for example by controlling and/or calculating the charge passing through the needle.

In an exemplary embodiment of the invention, the stimulation comprises selectively heating areas below the surface of the skin of the scalp. Optionally, heating is sufficient to wound the skin, for example by protein denaturation.

In an exemplary embodiment of the invention, areas of below the skin are stimulated by heated needles piercing the skin. Optionally, the heating by individual and/or groups of needles is selectable and/or controllable. Optionally, the volume of skin wounded around the needle is selectable and/or controllable.

In an exemplary embodiment of the invention, the skin below the surface is heated to a temperature sufficient to induce a wound healing response. For example, to about 50 or 45 degrees Celsius, about 55, about 60, about 70 degrees Celsius, or other smaller, intermediate or larger temperatures or subranges thereof are used. In an exemplary embodiment of the invention, the temperature of the skin below the surface is maintained during heating, for example, by a sufficiently large heat source thermally coupled to the needles.

In an exemplary embodiment of the invention, the stimulation comprises selectively applying voltage gradients and/or currents below the skin surface by the needles. Optionally, a plurality of voltage and/or current patterns are applied. In some embodiments of the invention, voltage gradients (e.g., relative between two needles), for example, are less than 1 volt, less than 3 volt, less than 6 volt, or other smaller, intermediate or larger gradients are used. Optionally, one or more electrodes or a different part of the device (e.g., the handle) serve as reference 0 volt for the applied voltage gradients. In some embodiments of the invention, electrical currents (e.g., total current through all needles at any point in time) are, for example, less than 0.05 mA, less than 0.1 mA, less than 0.2 mA, or other smaller, intermediate or larger values are used. In some embodiments of the invention, the voltage and/or current is alternated at a frequency of, for example, about 10 Hz, about 100 Hz, about 500 Hz, about 1000 Hz, or other smaller, intermediate or larger values are used.

An aspect of some embodiments of the invention relates to a method of stimulating hair growth on a scalp. In an exemplary embodiment of the invention, the method comprises selectively traumatizing the skin below the surface of the scalp. Optionally, selectively traumatizing comprises a non-contiguous pattern of relatively small wounds. For example, about 1 wound per $mm^2$ of scalp, about 5 wounds per $mm^2$ of scalp, about 10 wounds per $mm^2$ of scalp, or other smaller, intermediate or larger numbers of wounds.

In an exemplary embodiment of the invention, the method further comprises selectively applying a vibration during selective traumatization of the skin.

In an exemplary embodiment of the invention, the method further comprises selectively heating the tissue inside and/or surrounding the wounds.

In an exemplary embodiment of the invention, the method further comprises selectively depositing drugs, for example type I 5-alpha-reductase (e.g., metallic ions of copper and/or zinc), in and/or around the wounds.

In an exemplary embodiment of the invention, the method further comprises selectively applying one or more patterns of current and/or voltage inside and/or between wounds.

In an exemplary embodiment of the invention, the method further comprises monitoring the applied treatment, for example by a user against the prescribed treatment. Optionally, the treatment protocol is adjusted according to the monitoring, for example, treatment is intensified, one or more treatment modalities are added and/or removed, treatment is reduced.

In an exemplary embodiment of the invention, one or more treatment protocols and/or needle dimensions and/or needle array arrangement are selected to reduce pain or be painless. Non-limiting examples include; sufficiently thin needles, sufficiently short needles, pricking the skin with the needle during a relatively short period of time. Alternatively, the pain level is tolerable by the patient. Optionally or additionally, bleeding does not occur.

A particular feature of some embodiments of the invention, relates to the ability to replace the array of needles. Optionally, replacement needs are sterile. Optionally or additionally, replacement needs are low cost.

A particular feature of some embodiments of the invention, relates to the ability that the device is easy to handle and/or easy to use at home. Optionally, one or more wheels comprising needles on the outer circumference, are rolled over the scalp. Optionally or additionally, the device is light weight. Optionally or additionally, the device is maneuverable by holding a handle.

A particular feature of some embodiments of the invention, relates to the ability to apply multiple stimulation modalities underneath the surface of the skin. Optionally, the modalities are applied simultaneously. Inventors hypothesize that the multiple stimulation modalities have a synergistic effect, for example, increasing blood flow to the scalp, forming collagen, and/or regenerating hair.

In some embodiments, a plurality of treatments (ion, vibration, light, electricity and/or heat or other methods of stimulation) provides synergistic benefits to the treatments, when performed, for example, at the same time and location. Optionally, a plurality of treatments provides more efficacious results than a series of identical individual treatments. In some cases, applying the same treatments in sequential form would not suffice to provide the minimal stimulation required for healing. In other cases, sequential treatments may require strong and/or long treatments to reach an effective level.

In some embodiments, the synergistic effects include enhanced delivery of stimulation. For example, a plurality of stimulations may improve blood flow. In some embodiments, the combination of treatments is selected so as to increase blood flow beyond that level of blood flow achieved by the use of individual treatments.

In some embodiments, stimulation by ions and by vibration provides synergistic effects. Optionally, stimulation by light and heat provide synergistic effects. Optionally, stimulation by ions, vibration, light, electricity and heat provide synergistic effects. Optionally, stimulation by ions and electricity provide synergistic effects. Optionally, stimulation by ions and light provide synergistic effects. Optionally, stimulation by ions and heat provide synergistic effects. Optionally, other combinations of ions, vibration, light, electricity and/or heat or other methods of stimulation provide synergistic effects.

In some embodiments, the synergistic effects are enhanced by performing a plurality of stimulations in localized areas. Optionally, the synergistic effects create a strong gradient of effects, so degree of total stimulation at one area is greater than degree at a nearby area, possibly causing biological effects in itself. Optionally, the localization of the treatment prevents the dilution of the stimulation effects which may be otherwise caused by "spreading" different stimulation methods over a large area.

Possibly, the localization of the treatment prevents a weakening of the stimulation effects caused by limitations of time, energy and/or other resources. For example, the localization of the treatment may prevent dilution of the stimulation effects which may be caused by a lack of sufficient strength in an electrical field and/or a lack of sufficiently strong heat shock.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Device

FIG. 1A is an illustration of an exemplary device 100 for promoting hair growth, in accordance with an exemplary embodiment of the invention. In an exemplary embodiment of the invention, device 100 applies one or more stimulatory modalities directly to the skin at least below the surface, for example by needles pricking the skin. Optionally, device 100 is used on the skin of the scalp of a patient.

In an exemplary embodiment of the invention, the depth of the needle penetration is controlled, for example, to reach different skin layers, for example, epidermis, dermis, depth of the hair follicle's bulb (e.g., a stem cell rich area), the depth of the hair follicle's papilla (e.g., rich capillary area). Optionally, different needles have different lengths. Alternatively or additionally, the depth of penetration is controlled for example by vibrating the needle. Optionally, different stimulations are applied at different depths and/or skin layers, either simultaneously and/or in parallel. Non-limiting examples include; discharging specific ions at specific targets, heating specific skin layers, causing greater microtrauma at different layers.

In an exemplary embodiment of the invention, needles 102 are arranged along the circumference of at least one disc 104, for example, 2, 4, 6, 8, or other smaller, intermediate or larger numbers of discs 104 are used. The diameter of discs 104 is, for example, about 2 cm, about 4 cm, about 6 cm, or other smaller, intermediate or larger diameters are used. The thickness of discs and/or needles is, for example, about 0.05 mm, about 0.1 mm, about 0.15 mm, or other smaller, intermediate or larger thickness are used.

A potential advantage of the disc design, is that the needle array is low cost and/or easy to replace. Another potential advantage of needles 102 arranged along the circumference of discs 104 is that device 100 can be rolled on the scalp, potentially providing for increased control and/or monitoring of needles 102 piercing the scalp, for example, as will be described in greater detail in the section "Feedback/Monitoring".

Figure 1B:
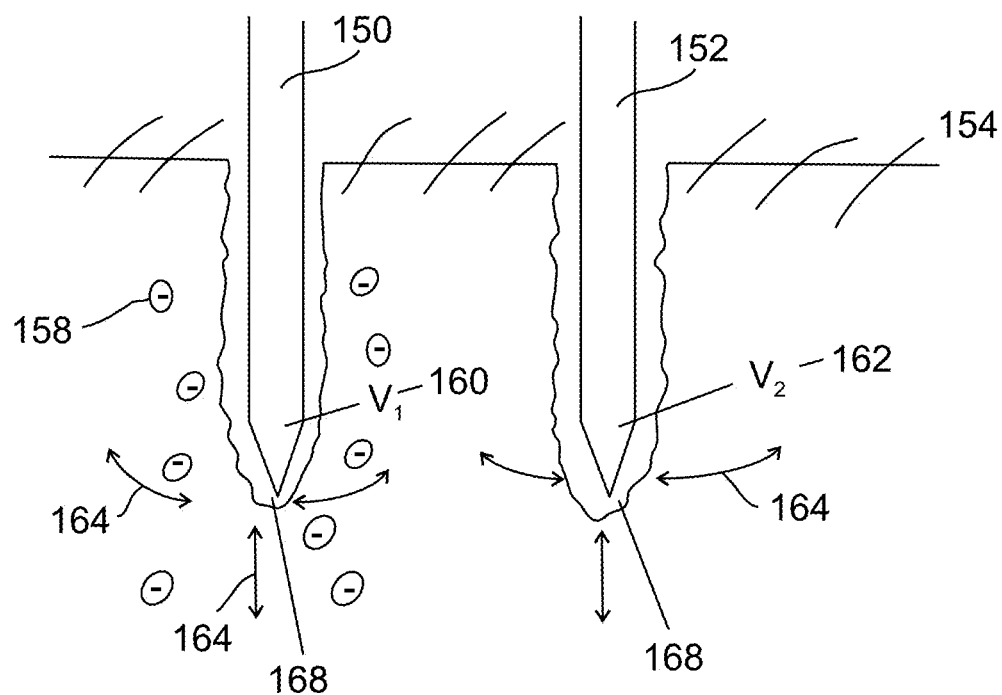
FIGS. 1B and 1C are illustrations of the function of the device, in accordance with an exemplary embodiment of the invention.

In an exemplary embodiment of the invention, needles 102 and/or discs 104 are arranged to allow existing hair on the scalp to be displaced (e.g., brushed) away from the needles during use, for example, as illustrated in FIG. 1B. Optionally, discs 104 are arranged parallel to one another, to allow hair to be brushed between the discs. Discs 104 are located about 1 mm apart, 3 mm apart, about 5 mm apart, or other smaller, intermediate or larger distances are used. A potential advantage is to move hair out of the way of needles 102, such that needles 102 can pierce the skin of the scalp.

In an exemplary embodiment of the invention, needles 102 are coated by at least one metal. Alternatively, needles 102 are made from the metal. Optionally or additionally, discs 104 are coated and/or made from the metal.

In an exemplary embodiment of the invention, the ionic form of the metal is a type I 5-alpha-reductase inhibitor, for example, copper 106 and/or zinc 108. Optionally, alternating discs 104 of copper 106 and zinc 108 are located in parallel. A potential advantage is release of the 5-alpha-reductase inhibitor, for example ions 158, directly into the skin of the scalp during piercing by needles 150 152, for example, as will be described in more detail in the section "5-Alpha-Reductase Inhibitor".

In an exemplary embodiment of the invention, needles 102 are coupled to a housing 110, for example, discs 104 are connected to an axle 112 to provide for rotation of discs 104. Optionally, housing 110 provides housing for discs 104, electrical contacts, heating elements and/or vibration elements.

In an exemplary embodiment of the invention, housing 110 is connected to handle 114. A potential advantage is that device 100 can be manually controlled by the user, for example by being hand-held.

In an exemplary embodiment of the invention, device 100 is light-weight, for example, less than 100 grams, less than 150 grams, less than 250 grams, or other smaller, intermediate or larger weights are used.

In some embodiments of the invention, device 100 is connectable to a base 116. Optionally, base 116 provides a power supply, for example, an alternating voltage and/or current such as from a wall outlet, and/or a direct voltage and/or current for example from a battery (e.g., rechargeable battery). Alternatively or additionally, base 116 provides a communication link to and/or from device 100, for example software to control device 100, and/or data gathered by device 100. Alternatively or additionally, base 116 may include an electronic controller. In some embodiments, at least some functions of base 116 are located in handle 114. For example, handle 114 may include electronics.

In an exemplary embodiment of the invention, device 100 is electrically connected to a user interface 118, for example, LED and/or a screen, for example to provide feedback to the user. Optionally, LEDs with different colors indicate status of device 100, non-limiting examples include; indicating when device 100 is connected to the power supply, indicating when the heating element of device 100 has reached the desired temperature and ready for use, indicating when device 100 is not yet ready for use (e.g., heating element is being heated). Optionally, a screen indicates status of device 100, non-limiting examples include; displaying the current usage (e.g., number of rotations on scalp), displaying the percentage of the treatment and/or dose delivered, warnings, error messages.

FIG. 1B is an illustration of the use of the device, for example device 100 of FIG. 1A, in accordance with an exemplary embodiment of the invention, for example, during the piercing of the scalp. FIG. 1B illustrates needles 150 and 152 (FIG. 1B) (e.g. part of array 102 (FIG. 1A)) piercing scalp 154 (FIG. 1B).

Figure 1C:
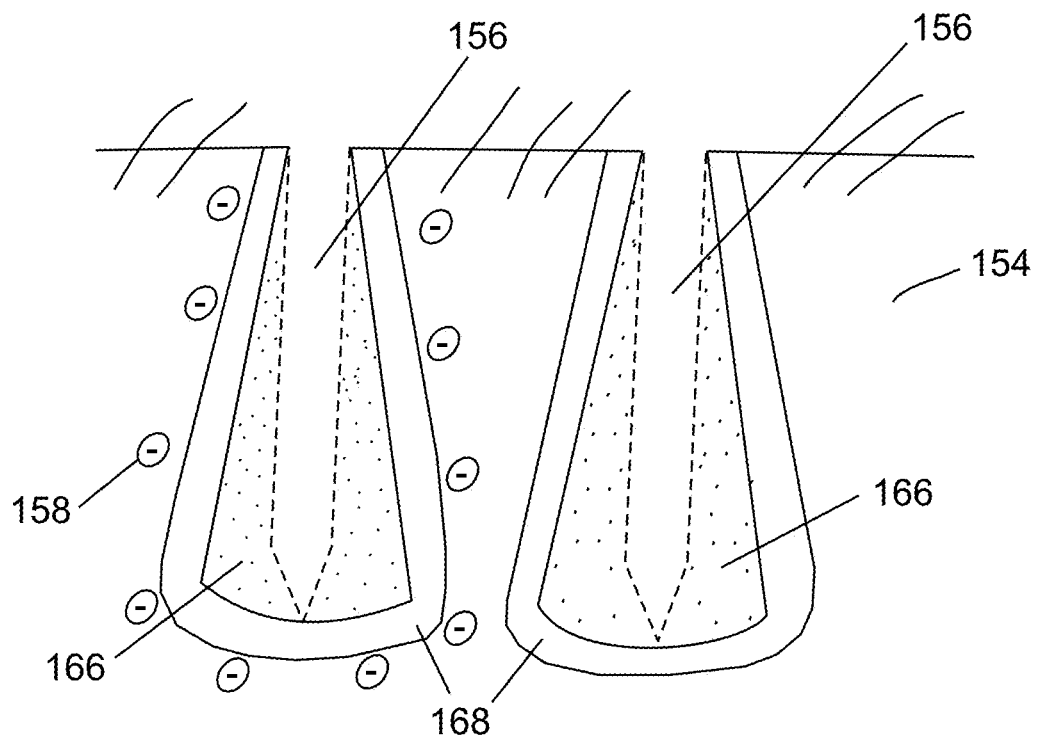

FIG. 1C illustrates scalp 154 after needles 150 and 152 have pierced scalp 154 and have been removed from scalp 154. In an exemplary embodiment of the invention, device comprises an array of needles 102. Needles 150 and 152 pierce scalp 154 forming wounds 156 surrounded by ionized tissue 166. More details about needles are provided herein, for example, in the section "Mechanical Stimulation".

Figure 1D:
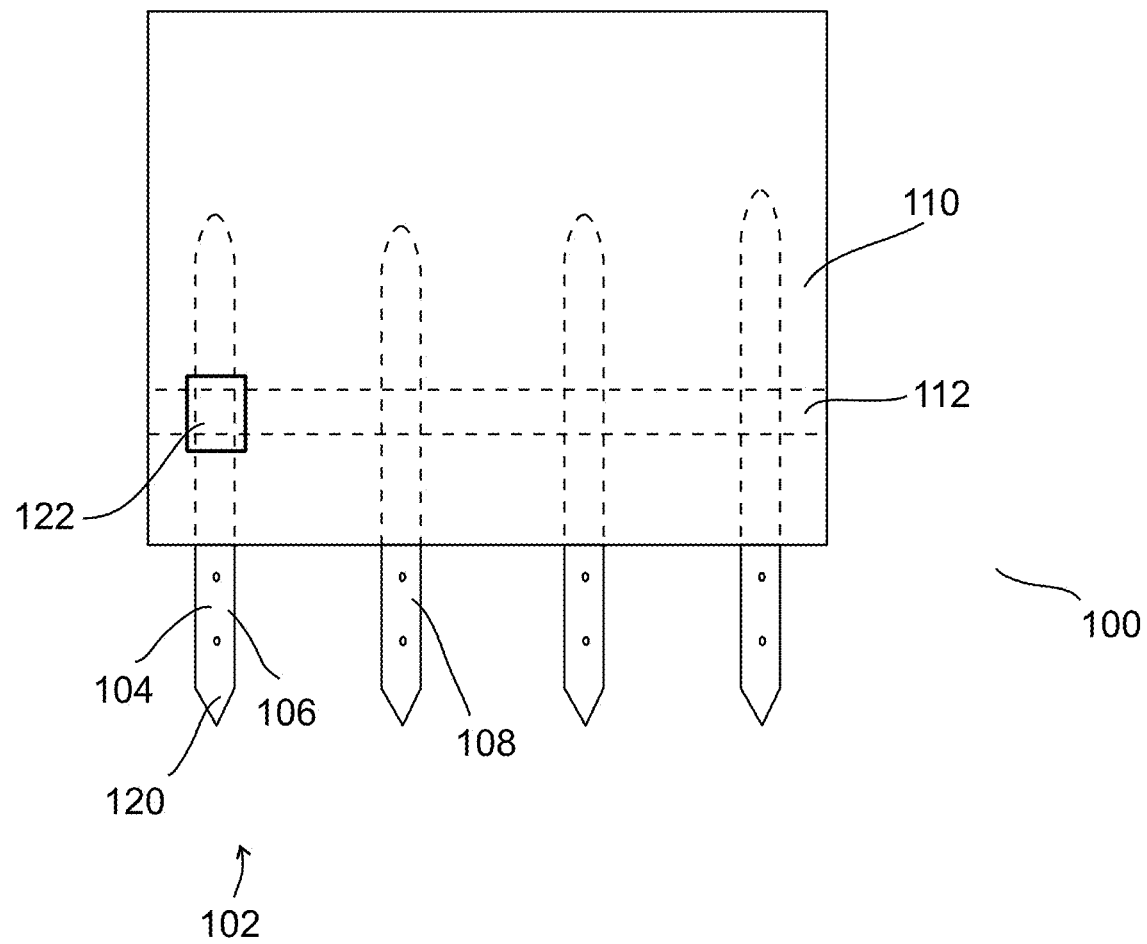
FIG. 1D is a face-on illustration of the device of FIG. 1A, in accordance with an exemplary embodiment of the invention.

FIG. 1D is a 'face-on' view of device 100 of FIG. 1A, in accordance with an exemplary embodiment of the invention.

Figure 2:
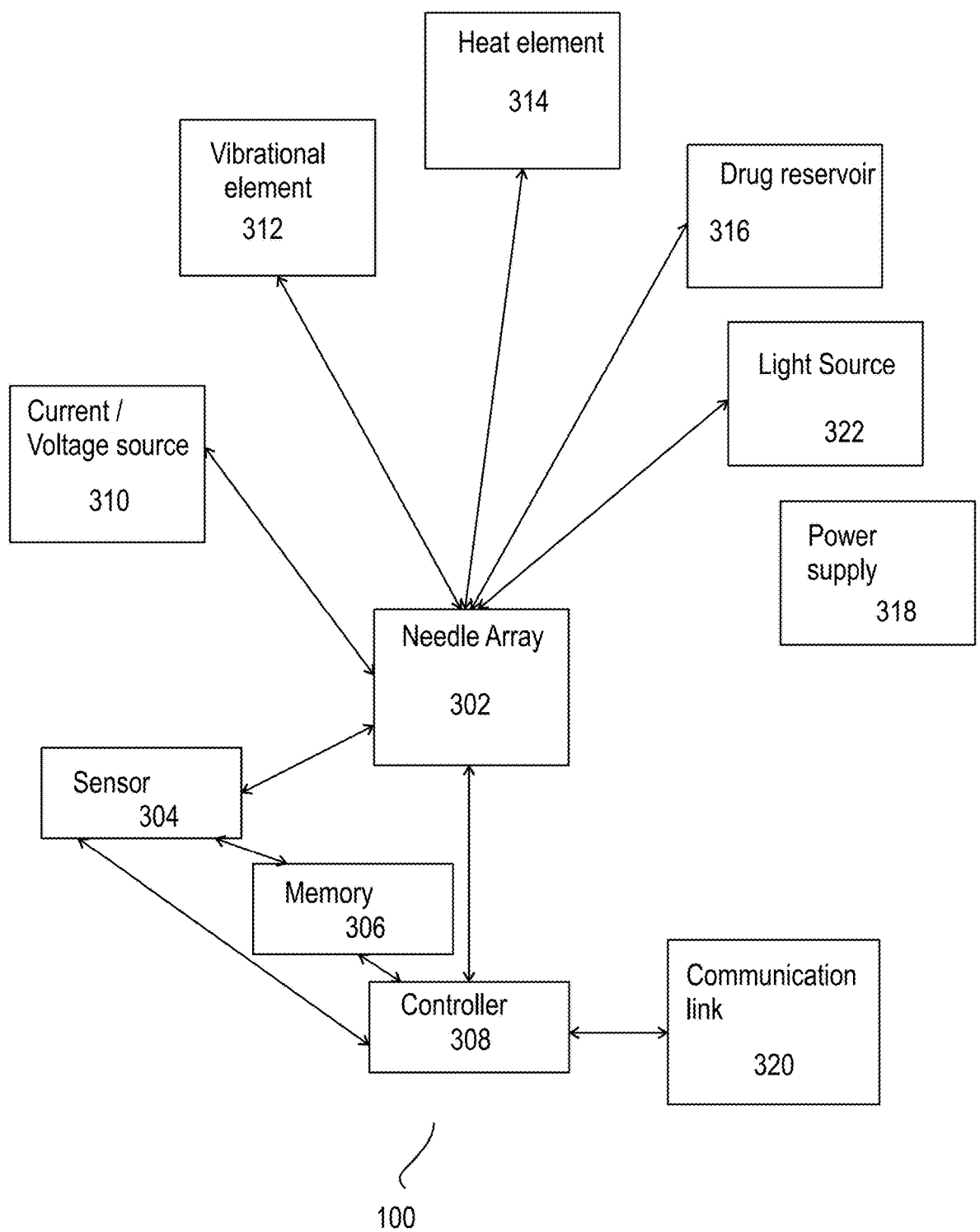
FIG. 2 is a block diagram of the device of FIG. 1, in accordance with an exemplary embodiment of the invention.

FIG. 2 is a block diagram of device 100 of FIG. 1, in accordance with some embodiments of the invention. Additional optional elements are illustrated.

In an exemplary embodiment of the invention, needles 302 (e.g., needles 102 (FIG. 1A)) are coupled to a current and/or voltage source 310, for example located in housing 110 (FIG. 1A). Optionally, springy rods, serving as electrical contacts, contact metallic rings on the axis. Optionally, each ring touches a disk to transmit current. For example, needle 150 is coupled to a first voltage V1 160 (FIG. 1B), and needle 152 is coupled to a second voltage V2 162, forming a voltage gradient in scalp 154. More details will be described, for example, in the section "Electrical Stimulation".

In some embodiments of the invention, needles 302 are coupled to at least one vibrational element 312, for example located in housing 110 (FIG. 1A). For example, needles 150 and 152 (FIG. 1B) are vibrated in one or more directions as illustrated by arrows 164 (FIG. 1B). Vibrations can result in increasing the volume of wound 156, shown by the dotted area. More details will be described for example, in the section "VIBRATION". In some embodiments of the invention, a small DC motor 122 (shown in FIG. 1D) with a mass attached to its axis but a bit off-center vibrates needles 120 (FIG. 1D), for example, providing 2-dimensional vibrations (e.g., omni-directional) perpendicular to the axis of motor 122.

In some embodiments of the invention, needles 102 (FIG. 1A) are coupled to at least one heating element 314 (FIG. 2), for example located in housing 110 (FIG. 1A). For example, needles 150 and 152 (FIG. 1B) heat a volume of tissue 168 in scalp 154. More details will be described in the section "THERMAL STIMULATION".

In some embodiments of the invention, device 100 (FIG. 1A) comprises a drug reservoir 316 (FIG. 2), for example located in housing 110 (FIG. 1A), for example, as will be described with more detail in the section "Adjuvant Treatment".

In some embodiments of the invention, device 100 (FIG. 1A) comprises a light source 322 (FIG. 2), for example, as will be described with more detail in the section "Light Stimulation".

In some embodiments of the invention, device 100 comprises at least one sensor 304, for example located in housing 110. Optionally, sensor 304 detects the position of needle array 302 relative to the scalp, for example, using x and/or y coordinates across the surface of the scalp. Alternatively or additionally, sensor 304 is a temperature sensor to measure the temperature of the scalp. Alternatively or additionally, sensor 304 is an optical sensor to detect changes in skin color. Potentially, measurements of the temperature and/or skin color are used to estimate the inflammatory response and/or increase in blood flow, for example, as a result of treatment.

In some embodiments of the invention, device 100 comprises a controller 308, optionally located in housing 110, for example, as will be described with more detail in the section "Controller".

In some embodiments of the invention, device 100 comprises a memory 306, optionally located in housing 110 and/or accessed by controller 308 and/or sensor 304, for example, as will be described with more detail in the section "Controller".

In some embodiments of the invention, device 100 comprises a communication link 320, for example, to link controller 308 and/or memory 306 with a remotely located processor, non-limiting examples include; a computer, a laptop, a central server for example viewed by operators, a central database (e.g., access through the internet). Optionally, link 320 is wireless, non-limiting examples include; 802.11, blue tooth, wireless cellular phone network. Alternatively or additionally, link 320 is wired.

In some embodiments of the invention, link 320 is used to perform one or more functions, non-limiting examples include; upgrade controller 308 software, download usage data from memory 306, program controller 308 with the prescribed treatment.

In some embodiments of the invention, device 100 comprises a power supply 318. Optionally, power supply 318 is a plug. Alternatively or additionally, power supply 318 comprises one or more batteries, optionally rechargeable. Power supply 318 provides electrical power to one or more of; communication link 320, controller 308, memory 306, sensor 304, current/voltage source 310, vibration element, heat element 314, drug reservoir 316, needle array 302.

In some embodiments of the invention, elements 310, 312, 314, 316 are coupled to array 302, for example to apply a respective stimulatory modality through array 302, for example, underneath the skin surface. Device 100 can be comprised of any combination of elements 310, 312, 314, 316, for example none of the elements, any single element, any two elements, any three elements, or all of the elements.

Figure 3A:
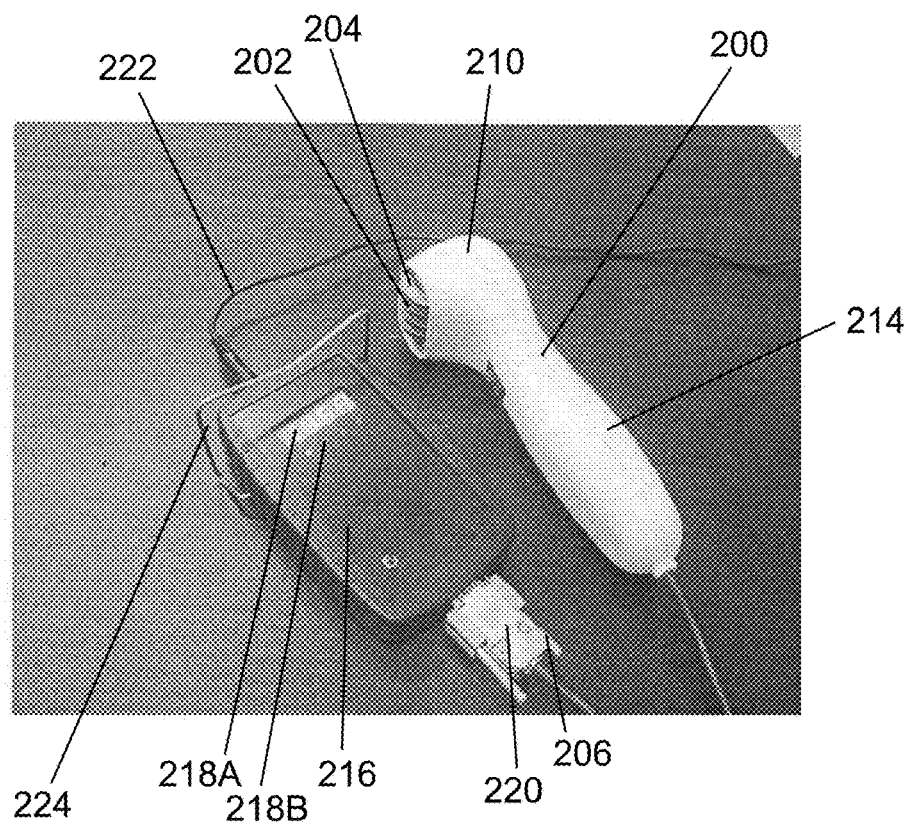
FIGS. 3A-3C are images and illustrations of a prototype device to stimulate hair growth, useful in practicing some embodiments of the invention.
Figure 3B:
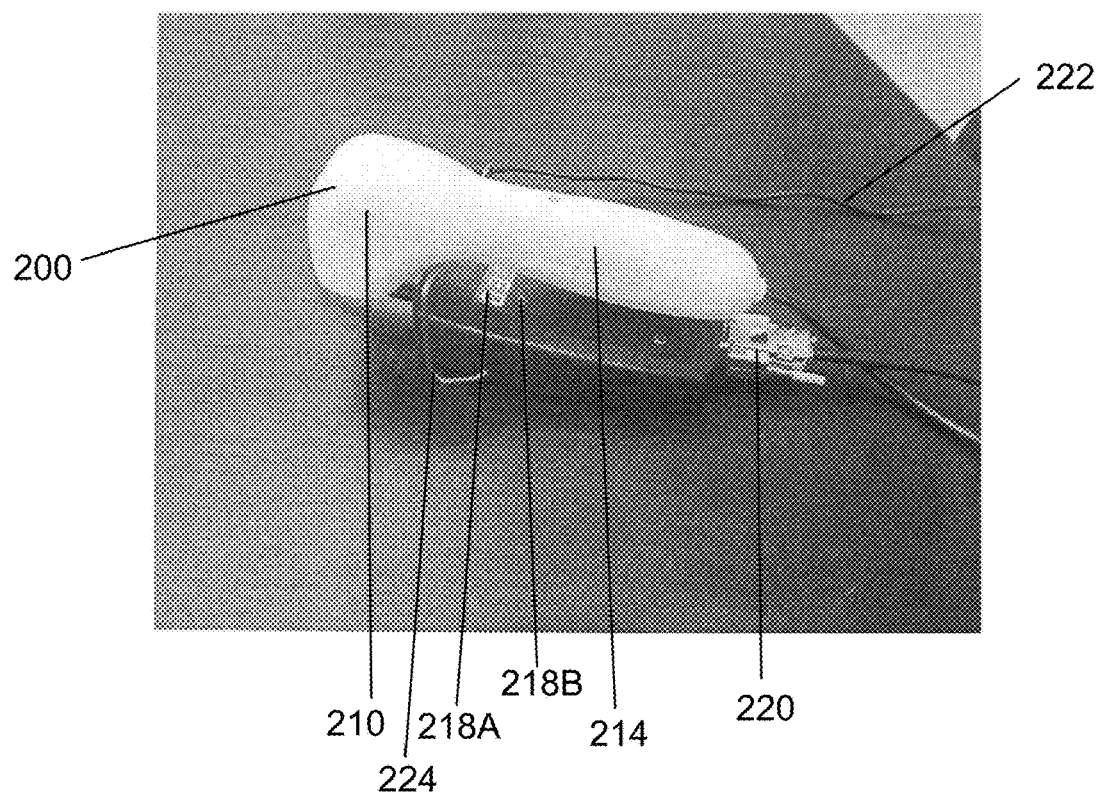

FIGS. 3A and 3B are images of a prototype device 200 to stimulate hair growth, useful for practicing some embodiments of the invention, for example, device 100 of FIG. 1. FIG. 3A is an isometric view of device 200, illustrating for example 8 alternating zinc and copper discs 204, each having needles 202 on the circumference. Optionally, discs 204 are located in housing 210. Optionally, device 200 is held by a handle 214. An optional on/off switch 206 is used to turn device 200 on or off. An optional cable 220 provides a communication link to base 216. An optional numerical display 218A is used to display a variety of data, for example number of rotations of discs 204. Optional color-coded LEDs 218B display state data of the device, for example power, and/or heating of heating element. Optional cable 222 provides power to base 216 and/or device 200. An optional elevated wire 224 attached to base 216 provides for a rest position of device 200, potentially protecting needles 202 from contact damage (as shown in FIG. 3B).

Figure 3C:
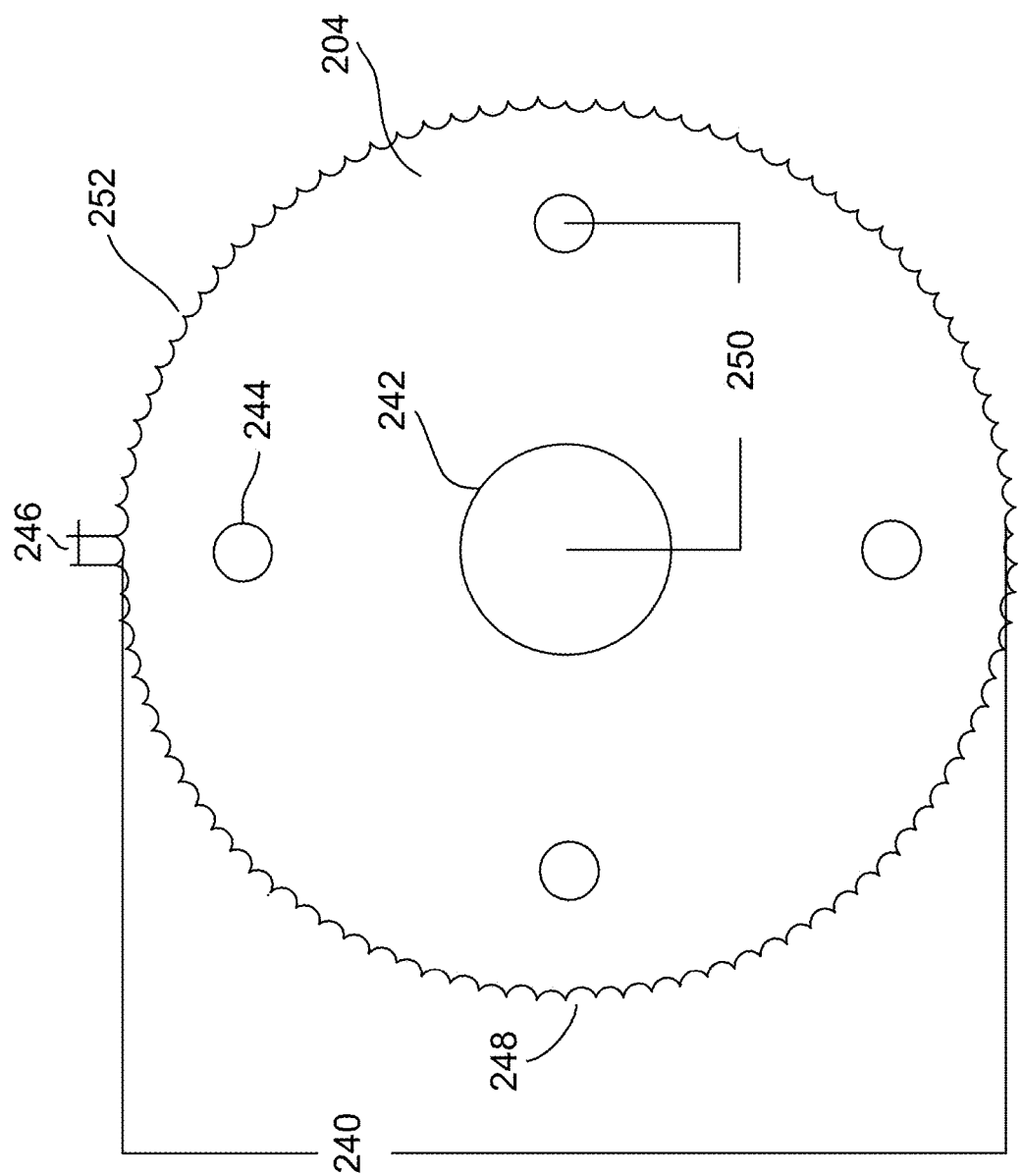

FIG. 3C is an illustration of an exemplary disc, for example disc 204 as used in device 200 of FIGS. 3A-3B, useful for practicing some embodiments of the invention. Thickness of disc 204 (not including the needles) is, for example, about 0.1 mm or 0.07 mm, 0.05 mm, 0.03 mm, 0.13 mm, 0.15 mm, 0.2 mm, or other smaller, intermediate or larger values are used. Optionally, disc 204 thickness is uniform.

In an exemplary embodiment of the invention, one or more needles 252 are located around a circumference of disc 204. Spacing 246 between needles 252 as measured at the tips is, for example, about 1 mm, or 1.5 mm, 1.3 mm, 0.8 mm, 0.6 mm, or other smaller intermediate or larger values are used. Height of needles 248 is, for example, about 0.5 mm, or 0.7 mm, 1 mm, 0.3 mm, 0.1 mm, or other smaller, intermediate or larger values are used. Optionally, needles 252 have a substantially uniform cross section along a length, optionally tapering to a tip. Alternatively needles 252 taper to a tip along the length.

In an exemplary embodiment of the invention, needles 252 are fairly rigid, for example, to pierce the skin. Alternatively, needles 252 are fairly flexible, optionally omnidirectionally, for example, to relatively increase the cross sectional area of the wound beneath the skin.

In some embodiments of the invention, needles are flexible. Optionally, the entire needle is flexible. Alternatively, the portion of the needle piercing the skin is relatively inflexible, and the portion of the needle outside the skin is flexible. Potentially, flexibility slices the skin in unpredictable and/or random movements.

In an exemplary embodiment of the invention, an encoder (e.g. optical encoder) determines the amount of rotation of disc 204. Optionally, light from an LED passing through one or more distal apertures 244, located a distance 250 from the center of disc 204, is sensed by a sensor to determine the degree of rotation. Other types of rotational encoders can also be used, for example, an electrical encoder. Disc 204 has diameter indicated by a reference 240, for example, between 10 and 150 mm.

Overview of Exemplary Method of Treatment

Figure 4:
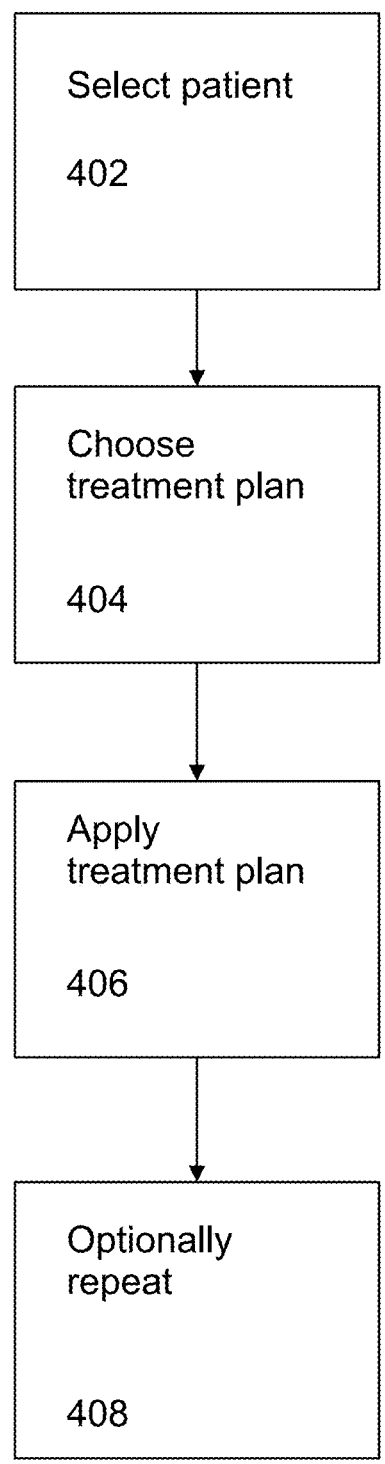
FIG. 4 is a flow chart of a method of stimulating hair growth, in accordance with an exemplary embodiment of the invention.

FIG. 4 is a flowchart of an exemplary method of stimulating scalp hair growth, in accordance with an exemplary embodiment of the invention. Optionally, the method uses the hair stimulation device, for example illustrated with reference to FIG. 1.

Optionally, at 402, a patient is selected, in accordance with an exemplary embodiment of the invention. Optionally, the patient is male. Optionally or additionally, the patient has been diagnosed with androgenic alopecia. Optionally, the patient is at the early stages of hair loss (e.g., has not lost most of his hair).

Optionally, at 404, the treatment plan is selected, in accordance with an exemplary embodiment of the invention. Optionally, a mechanical stimulation protocol is selected. Optionally or additionally, a vibration stimulation protocol is selected. Optionally or additionally, a thermal stimulation protocol is selected. Optionally or additionally, an ion deposition protocol is selected. Optionally or additionally, an electrical stimulation protocol is selected.

In some embodiments of the invention, at least some of the stimulation protocols (e.g., vibration, thermal, ion, electrical) are applied substantially simultaneously. Alternatively or additionally, at least some of the protocols are applied successively, for example, in no particular order. Alternatively or additionally, some protocols are selectively applied, while other protocols are not applied.

In some embodiments of the invention, the treatment plan is selected manually, for example by a physician, for example, based on personal experienced and/or clinical guidelines. Alternatively or additionally, the treatment plan is selected automatically, for example by software, for example, based on collected experimental data.

In some embodiments of the invention, the treatment plan is selected over a long period of time, for example, a single treatment session is to be repeated for a duration of time. For example, a single treatment plan is repeated four times a day, three times a day, twice a day, once a day, every other day, three days a week, twice a week, once a week, or other smaller, intermediate or larger time frames and/or repetition rates are used. For example, treatment is repeated over a month, over two months, over six months, over one year, over two years, indefinitely, or other smaller or intermediate time frames are used. Optionally, treatment is stopped when a desired growth effect is achieved and/or a certain time after, for example, a week or a month. Optionally or alternatively, stimulation is stopped, or at least paused for a week or more, if further progress is not seen. Optionally, the application and/or delay of treatment depends on scalp thickness, with treatment, for example, being continued as long as scalp thickness continues to increase and/or only if an increase is found.

In an exemplary embodiment of the invention, a maintenance level of treatment is defined and followed by the user.

In some embodiments of the invention, the treatment plan is selected so that a different part of the scalp is treated during different treatments. For example, treatment may be twice a day with a different part of the scalp treated during each of the two daily treatments. Optionally, the areas of treatment during different treatment sessions partially overlap.

In some embodiments of the invention, the time per session is selected. For example, about 30 seconds, 1 minute, 2, 4, 6, 10 minutes, or other smaller, intermediate or larger times or subranges thereof are used. Optionally, the time is selected according to a pain level caused by the device and/or a user pain and/or comfort threshold.

In some embodiments of the invention, the treatment area is selected. For example, approximately 50% of the total area in need of treatment, 10%, 25%, 33%, 67%, 75%, 90%, 100% or other smaller, intermediate or larger areas or subranges thereof are used.

At 406, the treatment plan and/or protocol is applied to the patient, in accordance with an exemplary embodiment of the invention. For example, the patient holds the device, and rolls the discs over the area of his scalp that requires stimulation. The needles on the discs prick his scalp according to the mechanical stimulation protocol. Optionally or additionally, the needles are vibrated according to the vibration protocol. Optionally or additionally, the skin is heated underneath the surface (e.g., heat transferred through the needles) according to the thermal stimulation protocol. Optionally or additionally, ions are deposited into below the skin (e.g., released from metallic coating on the needles) according to the ion deposition protocol. Optionally or additionally, electrical current and/or voltages are applied underneath the surface of the skin (e.g., using the needles as electrodes) according to the electrical stimulation protocol.

In a non-limiting example, a protocol comprises of treatments applied 3 times a week, for about 5 minutes per treatment. Each treatment comprises the following stimulations: 5 Volts, at 100 Hz AC, Zinc biased duty cycle, heating to a temperature of 60 degrees Celsius and vibration. Optionally, the protocol is selected according to trial and error, for example, the protocol is adjusted after a couple of weeks depending on the response of the scalp.

Optionally, at 408, the treatment is repeated, for example, according to the plan as in 404, in accordance with an exemplary embodiment of the invention.

Optionally, the same treatment protocol is repeated. Alternatively, the treatment protocol is adjusted. For example, the initial treatment protocol is selected, the treatment is applied, and the treatment is adjusted based on feedback of success of the treatment.

Exemplary Method of Treatment

Figure 5:
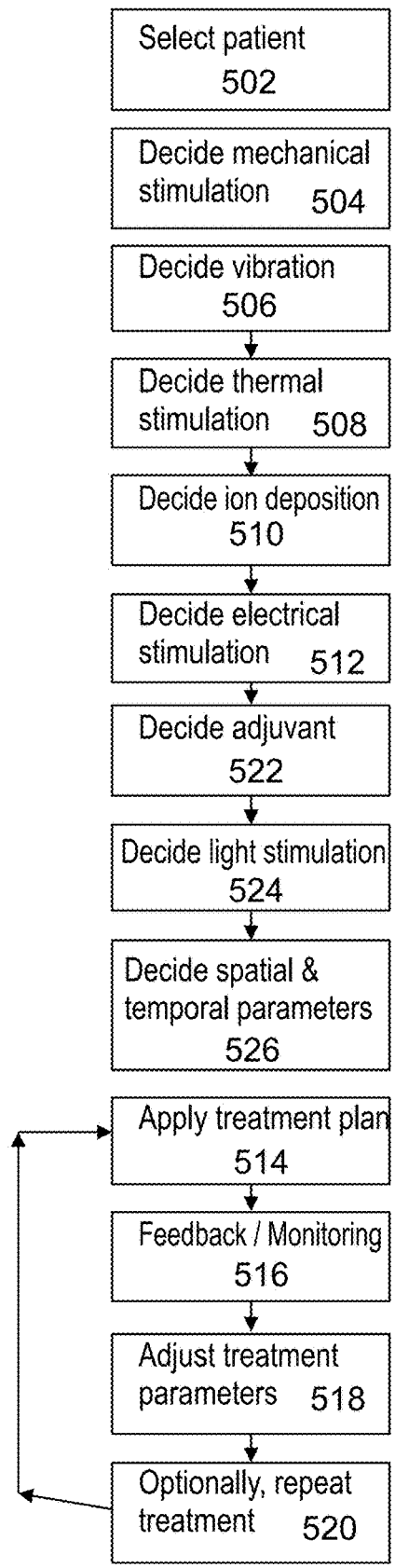
FIG. 5 is a flowchart of a detailed method of FIG. 4, in accordance with an exemplary embodiment of the invention.

FIG. 5 is a detailed method of treatment of FIG. 4, in accordance with an exemplary embodiment of the invention.

Optionally, at 502, a patient is selected for treatment, for example, as will be described in the section "Patient Selection".

Optionally, at 504, a decision is made with regards to the mechanical stimulation protocol, for example, as will be described in the section "Mechanical Stimulation".

Optionally, at 506 a decision is made with regards to the vibration protocol, for example, as will be described in the section "Vibration".

Optionally, at 508 a decision is made with regards to the thermal stimulation protocol, for example, as will be described in the section "Thermal Stimulation".

Optionally, at 510 a decision is made with regards to the ion application protocol, for example, as will be described in the section "Ion Application". Optionally, at 512 a decision is made with regards to the electrical stimulation protocol, for example, as will be described in the section "Electrical Stimulation".

Optionally, at 522 a decision is made with regards to the use of adjuvant treatment, for example, as will be described in the section "Adjuvant Treatment".

Optionally, at 524 a decision is made with regards to the use of light stimulation, for example, as will be described in the section "LIGHT STIMULATION."

Optionally, at 526 a decision is made with regards to the spatial and temporal parameters, for example, as described in the section "Overview Of Exemplary Method Of Treatment" and as will be described in the section "Mechanical Stimulation."

Optionally, at least one of the parameters chosen in steps 504, 506, 508, 510, 512, 522 and 524 are specific per scalp area and are determined individually for each scalp area to be treated. For example, the temple area could receive one treatment and the vertex area could receive a different treatment. For example, it may be determined to treat the vertex area consecutively 5 minutes daily while the temples area is to be treated consecutively 4 minutes daily.

At 514, the treatment plan is applied, for example, as will be described in the section "Apply Treatment".

Optionally, at 516 feedback related to the treatment is obtained, for example, as will be described in the section "Feedback".

Optionally, at 518 one or more variables of one or more treatment protocols are adjusted, for example, as will be described in the section "Adjusting Treatment". Optionally, the adjustment is related to the feedback as in 516.

Optionally, at 520 treatment is repeated, for example, as will be described in the section "Repeat".

Potential Advantages

One or more embodiments have one or more potential advantages:

- A plurality of stimulation modules can create a synergy to stimulate hair growth, for example, through one or more non-limiting mechanisms for example; triggering a wound healing response, inhibiting type I 5-alpha-reductase, electrical stimulation, increasing blood supply to the skin.
- Treatment can be performed at home by the patient, for example when it is convenient for the patient. Treatment is easily repeatable.
- Relatively low cost modality.
- Relatively improved results, for example due to monitoring of the treatment for adherence and/or proper use. Feedback can be provided to the user, for example to guide the user in using the device properly.
- Treatment can be selected to be painless, or to have a tolerable pain level. A potential advantage of pain-free or the tolerable pain level is that the patient is more likely to be compliant with use of the device.
- Anesthesia is not required. For example, use of anesthetizing agents administered by a qualified practitioner is not required (e.g., general anesthesia, local injection of lidocaine).
- Treatment can be selected to not result in bleeding and/or bruising. One or more potential advantages of the reduced inflammatory response and/or bleeding include; relatively increased comfort to the user, preventing a cosmetically unacceptable appearance (e.g., noticeable swelling and/or redness on the head), ability to repeat treatments within relatively shorter durations.

Patient Selection

In an exemplary embodiment of the invention, patients are screened for treatment with the hair stimulation device and/or hair stimulation method.

In an exemplary embodiment of the invention, non-limiting examples of inclusion criteria include; males, diagnosis of androgenic alopecia, relatively early stages of hair loss. Use of the device and/or method is not limited to the described patients, as females can be treated and/or patients can be suffering from other disorders leading to hair loss can be treated.

In an exemplary embodiment of the invention, patients having factors that potentially interfere with treatment are excluded. Non-limiting examples include; genetic and/or inherited metallic ion metabolic disorders (e.g., Menkes disease, Wilson's disease [copper metabolism disorders]), electrically sensitive implanted equipment (e.g., brain stimulation device, pacemakers), use of medication (e.g., 5-alpha-reductase inhibitors for example finasteride for benign prostatic hypertrophy), history of tumors and/or cancer of the scalp and/or prostate.

In an exemplary embodiment of the invention, patients undergo an evaluation by a physician and/or other trained practitioner before treatment begins. Non-limiting examples of the evaluation include; a medical history (e.g., family history of hair loss), a physical exam (e.g., general signs of well being, signs of cancer on scalp, evaluation of amount of hair lost), laboratory tests (e.g., blood tests for copper and/or zinc levels), invasive tests (e.g., biopsy of scalp skin for evaluation).

In an exemplary embodiment of the invention, the physician selects one or more regions on the scalp for treatment. Optionally, all regions will be prescribed the same treatment protocol. Alternatively, different regions will be prescribed different protocols, e.g., if one region experienced more hair loss that another region.

Mechanical Stimulation

In an exemplary embodiment of the invention, the scalp is mechanically stimulated, for example, a mechanical stimulation protocol is selected. The stimulation consists of selectively wounding the areas of skin where hair growth is desired (e.g., micro-trauma), such by one or more needles piercing the skin of the scalp.

Inventors hypothesize that selective wounding of skin on the top of the head (e.g., scalp) will lead to stimulation of hair growth, for example by initiating a wound healing response. Inventors hypothesize that hair will be stimulated through follicle regeneration (e.g., differentiation of stem cells in the skin of the scalp). Inventors hypothesize that sufficiently dense micro-trauma can have an effect of hair follicle regeneration following wound healing similar to that of contiguous trauma. The hypotheses are meant to be non-limiting, embodiments of the invention can still work even if the hypotheses are wrong.

In some embodiments, it may be effective to perform multiple localized treatments, for example, spaced at between 0.1 mm and 4 mm to overcome the over-localization of the skin mechanisms (for example, wound healing occurring in very small areas) and the over-sensitivity to the magnitude of the effect (for example, sensitivity to heat shock). Optionally, the use of multiple localized treatments some treatments, reduces treatment pain. For example, micro-wounding and/or micro-heating may produce less pain than wounding and heating a large area.

In an exemplary embodiment of the invention, the mechanical stimulation protocol comprises one or more variables. Non-limiting examples of selectable parameters include:

Depth of wound: In an exemplary embodiment of the invention, the wound is selected to be no deeper than the dermis layer of the skin of the scalp. Optionally, the wound extends past the epidermis into the dermis. Optionally, the wound is selected to have a depth of, for example, 50 micrometers to 1850 micrometers, or 70 micrometers to 1400 micrometers, or 100 micrometers to 1000 micrometers, or 400 micrometers to 600 micrometers, or other smaller, intermediate or larger ranges are used.

In some embodiments, the wounds are of multiple depths. For example, the wounds are created at depths of about 100 micrometers, about 300 micrometers and/or about 600 micrometers. Optionally, multiple depths are created by, for example, different length needles. Optionally or alternatively, some functions of the device are carried out at the epidermis and other functions are carried out at the dermis. For example, ions of opposing charge could be deposited not only in different locations, but in different depths. Optionally, the different depths enhance the electrical field effect. Alternatively or additionally, the depth of the wound is selected according to patient specific factors, non-limiting examples include; male or female, age of patient, degree of hair loss, for example, according to a table of correlation data values for example described by Hiroyuki et al.

Cross sectional area of individual wound: In an exemplary embodiment of the invention, the cross sectional area of an individual wound is selected to be, for example, about 1 mm$^2$, about 0.1 mm$^2$, about 0.01 mm$^2$, about 0.001 mm$^2$, about 0.0001 mm$^2$, or other smaller, intermediate or larger sizes are used. Alternatively or additionally, the volume of the individual wound is selected, for example, about 0.5 mm$^3$, about 0.3 mm$^3$, about 0.1 mm$^3$, about 0.01 mm$^3$, about 0.005 mm$^3$, or other smaller, intermediate or larger volumes are selected.

Shape of individual wound: In an exemplary embodiment of the invention, the shape of an individual wound is selected, non-limiting examples include; cylinder, cone, pyramid, cross ('+').

Density of wounds: In an exemplary embodiment of the invention, the density of wounds per unit area of scalp to be treated is selected, for example, about 1 wounds/mm$^2$, about 5 wounds/mm$^2$, about 8, wounds/mm$^2$ about 10 wounds/mm$^2$, or other smaller, intermediate or larger densities are used.

Total area of wounding: In an exemplary embodiment of the invention, the area of scalp to be wounded from the total area of the scalp to be treated is selected. The area of wounding is selected to be, for example, about 1%, about 0.1%, about 0.01% of the area to be treated, or other smaller, intermediate or larger values are used.

Gaps between wounds: In an exemplary embodiment of the invention, the distance between wounds is selected. Optionally, the space between wounds along a first axis is selected. Optionally or additionally, the space between wounds along a second axis is selected, for example, the first and second axes are perpendicular to one another. In some embodiments, gaps along at least one axis are selected according to the existing amount of hair at the area to be treated, for example, relatively larger spaces are selected for a region with relative denser hair and/or hair having a relatively larger diameter. Existing hair may be displaced to the gaps between the wounds, so as not to interfere with skin wounding. Spaces between wounds along the first axis are selected to be about, for example, 3 mm, about 4.5 mm, about 6 mm, or other smaller, intermediate or larger spaces are used. Spaces between wounds along the second axis are selected to be, for example, about 0.3 mm, about 0.5 mm, about 1 mm, about 1.5 mm, about 2 mm, or other smaller, intermediate or larger values are used In some embodiments of the invention, the distance between wounds and/or the density of wounds is selected according to the probability of hitting the follicles. Optionally, the density and/or distance between wounds is selected to reduce the probability of damaging follicles. Potentially, the use of optional flexible needles reduces the risk of damage to follicles, for example allowing the skin and/or needle to yield away, escaping puncture.

In an exemplary embodiment of the invention, the wounding profile is selected to have a pain level that can be tolerated by the patient. Optionally, the patient does not experience pain, for example, by sufficiently thin and/or short needles that reduce and/or prevent activation of pain relaying nerves at the skin. Alternatively, the patient experiences minor discomfort.

In an exemplary embodiment of the invention, the wounding profile is selected to initiate a relative minor inflammatory response, for example, relatively minor local edema, erythema and/or swelling that heal immediately, that heal, for example, in less than 5 hours, in less than 12 hours, in less than 1 day, in less than 2 days, in less than 3 days, or other smaller, intermediate or larger time periods are selected.

In an exemplary embodiment of the invention, the wounding profile is selected to not cause bruising (e.g., below skin) and/or bleeding (e.g., above skin). Alternatively, relatively minor bruising and/or bleeding is experienced.

FIG. 6A is an illustration of an exemplary needle 600 used to cause microwounds in the scalp, for example, using embodiments of the needle array of the hair stimulation device as described herein.

Figure 6B:
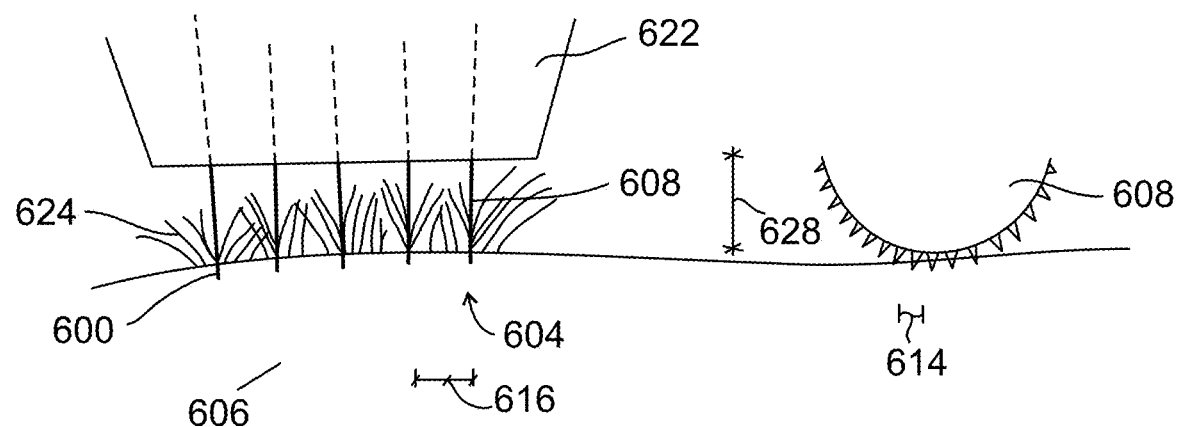

FIG. 6B is a side view of a needle array 604 using needles 600 to cause a pattern of microwounds in the scalp 606.

Figure 6C:
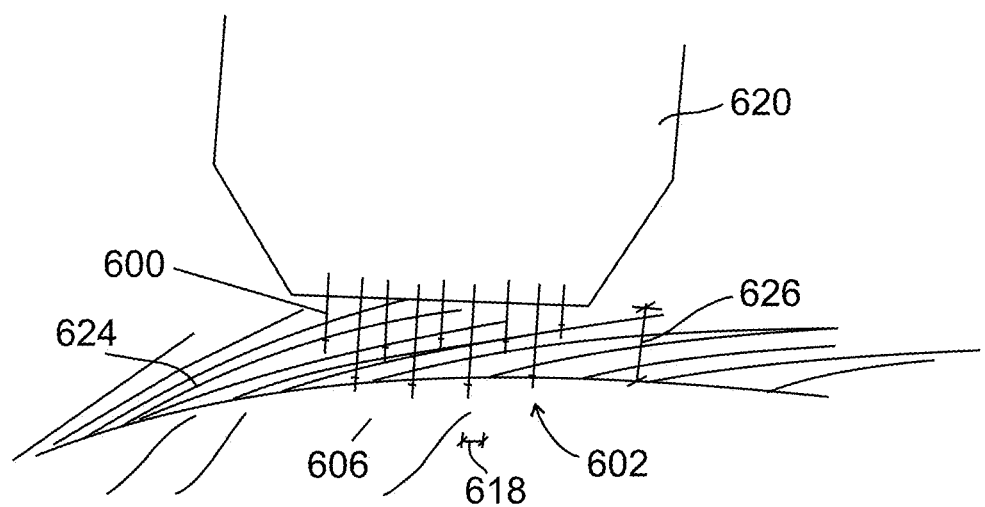

FIG. 6C is a side view of a needle array 602 comprising needles 600 arranged along the circumference of discs 608 (e.g., replaceable and/or disposable). Referring now to FIG. 6A, in an exemplary embodiment of the invention, needles, for example needles 600, are selected and/or arranged as an array according to the selected mechanical stimulation protocol. Non-limiting examples include; a cross sectional diameter 610 corresponding to the selected area of individual wounds, a length 612 corresponding to the selected depth of wound (optionally, a stopper 632, for example a flat disc, is used to set the needle length to prevent the needle from deeper penetration into the skin). Optionally or additionally, some embodiments comprise an array of needles comprising stoppers, each moving up and/or down independently, are used. Optionally or alternatively, some embodiments comprise at least two groups of arrays of needles comprising stoppers, each group moving up and/or down independently. In an exemplary embodiment of the invention, stopper movement is provided by a separate actuator (not shown), for example using a wheel which is parallel to the needle wheel and whose diameter is selectively changed and/or which is moved towards the skin using an eccentric.

In an exemplary embodiment, the actuator moves the needle up and/or down. Optionally, the actuator applies a force to the needle. Optionally, the stopper resists penetration with a force greater than the force of the actuator. Optionally, the resistance of the stopper limits the penetration of the needle. In an exemplary embodiment of the invention, the housing is designed to lean against the scalp. Optionally or alternatively, the wheel itself severs as a stopper to prevent over insertion of a needle.

In some embodiments, a group of needles is attached to a single actuator. Optionally, the combined force resisting penetration is higher than the force of the actuator. In some embodiments, at least one needle comprises a spring. Optionally, the spring helps prevent forceful penetration beyond the stopper's resistance. For example, the needle comprises an electronic spring probe (for example, Spring Contact Probes marketed by Allied Electronics, Inc.). Optionally, the probe structure with a spring acts as a safety mechanism and/or as a method to adhere to non-flat surfaces.

Optionally or additionally, needles are manipulated to result in the selected parameters of the mechanical stimulation protocol, for example, needles are vibrated (e.g., as described in the section "Vibration") to relatively increase the depth and/or cross sectional area of the trauma, needles are repeatedly displaced over the scalp (e.g., rolled back and forth) for example to achieve the desired wound density.

In an exemplary embodiment of the invention, needles 600 have a round cross section (e.g., when taken perpendicular to the long axis). Alternatively, needles 600 can have other cross sectional shapes, for example square, oval, rectangular, square. Optionally, needles 600 have a uniform cross section, tapering to a tip. Alternatively, needles 600 are non-uniform, for example, tapering along the length.

In an exemplary embodiment of the invention, needles 600 of needle array 602 and/or 604 are selected with dimensions corresponding to one or more selected treatment protocol parameters. Non-limiting examples include; needles 600 a space 614 apart along discs 608 and/or discs a space 616 apart, and/or needles 600 a space apart 618 (FIG. 6C) along a first and/or second axis relative to other needles 600, corresponding to the selected gaps between wounds.

In an exemplary embodiment of the invention, a distance 626 and/or 628 between scalp 606 and device head 620 and/or 622 is set to provide a volume for hair 624 during penetration of needles 600 into scalp 606. Hair 624 can be displaced into the volume to let needles 600 pierce scalp 606 to allow the full length of needles 600 to enter. Distance 628 can be set for example, by diameter of discs 608 and/or by selecting the central hinge position within device head 620. Distance 626 can be set for example, by a selection of the total length of needle 600 (e.g., length 612 that forms wound and a region 630 (FIG. 6A) that does not pierce skin of scalp 606 (FIG. 6B)).

In an exemplary embodiment of the invention, the pattern of wounding is parallel straight lines, for example, for a roll of discs 608. Optionally, complex and/or random patterns of wounds can be created by repeated rolling of discs 608 over the scalp. Optionally, one or more discs each comprise multiple needles, arranged, for example, in a circumferential arrangement and/or along the thickness of the wheel, on the surface contacting the skin.

In an exemplary embodiment of the invention, needles 600 are made out of a biocompatible material, non-limiting examples include; metals (e.g., steel, silver, gold), glass, plastic, ceramic.

In an exemplary embodiment of the invention, needles 600 are coated with a type I 5a-reductase inhibitor, for example the metals zinc and/or copper.

Vibration

In an exemplary embodiment of the invention, the scalp is additionally mechanically stimulated by vibration, for example, a vibration protocol is selected. One or more needles for example needles 600 described with reference to FIG. 6A are vibrated, for example, by a vibration element (e.g., actuator) for example element 312 described with reference to FIG. 2. Needles are vibrated at least during piercing of the skin (e.g., when causing microwounds, for example according to the mechanical stimulation protocol).

Inventors hypothesize that vibration of needles during microwounding will lead to stimulation of hair growth, for example, by relatively increasing the wound healing response due to relatively increased wound volumes. Investors hypothesize that vibration can also cause increased blood flow at the wound, for example by massaging the area, leading to relatively increased hair growth due to the higher amount of nutrients available to the hair. The hypotheses are meant to be non-limiting, embodiments of the invention can still work even if the hypotheses are wrong.

In an exemplary embodiment of the invention, the vibration protocol comprises one or more variables. Non-limiting examples of selectable parameters include:

Axis of vibration: In an exemplary embodiment of the invention, needles 600 are vibrated along the long axis of the needle. Alternatively or additionally, needles 600 are vibrated along at least one axis substantially perpendicular to the long axis (e.g., single axis parallel to direction of rolling disc 608, single axis perpendicular to direction of rolling disc 608, omni-directional).

Frequency of vibration: In an exemplary embodiment of the invention, the frequency of vibration of needles 600 is, for example, about 50 Hz, about 70 Hz, about 100 Hz, about 120 Hz, or other smaller, intermediate or larger frequencies are used.

Amplitude of vibration: In an exemplary embodiment of the invention, the amplitude (e.g., peak to peak) of vibration is, for example, about 0.05 mm, about 0.1 mm, about 0.2 mm, or other smaller, intermediate or larger amplitudes are used. Alternatively, the amplitude of vibration is, for example, about 50% of the diameter of the needle, or about 100%, about 200%, or other smaller, intermediate or larger amplitudes are used.

In an exemplary embodiment of the invention, the amplitude of vibration of needles 600 along the long axis is used to control and/or adjust the depth of the wound, for example according to the mechanical stimulation protocol.

In an exemplary embodiment of the invention, the amplitude of vibration of needles 600 along one or more axes perpendicular to the long axis is used to control and/or adjust the volume and/or cross sectional area of individual wounds, for example, according to the mechanical stimulation protocol.

A potential advantage of controlling the vibration is that the selected depth of wound and/or area of individual wounds can be controlled and/or adjusted (e.g., dynamically) without having to replace the needle array.

Needle Actuators

FIGS. 7A-7F are illustrations of embodiments of needle actuators, in accordance with some embodiments of the invention. Optionally, needle actuators act as vibrational elements, to vibrate needles according to the selected vibrational protocol.

In some embodiments of the inventions, one or more non-limiting examples of actuators include; piezoelectric elements, motorized linear actuators, and/or shape memory alloy actuators.

In some embodiments of the invention, needles are individually vibrated. Alternatively or additionally, groups of needles are vibrated together. Optionally, vibration is performed by an off-axis spinning mass, for example, the direction of the axis determines the plane of vibration. For example, translating the movement to a linear direction, pushing on a piston mass creates a linear vibration.

Figure 7A:
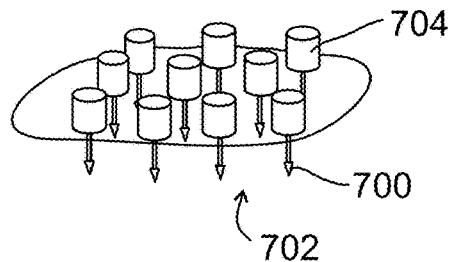
FIGS. 7A-7I are illustrations of embodiments of needle actuators used with needle arrays, in accordance with some embodiments of the invention.
Figure 7B:
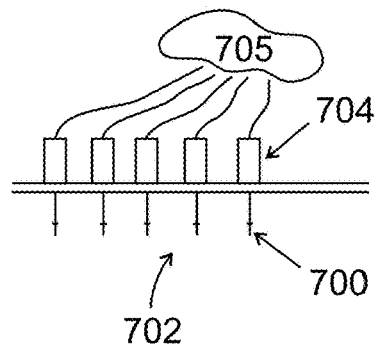

FIG. 7A is an isometric view, and FIG. 7B is a cross sectional view of a needle array 702, for example described with reference to FIG. 6C. Each needle 700 (e.g., as described with reference to FIG. 6A) of array 702 is coupled to an actuator 704. Optionally, each needle 700 is coupled to a separate actuator 704. Optionally, actuators 704 are attached to a power control 705.

Figure 7C:
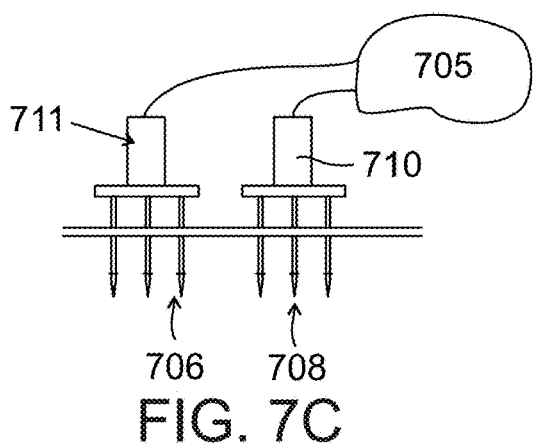
Figure 7D:
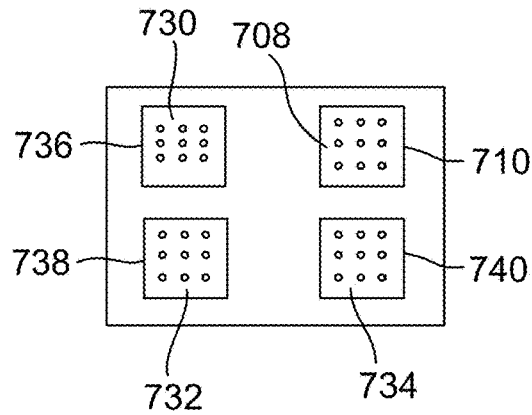

FIG. 7C is an isometric view, and FIG. 7D is a cross sectional view of a needle array 706. Two or more needles are controlled by actuators, for example, array of nine needles 708 is controlled by actuator 710 and, for example, array of needles 706 is controlled by actuator 711. There are two or more groups of needles, for example, four groups 708, 730, 732 and 734 of nine needles in each group are controlled by four actuators 710, 736, 738 and 740.

Figure 7E:
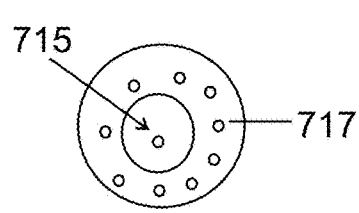
Figure 7F:
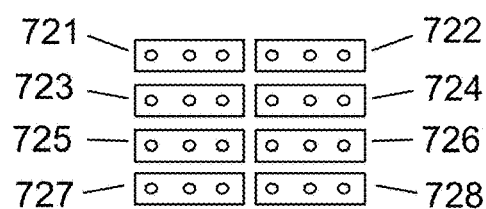

Needle groups can be arranged in a variety of patterns. Non-limiting examples include the checkerboard pattern as illustrated in FIG. 7D, a bull's eye pattern as illustrated in FIG. 7E and/or a side by side tile pattern as illustrated in FIG. 7F. For example, the bull's eye pattern (FIG. 7E) may comprise one needle 715 in an inner circle and at least two needles in needle array 717 in an outer circle and, for example, the side by side tile pattern (FIG. 7F) may comprise eight groups 721, 722, 723, 724, 725, 726, 727 and 728 of needles.

In some embodiments, at least two groups (FIG. 7F) may touch the scalp simultaneously. For example, the device is configured so that several actuators receive a signal to "lower" and touch and/or penetrate the scalp simultaneously. Optionally or alternatively, several needles are connected to a single actuator 710 and go up and down together. Optionally, the needles conform (or are advanced to conform) to the scalp curvature and penetrate together. In some embodiments, the needles are equipped with a spring to facilitate conformity to the scalp curvature.

Figure 7G:
Figure 7H:
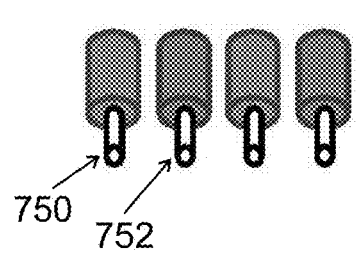

In an exemplary embodiment, 721 and 722 may touch the scalp simultaneously, 722 and 723 may touch the scalp simultaneously, or 723 and 724 may touch the scalp simultaneously, or 724 and 725 may touch the scalp simultaneously, or 725 and 726 may touch the scalp simultaneously, or 721, 722 and 728 may touch the scalp simultaneously, or 722, 725 and 727 may touch the scalp simultaneously or another combination of groups may touch the scalp simultaneously. Optionally, more than two types of ions are discharged from the needles. FIG. 7G is an isometric view of a single injector. Optionally, the injector comprises needle 700. Optionally, needle 700 is coupled to actuator 704. Optionally, actuator 704 comprises a substance to be injected. Optionally, the substance to be injected is ionized Zn solution. Alternatively, the substance to be injected is ionized Cu solution. Alternatively, the substance to be injected is a different ionized solution. Optionally, the injector provides heat. Optionally, the injector provides vibration FIG. 7H is an isometric view of a 1-dimensional array of injectors. Optionally, at least two types of ion solution are contained in the injectors. For example, injector 750 comprises Zn solution. For example, injector 752 comprises Cu solution.

Figure 7I:
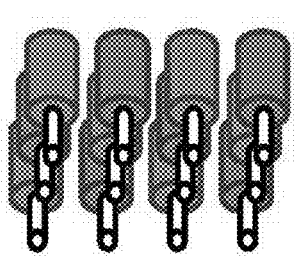

FIG. 7I is an isometric view of a 2-dimensional array of injectors. For example, the array may comprise three rows of four injectors each. Optionally, at least two types of ion solution are contained in the injectors. For example, injectors with actuators shaded with one grey density comprise Zn solution. For example, injectors with a different shown grey density actuators comprise Zn solution.

In some embodiments of the invention, the needle actuation pattern is selected to relatively increase stimulation in certain areas, for example ion injection. Optionally, the pattern is selected according to the follicular density of areas of the scalp. Alternatively or additionally, the pattern is selected to perform different stimulations at different areas simultaneously, with relatively reduced interaction. In some embodiments of the invention, the entire length of the needle enters the actuator, for example during rest (e.g., none vibration mode) and/or during a part of the vibrational phase. A potential advantage is that the device head can be placed against the scalp without piercing the skin.

Potential advantages of vibrating the needle include one or more of:
- Parting hair on the scalp to allow the needle to reach the skin.
- Increasing the life of the needles, for example reducing wear and tear. For example, by changing the axis of vibration every set period of time, different areas of the needle experience wear and tear. Potentially reducing the increased wear caused by vibration.
- Improving electrical contact below the skin surface, for example to relatively improve the application of an electrical current and/or heat transfer.
- Improving mechanical contact and/or electrical contact underneath the skin surface, for example to improve ion injection into the skin (e.g., higher dispersion).
- Increasing the microtrauma mechanical stimulation.
- Reducing pain, for example by reducing the amount of time the needle pierces the skin.

Thermal Stimulation

In an exemplary embodiment of the invention, the scalp is thermally stimulated, for example, a thermal stimulation protocol is selected. The thermal stimulation consists of selectively heating the areas below the surface of the skin where hair growth is desired, such by one or more needles piercing the skin of the scalp, for example, as described herein. The thermal stimulation is selected to cause microtrauma to the skin, for example, by denaturing proteins.

Inventors hypothesize that selective micro-trauma to the skin by heating would induce a positive effect on the scalp skin, for example, thickening the skin, and/or promoting regeneration of degenerated hair follicles and/or new hair follicles. The hypotheses are meant to be non-limiting, embodiments of the invention can still work even if the hypotheses are wrong.

In an exemplary embodiment of the invention, the thermal stimulation protocol comprises one or more variables. Non-limiting examples of selectable parameters include:
- Target temperature of skin: The desired temperature of the skin surrounding the wound, after the area has been heated by the needle. In an exemplary embodiment of the invention, the desired temperature is selected to be, for example, about 40 degrees Celsius, about 50, about 55, about 60, about 70 degrees Celsius, or other smaller, intermediate or larger temperatures are used.
- Volume of heated skin: The dimensions of the resulting micro-trauma due to heating, for example by reaching the target temperature and/or reaching a coagulation temperature (e.g., above 55 degree Celsius). In an exemplary embodiment of the invention, the volume of traumatized skin is selected to be confined to the dermis (e.g., not to extend to the epidermis and/or subcutaneous layers). In an exemplary embodiment of the invention, the thickness of the volume of traumatized skin (across the dermal layer) formed around the needle (e.g., cylinder of skin around needle) is selected, for example, to have a thickness of about 0.01 mm, about 0.05 mm, about 0.1 mm, about 0.2 mm, or other smaller, intermediate or larger thicknesses are used. In some embodiments, the total volume of the skin to be traumatized is selected, for example, to have a volume of about 0.01 mm$^3$, about 0.03 mm$^3$, about 0.05 mm$^3$, or other smaller, intermediate or larger values are used.
- Pattern of heated skin: In some embodiments, not all needles heat the skin. For example, skin may be heated by alternating needles. Alternatively or additionally, different needles heat the skin different amounts.

In an exemplary embodiment of the invention, the volume of skin heated to the target temperature is associated with one or more needle parameters and/or other stimulation protocols, for example, the depth of the needle into the skin, the diameter of the needle, the spaces between needles, the vibrational frequency of the needles (e.g., the amount of time the needle is in contact with the skin) and/or the pattern of needles heating the skin. In some embodiments, the needles and/or other factors are selected according to the selected thermal stimulation protocol. Alternatively, the application of heat to the skin to achieve the desired thermal stimulation protocol is planned according to the selected needle and/or other stimulation protocols.

In an exemplary embodiment of the invention, the volume, pattern and/or target temperature are selected so as to enhance ion and/or medicament transport in desired locations.

In an exemplary embodiment of the invention, needles are thermally coupled to a heat source, for example element 314 as described in FIG. 2. One or more non-limiting examples of heat sources include; resistors (for example heating wires), lamps, light emitting diode (LED), laser. Optionally, the needles are heated inside a chamber for example a cradle until the needle reaches the desired temperature. Alternatively or additionally, the needle is directly heated, for example by internal resistance of the needle itself.

In an exemplary embodiment of the invention, the heat source maintains the temperature of the needle at the desired temperature, for example during pricking of the skin and/or during rest periods.

In an exemplary embodiment of the invention, heat sources are located internally (for example to housing 110), for example, integrated with and/or as a separate part of axle 112 and/or the needles actuators. Alternatively or additionally, heat sources are located externally (for example to housing 110), for example at the lower surface of the housing relatively close to the needle and/or skin surface.

In some embodiments of the invention, heat sources are not thermally coupled to the needles, for example, the heat source (e.g., laser) is used to cause an area of thermal damage independent of the needle piercing the skin.

In an exemplary embodiment of the invention, the heat capacity of the heat source is relatively large compared to the heat capacity of the volume of skin to be heated and/or to the heat capacity of the needles. Optionally, the heat source transfers heat substantially continuously to the needles, for example, during the pricking of the skin by the needles. Optionally, the heat source transfers enough heat to the needles to overcome heat loss for example to the skin, the air and/or the hair (by e.g., radiation and/or conduction).

In an exemplary embodiment of the invention, the needles are made out of a heat conductive material, for example metal.

In an exemplary embodiment of the invention, the heating of the skin by the needles begins to feel uncomfortable if the user stops rolling and/or pricking the scalp. Optionally, the heat transferred to the skin is not sufficient to cause burns beyond the selected heating profile. Removing the device from the skin stops the heat transfer.

A potential advantage of the heat source is that the temperature of the volume of skin to be wounded can be rapidly elevated to the target temperature. Another potential advantage is that the temperature of the volume of skin to be traumatized is maintained at the target temperature for a sufficient length of time to induce the desired wound to the desired volume of skin. A potential advantage of relatively quickly heating relatively small volumes of tissue to the target temperature is preventing and/or reducing pain and/or burns.

5-Alpha-Reductase Inhibitor Deposition

In an exemplary embodiment of the invention, the scalp is stimulated by depositing one or more materials into the skin, for example, an ionic deposition protocol is selected.

In some embodiments, subcutaneous treatment increases ion penetration by accessing ionic channels running through sweat ducts (e.g., Grimnes, *Pathways of Ionic Flow through Human Skin in vivo*), for example, by "hitting" the sweat ducts with the needles, without puncturing the stratum-corneum (SC). At a density estimated at 200-400 glands/cm^2 of skin on the scalp and a diameter of up to 50 micrometers, sweat ducts comprise less than 0.5% of the scalp surface. In some embodiments, the probability of a needle creating ionic current is increased by increasing the contact area of the needles with the scalp, for example, by increasing the cross-section and/or density of the needles. In some embodiments, the probability of a needle creating ionic current is increased by configuring the needles to physically penetrate the sweat ducts through the SC.

In an exemplary embodiment of the invention, the deposited materials have the property of inhibiting the enzyme 5-alpha-reductase. Optionally, type I 5-alpha-reducase is inhibited, for example, selectively inhibited to a greater extent than type II 5-alpha-reducatase.

Without being bound to theory, 5-alpha-reductase is the enzyme which converts testosterone into the potent form dihydrotestosterone. Type I 5-alpha-reductase is expressed mainly in the skin, whereas type II 5-alpha-reductase is expressed mainly in the prostate. Dihydrotestosterone is believed to inhibit hair growth on the scalp. Therefore, inventors hypothesize that selectively depositing ions that inhibit type I 5-alpha-reducase into the skin of the scalp will promote hair growth. However, the efficacy of some embodiments of the invention can be unrelated to the underlying theory, and work even if the theory is incorrect.

In an exemplary embodiment of the invention, the vibration protocol comprises one or more variables. Non-limiting examples of selectable parameters include:

Type of Material: The type I 5-alpha-reductase inhibitor is selected. In an exemplary embodiment of the invention, the type I 5-alpha-reductase inhibitor is one or more types of metals. Optionally, the metal is in ionic form. Optionally, the ions are relatively potent inhibitors. Optionally, the ions are relatively safe for deposition into the skin. Non-limiting examples of ions include copper, zinc, cadmium, nickel and iron. In an exemplary embodiment of the invention, the ions are relatively non-toxic and/or have a relatively higher affinity to type I 5-alpha-reducase, for example, copper and/or zinc. In some embodiments, ions create electrical fields. Optionally, the electric field is created between ions of different electrical potential and/or charge. Optionally, the electric field causes a change in ionic charges in and/or near the skin. Optionally or alternatively, the scalp is enriched with mineral nutrients. For example, the, ions enrich the scalp with micro-elements essential for health. For example, Zn, Cu and/or other elements may contribute to the health of the skin of the scalp. Optionally, avoiding a deficiency in Zn, Cu and/or other elements essential to the health of the scalp may avoid and/or reverse hair growth disorders.

In some embodiments, deficiencies in Zn, Cu and/or other elements essential to the health of the scalp are detected in blood tests. Optionally, additives, for example, ions, are topically administrated, for example by ionic deposition, directly to the scalp. Optionally, additives are administrated to the entire the entire scalp systematically. Optionally, different areas of the scalp are evaluated for their need for health-essential micro-elements. Optionally, additives are topically administrated directly to the area of the scalp requiring them.

Dose: In an exemplary embodiment of the invention, the dosing schedule is selected. The dosing schedule comprises of the concentration of ions and/or number of ions to deposit in the scalp per unit of time (e.g., per needle penetration point, per area of scalp requiring treatment). For example, the dose of zinc is selected to be about 0.001, about 0.01, about 0.1, about 1 nanograms/cm$^2$ per treatment, or other smaller, intermediate or larger values are used. For example, the dose of copper is selected relative to the dose of zinc, for example, about 1%, about 10%, about 50% of the zinc dose. For example, the dose of copper is selected to be about 0.0001, about 0.001, about 0.01, about 0.1 nanograms/cm$^2$ per treatment, or other smaller, intermediate or larger values are used. In an exemplary embodiment of the invention, the number of ions delivered per needle can be controlled by controlling the charge that passes through the needle during the time that the needle pierced the skin, for example, by regulating the time the electrical pulse is turned on and off and/or by controlling the time that the needle is inside the skin.

In an exemplary embodiment of the invention, the cumulative dose (for one or more of the ions) per day is 0.01 nanograms/cm$^2$. Optionally or alternatively, the maximum daily dosage is 0.5 nanograms/cm$^2$. Optionally or alternatively, the cumulative dose per week is 0.02 nanograms/cm$^2$. Optionally or alternatively, the maximum weekly dosage is 3 nanograms/cm$^2$.

In an exemplary embodiment of the invention, the type of ions delivered per needle can be controlled by controlling the voltage of each coated needle.

In an exemplary embodiment of the invention, the ratio between two or more materials (e.g., zinc:copper) injected beneath the skin surface is selected. For example, about 20:1, about 10:1, about 5:1, about 1:1, or other smaller, intermediate or larger ratios are used.

In an exemplary embodiment of the invention, the ionic charge transferred beneath the skin surface is selected (e.g., total charge over the treatment). For example, the total transferred charge is about 5000, about 10 000, about 50 000, about 100 000, about 250 000 nano-Coulombs, or other smaller, intermediate or larger values are used. Non-limiting factors (one or more are selectable) affecting the total charge include; duration of the treatment, the voltage, the type of ions, the number and/or type of needles, the quality of contact between the skin and the needles, needle penetration depth.

In some embodiments, the number of ions deposited during treatment is controlled by adapting the voltage (see, for example, the methods described in Chizmadzhev et al,

*Electrical Properties of Skin at Moderate Voltages: Contribution of Appendageal Macropores*), by adapting the temperature (see, for example, the methods described in Maulsby et al, *The interrelationship between the galvanic skin response, basal resistance, and temperature*), and/or by adapting the frequency. Increasing the voltage, temperature and frequency can each increase the number of ions deposited. For example, the number of ions deposited during treatment is controlled in an open loop manner by determining the voltage before beginning treatment. Alternatively, the number of ions deposited during treatment is controlled in a closed loop manner by determining the voltage during the treatment based on feedback received from sensors incorporated into the device.

In some embodiments, controlling the ions deposited is done directly by measuring the charge of each polarity (ion type), for example, by measuring and integrating the current passed through each type of disk set. The existence of current indicates the unit is in actual use. A degradation of current indicates a faulty unit, improper contact, or other means. Excessive current might indicate a faulty unit, or excessive moisture on the scalp (and therefore not enough current through the scalp).

In some embodiments, the mass of metal ions discharged from the electrodes may be calculated by a formula. For example, assuming the charge C is ionic, and the oxidation state Z, the mass m of metal ions discharged from the electrodes (w is the atomic mass, e the electron's charge, Na is Avogadro's number) is computed as follows:

$$m = \frac{C \cdot w}{e \cdot Z \cdot N_a}$$

In some embodiments, ion injecting electrodes that touch the scalp are connected to one terminal of a power source and an electrode that does not touch the scalp is connected to a second terminal of the power source. For example, the electrode that does not touch the scalp may be connected to a part of the body other than the scalp. For example, the device may comprise a handle comprising an electrode designed to touch the palm of a person holding the handle.

In some embodiments, the efficiency of the deposition of ions is enhanced, for all users or for a specific user, by performing a "calibration phase" in which the same region is treated for a period of a time while changing each parameter slightly and measuring the real-time response in current. Optionally, different treatment parameters may be chosen for different scalp areas of same user. Optionally, different treatment parameters may be chosen for different users.

In some embodiments, the efficiency of the deposition of ions is enhanced through general improvements in the parameters, for example, preparing a better cross section of the needles and/or starting with more efficient voltage and frequency. Optionally, the efficiency of the deposition of ions is enhanced through dynamic modification of changeable treatment parameters through closed-loop feedback/control.

In some embodiments, ion penetration increases blood flow when the electrical fields generated by the small charge deposits create a MENS (microcurrent electrical neuromuscular stimulation) effect in the skin. Optionally, the MENS effect shortens skin healing times. Optionally, the electrical fields invigorate movement of essential ions and stimulate the skin systems into an increased rate of activity.

Figure 8A:
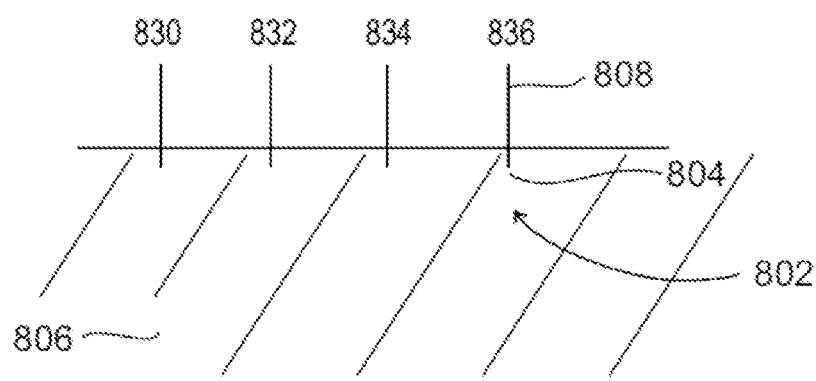
FIGS. 8A-8D are illustrations of embodiments of depositing ions below the skin surface, in accordance with some embodiments of the invention.

FIG. 8A is an illustration of an array of needles 802 depositing materials 804 beneath the skin 806 surface of scalp, in accordance with an exemplary embodiment of the invention. For simplicity purposes, array 802 comprises four needles 808, having the material 804 to deposit located at the part of the needle 808 that pierces scalp 806.

In an exemplary embodiment of the invention, needles 808 are made of material 804. Alternatively, needles 808 are coated with material 804. Optionally or alternatively, 830, 832, 834 and/or 836 represent electrical potentials which may exist on needles 808.

In an exemplary embodiment of the invention, two different needles 808 to be electrically coupled have two different materials 804 at their ends. For example, alternating discs (e.g., as illustrated in FIG. 1) are made from different materials, for example, copper and zinc.

In some embodiments, scalp 806 acts as a bridge, placing two needles having dissimilar metals in electrical contact. The metals can undergo galvanic corrosion, where one metal dissolves in scalp 806, while the other metal absorbs ions from scalp 806. For example, if one metal is zinc and the other metal is copper, the zinc will dissolve and the copper will accumulate. Optionally, material 804 is chosen to have other depositing effects. Optionally or additionally, current is forced in the opposite direction.

Figure 8B:
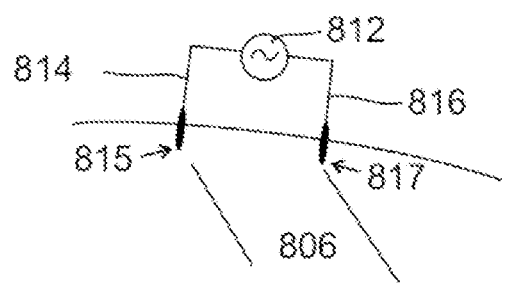

FIG. 8B is an illustration of ion deposition into scalp 806 for example using a galvanic cell set-up, in accordance with an exemplary embodiment of the invention. Optionally, a power source 812 (e.g., source 310 as described with reference to FIG. 2) electrically couples a first needle 814 and a second needle 816. For example, each needle 814 and 816 may have coated electrodes comprising different materials at the piercing ends 815 and 817, for example, needle 814 pierces scalp 806 at piercing end 815 with zinc and needle 816 at piercing end 817 with copper. Optionally, power source 812 emits Alternating Current (AC). Optionally, power source 812 emits Direct Current (DC).

Figure 8C:
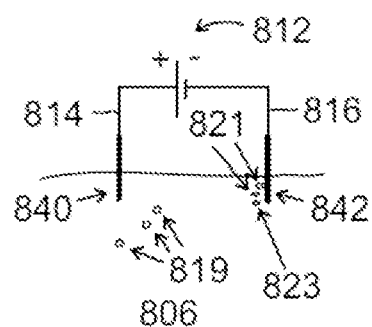

FIG. 8C is an illustration of using the set-up as in FIG. 8B to release zinc ions into scalp 806, in accordance with an exemplary embodiment of the invention. The positive pole of power source 812 is electrically connected to needle 814 with zinc (e.g., acting as the anode 840), and the negative pole is electrically connected to needle 816 with copper (e.g., acting as the cathode 842). Zinc ions 819 are discharged from needle 814 into scalp 806, and copper ions 821 and/or other ions 823 are accumulated from scalp 806 onto needle 816.

In an exemplary embodiment of the invention, the voltage of power source 812 as in FIG. 8C is, for example, about 1V, about 3V, about 5V, about 7V, about 10V, or other smaller, intermediate or larger values are used.

Figure 8D:
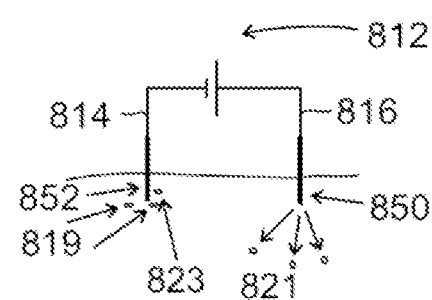

FIG. 8D is an illustration of using the set-up of FIG. 8B to release copper ions into scalp 806, in accordance with an exemplary embodiment of the invention. The positive pole of power source 812 is electrically connected to needle 816 with copper (e.g., acting as the anode 850), and the negative pole is electrically connected to needle 814 with zinc (e.g., acting as the cathode 852). Copper ions 821 are discharged from needle 816 into scalp 806, and zinc ions 819 and/or other ions 823 are accumulated from scalp 806 onto needle 814.

In an exemplary embodiment of the invention, the voltage of power source 812 as in FIG. 8D is at least greater than the standard potential for the reaction, for example, above 1.10 Volt.

In an exemplary embodiment of the invention, power source 812 is an alternating current source. The frequency of source 812 can be selected to result in a desired ion deposition pattern, for example alternating between the set-ups as described in FIGS. 8C and 8D. For example, the frequency of source 812 is selected to be substantially half of the rate of needle pricks per second, for example when using the hair stimulation device with rolling discs, for example, as described with reference to FIG. 1. For example, if the device is rolled over the scalp to achieve a rate of skin pricks of 30 pricks per second and the frequency of source 812 is 15 Hz, the ions deposited during each needle prick will alternate, for example between copper and zinc. Furthermore, different ions will be deposited at different locations.

In some embodiments of the invention, the AC waveform (e.g., duty cycle) is selected according to the ratio of the desired material deposition. For example, to achieve a 10:1 ratio (e.g., of zinc:copper), a waveform having a 10:1 ratio (91% duty cycle) is selected. Alternatively or additionally, the number of needles coated with each material is selected according to the desired deposition ratio, for example, the number of needles coated with zinc relative to the number of needles coated with copper is 10:1.

In some embodiments of the invention, power source 812 is a direct current source. The polarity of source 812 can be selected to result in a desired ion type and/or deposition pattern. For example, according to the set-ups of FIGS. 8C and/or 8D. The set-up of FIG. 8C can also be achieved without source 812, for example by electrically connecting needle 814 and 816.

In an exemplary embodiment of the invention, ions are deposited below the scalp by jet injection carried out by at least one jet. Jet injection is a widely available technology (for example, Taberner et al, *Needle-free jet injection using real-time controlled linear Lorentz-force actuators*, The Medical Jet Injector marketed by AMI (Advanced Meditech International), Inc; Rhodes, *Shallow Dermal Delivery of Vaccines Using Jet Injectors*) and may be adapted for use with the instant application, in accordance with some embodiments of the invention.

In an exemplary embodiment of the invention, one jet injects Zn ions and a second jet injects Cu ions. Optionally, additional jet injectors are used to speed the process of ion deposition. Optionally or alternatively, additional or alternative jets are used to inject other types of ions. Optionally, each jet injector contains a different solution. Optionally, each jet injector deposits one type of ion solution at a specific location.

In some embodiments, materials are injected in controlled small distances between points of entry. Optionally, the injectors are configured on a flat plane, or on a rounded surface that rolls along the scalp.

In some embodiments, multiple-material injectors known in the art (for example, U.S. Pat. No. 8,048,019 to Nisato et al) inject multiple materials at the same location. Optionally, the material in the jet is heated, for example, to between 55 and 65 degrees Celsius or higher) to cause micro-burns.

In some embodiments, ions are deposited below the scalp by direct injection using a hollow needle containing ionized solution.

In some embodiments of the invention, materials (e.g., ions) are added directly to the scalp, for example in the form of a lotion, gel and/or water. Non-limiting examples of ions in this form include $ZnSO_4$, $CuSO_4$. The lotion can be added in addition to the use of coated needles, or instead of coated needles (e.g., using uncoated needles). Optionally, the ions penetrate below the surface of the skin due to piercing and/or vibration of the needles. Alternatively or additionally, the ions penetrate the skin due to an iontophoretic effect created by the electrical charges on the needles.

Electrical Stimulation

In an exemplary embodiment of the invention, the scalp is stimulated by applying one or more currents and/or voltages to areas of the skin, for example, an electrical stimulation protocol is selected. Optionally, a plurality of currents and/or voltages are applied to the scalp, for example different voltages and/or currents to different areas and/or between different needles.

In an exemplary embodiment of the invention, the electrical stimulation is separate from the current applied to the needles to release ions, for example, as described with reference to the section "5-ALPHA-REDUCTASE INHIBITOR DEPOSITION". Optionally, electrical stimulation is applied by one or more discs and/or needles, and ion deposition is applied by different discs and/or needles. Optionally, the needles to apply electrical stimulation but not ion deposition are inert, for example, made from platinum. Alternatively, a voltage is applied to the needles to prevent ion deposition by the galvanic effect. Alternatively or additionally, electrical stimulation and ion deposition overlap, for example, applied by the same discs and/or needles.

Inventors hypothesize that selectively applying a plurality of electrical stimulation patterns (e.g., voltages and/or currents) to the scalp will promote hair growth. However, the efficacy of some embodiments of the invention can be unrelated to the underlying theory, and work even if the theory is incorrect.

In an exemplary embodiment of the invention, the electrical stimulation protocol comprises one or more variables. Non-limiting examples of selectable parameters include:

Geometric voltage and/or current distribution pattern: The pattern of applied voltages and/or current per needle. For example, the voltage and/or current at each needle is independently controlled and/or groups of needles have similar voltages and/or current (e.g., alternating needles have similar voltages and/or currents, needles having the same type of material (for example zinc or copper) have similar voltages and/or currents).

In some embodiments of the invention, the voltage and/or current pattern is substantially the same, for example, the same needle is associated with the same charge and/or current. Alternatively or additionally, the voltage and/or current pattern is dynamic, for example dynamic throughout the array, and/or a region of the array. For example, in a relatively large array, a relatively small patch of the electrical pattern can be scanned across the array.

A potential advantage of two groups of needles with different voltages is the controlled patterning of current and/or ion deposition. For example, local stimulation may be superior to global. Potentially, division to several groups allows greater flexibility and/or controllability of the current. For example, current can be applied (e.g., to different groups, at different intensities) simultaneously or in a time-divided manner Voltage and/or current distribution pattern over time: The pattern of applied voltage and/or current per needle can vary over time. For example, an alternating current and/or voltage can be applied to vary the voltage and/or current between two or more needles (or groups of needles). In the case of using the device with discs for example in FIG. 1 (e.g., rolling the discs with needles on the scalp), selecting an alternating frequency that is less than the frequency of rotation can result in increasing the diversity and/or gradients of voltages and/or currents applied underneath the skin surface. Inventors hypothesize that applying various patterns of voltage and currents to the skin stimulates hair growth. Potentially, applying varying time and/or location stimulations improves stimulation of local points, for example hair follicles Direct current (DC) offset: A voltage offset can be applied to the pattern applied to one or more needles. In an exemplary embodiment of the invention, the DC offset is calibrated, for example, from −3 volts to +3 volts, or other smaller, intermediate or larger values are used. In an exemplary embodiment of the invention, the DC disc to disc relative voltage ranges, for example, from 0 to 6 volt, or other smaller, intermediate or larger values are used.

Alternating current (AC) peak to peak voltage: In an exemplary embodiment of the invention, the peak to peak voltage of the AC varies, for example, from −3 volts to +3 volts, or other smaller, intermediate or larger values are used.

Frequency of AC: In an exemplary embodiment of the invention, the frequency of AC ranges, for example, from 10-1000 Hz, or other smaller intermediate or larger values are used.

Waveform of AC: In an exemplary of the invention, the waveform of AC is rectangular. Alternatively, other waveforms are used, non-limiting examples include sinusoidal, triangular, sawtooth.

Current: In an exemplary embodiment of the invention, the total electrical current is less, for example, than 0.5, less than 1, less than 2 milliAmperes, or other smaller, intermediate or larger values are used.

Adjuvant Treatment

In an exemplary embodiment of the invention, the scalp is stimulated by applying one or more adjuvant treatments. Optionally, at least one drug is applied to the skin.

Figure 9:
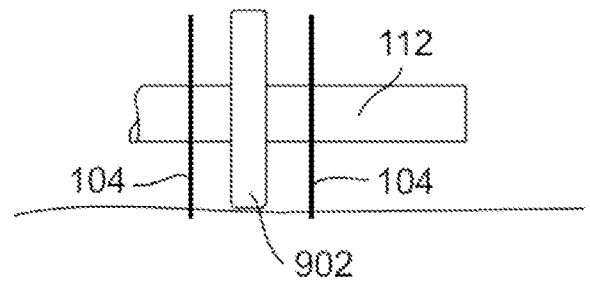
FIG. 9 is an illustration of the device of FIG. 1 further comprising a mechanism for delivering drugs to below the skin surface, in accordance with some embodiments of the invention.

FIG. 9 is an illustration of the device of FIG. 1 further comprising a mechanism for delivering drugs to the skin, in accordance with some embodiments of the invention.

In some embodiments of the invention, at least one drug dispensing mechanism deposits drugs to the skin (e.g., to the surface of the skin, below the surface of the skin).

In some embodiments of the invention, a sponge 902 is used as the drug dispensing mechanism. Optionally, sponge 902 is soaked with the drug to apply to the skin.

In some embodiments of the invention, sponge 902 is in contact with scalp 904. Optionally, sponge 902 is disc shaped, for example having dimensions similar to discs 104. Optionally, sponge 902 is connected to axis 112 similar to discs 104. Optionally, sponge 902 is rolled over scalp 904 together with discs 104. Optionally, sponge 902 is located between discs 104. Optionally, sponge 902 is located between needles. Optionally, sponge 902 is located between discs 104 and needles.

In some embodiments of the invention, two or more sponges are used. Each sponge contains an inactive form of the drug. When the sponges release their drugs into the skin, the drugs react in the skin. A non-limiting example includes one sponge applying a sodium bicarbonate solution to the skin, and another sponge applying an acid for example lemon juice to the skin. The acid and base react in the scalp. Potentially, the reaction of the two solutions pushes out oil and/or fat from the scalp, thereby stimulating the scalp. For example, tiny salt crystals would absorb oil onto their surface. For example, the salt wicks out moisture due to the hypertonicity of the out layer, the wicking also involving flow of sebum and oil.

Non-limiting examples of drugs that can be applied to the scalp (e.g., directly onto the scalp, indirectly by oral administration) include; Minoxidil, Finasteride, Dutasteride, saw palmetto oil.

Apply Treatment

FIGS. 10A-10G illustrate some embodiments of the hair stimulation device. The embodiments are used to apply one or more treatment protocols as described herein to the scalp of the user.

Figure 10A:
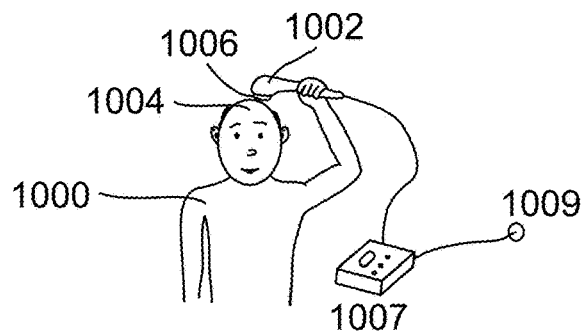
FIGS. 10A-10G are illustrations of embodiments of the hair stimulation device, in accordance with some embodiments of the invention.

FIG. 10A illustrates a hand held embodiment of the hair stimulation device, in accordance with some embodiments of the invention. A user 1000 holds a hair stimulation device 1002 (e.g., as described with reference to FIGS. 1, 3A and/or 3B) to a scalp 1004.

In an exemplary embodiment, device 1002 comprises a needle array 1006 of discs (e.g., as described with reference to FIG. 1). Optionally, device 1002 is connected to control box 1007. Optionally, control box 1007 comprises a display. Optionally, control box 1007 is connected to power supply 1009.

Figure 10B:
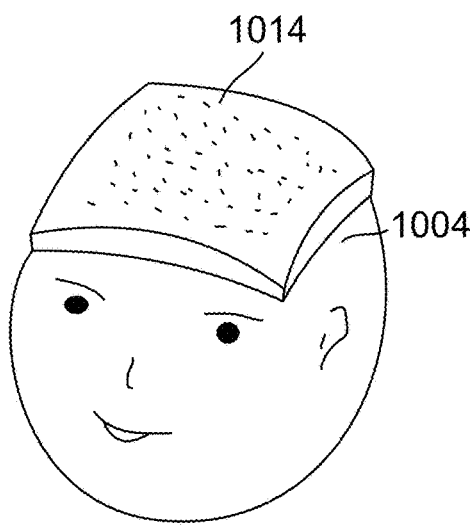
Figure 10C:
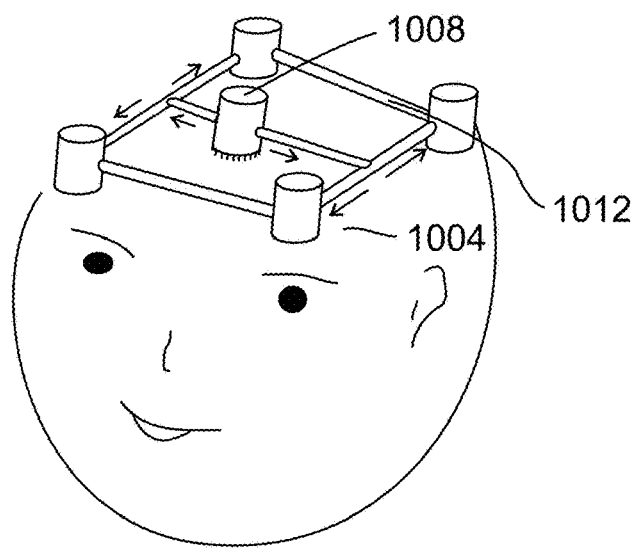
Figure 10D:
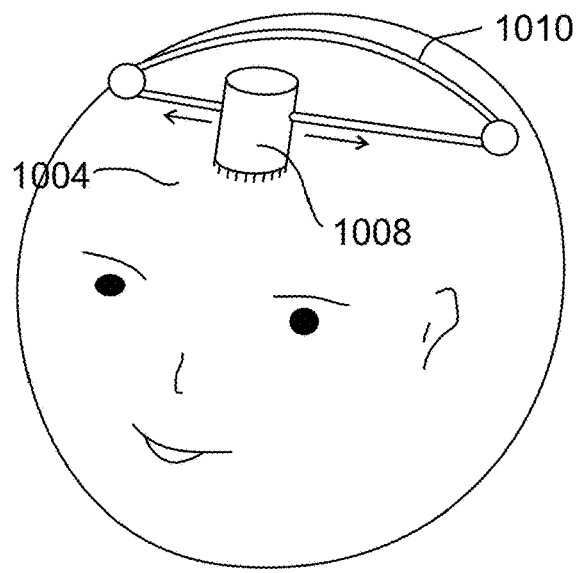
Figure 10E:
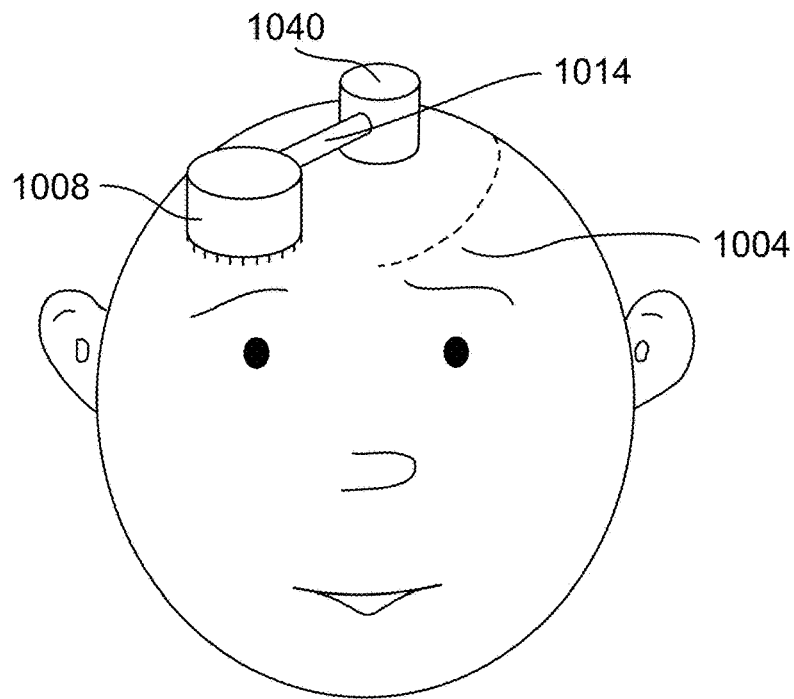
Figure 10F:
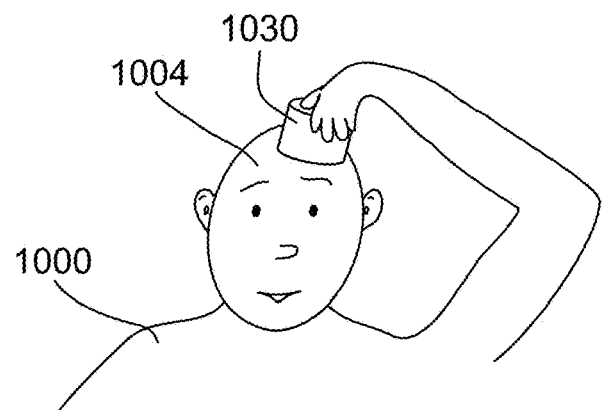

FIG. 10F illustrates a handleless 1030 version of the hair stimulation device, for example, device 100 without handle 114 as illustrated in FIG. 1. Optionally, user 1000 holds and/or displaces device 1030 across scalp 1004 by holding device 1030 directly at a housing, for example, at housing 110. Optionally, device 1030 is rolled over scalp. Potentially, device 1030 may be easier to move and/or position by some users.

In some embodiments of the invention, user 1000 applies treatment by manually displacing device 1002 with respect to scalp 1004. Optionally, device 1002 applies treatment by rolling over scalp 1004, for example when a needle array 1006 of discs (e.g., as described with reference to FIG. 1) is used. Alternatively or additionally, device 1002 applies treatment when device 1002 has been positioned over the treatment area of scalp 1004, for example by insertion and/or retraction of needles into the scalp, for example, when using array 1006 of needles for example described with reference to FIG. 7A.

In some embodiments of the invention, there is a setting that allows user 1000 to tell device 1002 the area of scalp 1004 being treated. For example, a button or a sensor signals the position to the controller. Optionally, device 1002 changes treatment parameters based on the area of scalp 1004 being treated. For example, areas with relatively less hair may require relatively more intense treatment than areas with relatively more hair.

In some embodiments of the invention, the needle array head of the hair stimulation device is automatically displaced relative to scalp 1004 to apply treatment, for example, by a robot.

FIG. 10D illustrates a robot 1010 moving a needle head array 1008 across scalp 1004 along one axis (e.g., forward or reverse), in accordance with some embodiments of the invention. Optionally, the relative position is known by first calibrating the position of array 1008, for example, by pressing a 'start' button.

FIG. 10C illustrates a robot 1012 moving needle head array 1008 over scalp 1004 along two axes, in accordance with some embodiments of the invention.

FIG. 10E illustrates a robot 1014 moving needle head array 1008 over scalp 1004 in a rotational manner, in accordance with some embodiments of the invention. Optionally, robot 1014 comprises motorized spinner 1040.

In some embodiments of the invention, the needle head array of the hair stimulation device is static relative to scalp 1004. Treatment is applied by selectively activating needles, for example insertion and retraction of the needle into scalp 1004, for example, using actuators as described with reference to FIG. 7A.

FIG. 10B illustrates an array of needles 1014 statically positioned over the treatment area of scalp 1004, in accordance with some embodiments of the invention. Optionally, array 1014 covers the entire area to be treated. Alternatively, array 1014 does not cover the entire area to be treated. Optionally, the user moves array 1014 from one location to another. At each location, array 1014 is statically positioned relative to scalp. For example, array 1014 may treat the area around the temple and then move to the area of the vortex.

In some embodiments, the device is intended for one time use. For example, the device may be in the form of a disposable pad with needles, applied manually to the scalp and incorporating a power source, for example, to provide power to deposit ions. Alternatively, no independent power source is necessary. For example, the device relies on galvanic reactions for power. Optionally, the device may be used a limited number of times, for example 5, 10 or 30 times. Optionally, the limited use of the disposable and/or limited use pad provides greater sterility and/or decreases the change of infection. Alternatively, the pad is disposable but connects to a reusable power source.

Figure 10G:
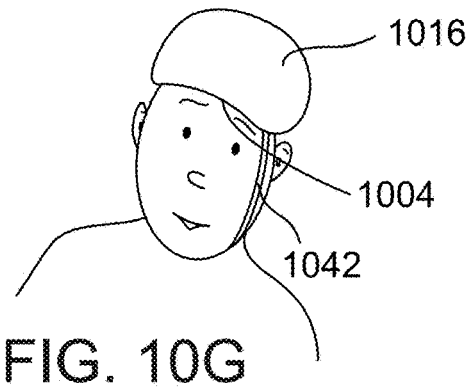

FIG. 10G illustrates a helmet 1016 comprising needles, positioned at least over some of scalp 1004, in accordance with some embodiments of the invention. Needles are selectively activated to treat regions of scalp 1004, for example, selectively inserted and retracted. Optionally, helmet 1016 remains statically positioned relative to scalp 1004. Optionally, helmet 1016 comprises chin strap 1042. In an exemplary embodiment of the invention, helmet 1016 treats all areas of scalp 1004. Optionally or alternatively, helmet 1016 treats all areas of scalp 1004 automatically.

Controller

In an exemplary embodiment of the invention, a controller (e.g., controller 308 as described with reference to FIG. 2) controls the application of one or more treatment protocols (e.g., mechanical stimulation, vibration, heat, ion discharge, drug delivery, electrical stimulation, as described herein) by the hair stimulation device. Optionally, the controller is integrated with the device itself, for example logic embedded in the body of the device (e.g., in housing 110 and/or handle 114 as described with reference to FIG. 1). Alternatively or additionally, the device is connected to a separate control box housing the controller. Alternatively or additionally, the device and/or the control box are connected to a computer, having control software thereon.

In an exemplary embodiment of the invention, the controller performs monitoring functions of the hair stimulation device, for example during application of treatment, for example, as will be described in the section "Feedback/Monitoring".

In an exemplary embodiment of the invention, the controller collects feedback data of the treatment by the hair stimulation device, for example as will be described in the section "Feedback/Monitoring".

In an exemplary embodiment of the invention, the treatment is administered by controller 308 according to logic (e.g., a software module), for example using a table. Optionally, the table is stored on a memory (e.g., memory 306 as described with reference to FIG. 2). In an exemplary embodiment of the invention, the table contains treatment parameters correlated with values, non-limiting examples include; patient age, degree of baldness, effectiveness of previous treatment parameters. Optionally, the treatment parameters are based on trial and error, for example, empirical data collected from the patient for example by sensor 304 and/or controller 308 during the treatment. Alternatively or additionally, treatment parameters are based on experimental data from a population of subjects. Alternatively or additionally, controller 308 is manually programmed, for example, by a physician. Alternatively or additionally, controller 308 operates according to mathematical models (e.g., equations).

Feedback/Monitoring

In some embodiments of the invention, the application of treatment for example using one or more treatment protocols is monitored. Optionally, monitoring comprises comparing the delivered treatment against the selected protocol.

In some embodiments of the invention, feedback regarding the application of treatment for example using one or more treatment protocols is obtained. Optionally, feedback is analyzed to estimate the effectiveness of treatment using the selected protocol.

In some embodiments of the invention, hair growth is measured. Optionally, hair growth is measured manually, for example, by taking a picture of the scalp (the entire scalp and/or a zoom-in of a particular area) and having an expert provide an assessment, for example, by counting the number of hairs. Alternatively or additionally, software automatically analyses the pictures, for example, counting the hairs.

In some embodiments of the invention, monitoring and/or feedback is dynamic, for example, to evaluate the application of the protocol during the treatment. Alternatively or additionally, feedback and/or monitoring occurs over a substantially long period of time, for example, to evaluate the application of the protocol over several treatment sessions.

In some embodiments of the invention, one or more sensors, for example sensor 304 described with reference to FIG. 2 are utilized in monitoring and/or feedback of treatment.

In some embodiments of the invention, impedance of the scalp is measured. A potential usage is to monitor the piercing of the skin of the scalp by the needles. Optionally, impedance is evaluated for the entire needle array. Alternatively or additionally, impedance is evaluated for groups of needles and/or individual needles.

In some embodiments of the invention, relatively high impedance is significant, for example, suggesting a lack of sufficient contact for example between the needles and the scalp. Non-limiting examples of relatively high impedance include over $10^5$ ohm, over $10^6$ ohm, over $10^7$ ohm, or other smaller, intermediate or larger values are used. Another non-limiting example is the currently measured impedance relative to previously measured impedance (e.g., of the same patient), for example, over 5×, 10×, 25× higher, or other smaller, intermediate or larger measurements are used.

In some embodiments of the invention, relatively low impedance is significant, for example, suggesting a short circuit, for example between the needles due to an excessively sweaty scalp. Non-limiting examples of relatively low impedance include, for example, less than $10^2$ ohms, less than $10^3$ ohms, less than $10^4$ ohms, or other smaller, intermediate or larger values are used. Another non-limiting example is the currently measured impedance relative to previously measure impedance (e.g., of the same patient), for example 0.1%, 1%, 10% of the previous value, or other smaller, intermediate or larger measurements are used.

In some embodiments of the invention, the number of needle pricks applied to the skin is calculated and/or estimated. Optionally, the number of disc rolls (and partial rolls) is counted In some embodiment of the invention, the position of the needle array relative to the scalp is estimated, for example the location of the needles piercing the skin. Optionally, the position is compared to evaluate if the user and/or robot treated the selected areas of the scalp. For example, the position is evaluated using a sensor, for example, an accelerometer. In a non-limiting example, position tracking is measured relative to a starting position. The accelerometer measures acceleration, which is integrated over time to calculate distance. The initial position and angle relative to the scalp are used to create a movement map.

In some embodiments of the invention, the skin temperature is estimated, for example by a temperature sensor. Alternatively or additionally, the change of color of skin is estimated, for example by an optical sensor. A potential advantage is to obtain feedback about the extent of treatment. For example, an increase in skin temperature and/or change of skin color (e.g., reddening) can signify the onset of the inflammatory response in response to the treatment, possibly signifying that the area of skin has been sufficiently treated.

In some embodiments of the invention, monitoring and/or feedback are manual, for example, a physician or other trained practitioner observing the user using the device and/or providing comments to the user. For example, a physician or other trained practitioner visually examining the skin scalp of the user, for example for hair growth, for example, between treatment sessions.

In some embodiments of the invention, monitoring and/or feedback is provided for the user. Optionally, monitoring and/or feedback are subjective. Non-limiting examples include; the degree of pain experienced during treatment, user perception of effectiveness of hair stimulation, user compliance with the protocol.

Figure 11:
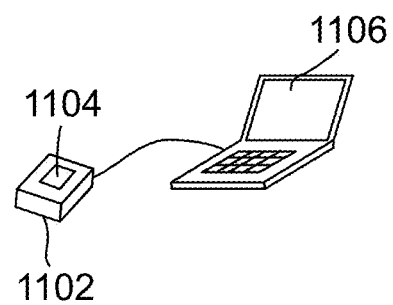
FIG. 11 is an illustration of a monitoring and/or a feedback set-up used with the hair stimulation device, in accordance with some embodiments of the invention.

FIG. 11 illustrates a monitoring and/or feedback set-up used with the hair stimulation device, in accordance with some embodiments of the invention. Optionally, a control box 1102 comprises one or more user interfaces 1104 displaying information about the use of the device. Alternatively or additionally, a computer 1106 (containing control software thereon) displays monitoring and/or feedback information about the use of the device on a monitor.

In some embodiments of the invention, the monitoring and/or feedback data is sent to a remote location, for example, to be analyzed by a trained professional.

In some embodiments of the invention, the device, control box 1102 and/or computer 1106 connect to the internet to download and/or upload data. Connections can be wired and/or wireless.

Adjust Treatment Parameters

In some embodiments of the invention, one or more treatment parameters of the treatment protocols are adjusted. Optionally, adjustments are made according to monitoring data. Alternatively or additionally, adjustments are made according to evaluation data. Alternatively or additionally, adjustments are made according to predetermined changes in the treatment parameters of the treatment protocols, for example over time and/or over treatment sessions.

In some embodiments of the invention, adjustments are made dynamically, for example during the treatment session.

In some embodiments of the invention, adjustments are made before the start of the next treatment session.

In some embodiments of the invention, the intensity of treatment is relatively increased. For example, if the treatment is not sufficiently effective. Non-limiting examples include; the addition of another stimulation protocol (e.g., adding thermal stimulation), relatively increased density of needle pricks, relatively increased dose of ions deposited.

In some embodiments of the invention, the intensity of treatment is relatively reduced. For example, if the treatment is causing side effects, for example pain, excessive swelling and/or bleeding. Non-limiting examples include; removing a stimulation protocol (e.g., removing thermal stimulation), relatively thinner needles, relatively reduced density of needle pricks, relatively reduced dose of ions deposited.

Repeat

In an exemplary embodiment of the invention, treatment is repeated.

In some embodiments of the invention, treatment is repeated once the skin has sufficiently healed, for example, when the inflammatory response has subsided.

In some embodiments of the invention, treatment is repeated according to the treatment protocol, for example, once every 3 days, or once every 5 days, every 7 days, or other smaller, intermediate or larger time frames are used.

Kit

Figure 12:
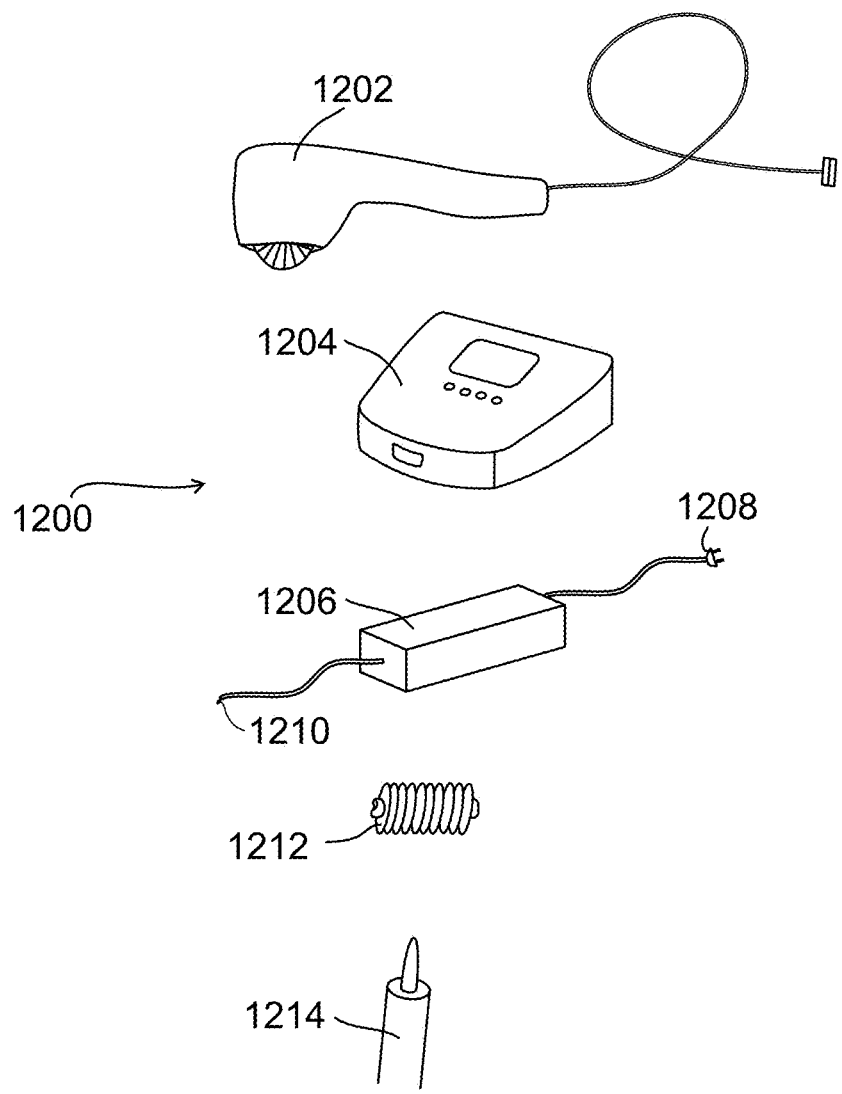
FIG. 12 is an illustration of a hair stimulation kit 1200 in accordance with some embodiments of the invention.

FIG. 12 illustrates components of a hair stimulation kit 1200 in accordance with an exemplary embodiment of the invention. One or more parts of kit 1200 can be sold separately or as a package.

In some embodiments of the invention, kit 1200 comprises a hand-held hair stimulation device 1202. Optionally, device 1202 comprises batteries, for example rechargeable batteries.

In some embodiments of the invention, kit 1200 comprises control box 1204. Box 1204 can be used to perform one or more controller functions for device 1202.

In some embodiments of the invention, kit 1200 comprises an AC adapter 1206. Adapter 1206 has a plug 1208 to fit a standard electrical outlet (for example in a home), and a connector 1210 to fit device 1202.

In some embodiments of the invention, kit 1200 comprises one or more disc replacement packages 1212. Alternatively or additionally, discs 1212 are sold separately. Discs 1212 can come in a variety of designs, for example depending on the selected treatment protocols. One or more non-limiting examples of variations in discs 1212 include; number of discs per package, diameter of discs, size of needles on discs, number of needles per disc, spacing between discs, metallic coating, drug delivery sponge.

Some non-limiting examples of disc variations include;

4 discs (e.g., instead of 8), for example, for those with long or dense hair, the 4 discs having double the space between the discs relative to the 8 disc arrangement.

Needles having a pricking depth ranging from 0.1 mm to 1 mm pricking depth (e.g., 0.2 mm, 0.4 mm, 0.6 mm, 0.8 mm).

Discs with additional 5 or 10 mm in diameter; for example, for long or dense hair.

Discs coated with Zn, Cu, Fe, or no coating.

In some embodiments of the invention, discs 1212 are disposable. Alternatively or additionally, discs 1212 can be sterilized.

In some embodiments of the invention, kit 1200 comprises one or more drugs 1214, for example topical additives. Alternatively or additionally, drugs 1214 are sold separately. Non-limiting examples of additives include; Soothing gel: 60 to 120 ml; minoxidil solutions: 30 to 60 ml; other non-drug hair promoting (e.g. sow palmetto oil): 60 to 120 ml; hair strengthening shampoo: 100 to 500 ml.

In some embodiments of the invention, kit 1200 comprises cleansing wipes and/or other cleaning aids, for example shampoo.

Some non-limiting examples of exemplary kits include;
Device 1202, control box 1204 and AC adapter 1208.
Disc replacement 1212, topical additive 1214.
Device 1202, control box 1204 and AC adapter 1208, disc replacement 1212.
Device 1202, control box 1204 and AC adapter 1208, disc replacement 1212, additive 1214.

Light Stimulation

In an exemplary embodiment of the invention, light (visible or infrared) is applied to the skin, either below the scalp surface, for example, by means of internal light sources or guides, or from above the surface. Optionally, light guides are transparent discs or needles or optical fibers embedded in the discs or needles. Optionally, the optical fiber replaces the needles. Optionally, the light source is located at the axis of the wheel.

Figure 14B:
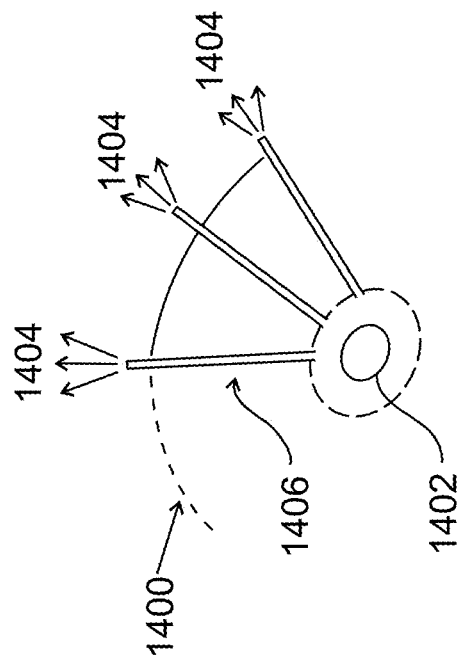
FIGS. 14A-14B are illustrations of embodiments of discs, in accordance with some embodiments of the invention.
Figure 14A:
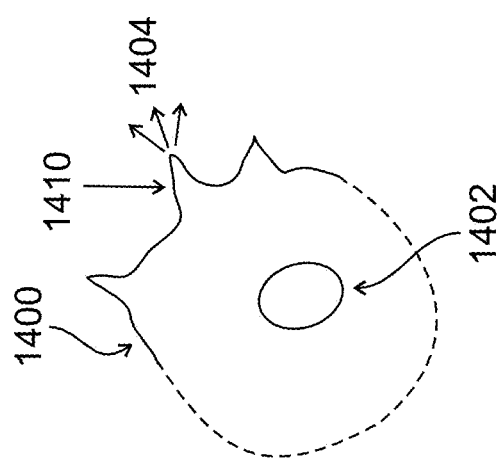

FIGS. 14A and 14B illustrate discs comprising a light source. In an exemplary embodiment, light conducting disc 1400 (FIG. 14A) comprises light source 1402 causing light 1404 to emanate from spike 1410 on disc 1400. Optionally, disc 1400 comprises translucent material. Optionally or alternatively, spike 1410 comes to a sharp point. Optionally, spike 1410 is metallic.

FIG. 14B illustrates an exemplary embodiment in which light 1404 originates from light source 1402 and travels through optical fibers 1406 embedded in disc 1400. Optionally, the optical fibers 1406 penetrate directly into the skin. Optionally, optical fibers 1406 are thin enough to easily penetrate skin.

In some embodiments, one or more discs each comprise multiple fibers and/or needles. Optionally, at least one disc is for optical stimulation. Optionally or alternatively, at least one disc is metallic. Optionally or alternatively, at least one disc includes both optical needles and metallic needles. Optionally, at least one needle is both optical and metallic. Optionally or alternatively, fiber and/or needle are provided on parallel discs. Optionally or alternatively, fibers and/or needles are provided in a planar array.

Figure 15:
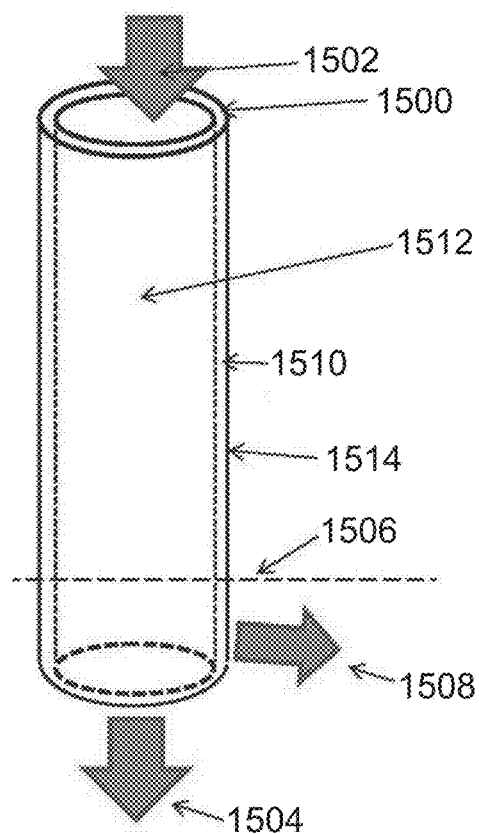
FIG. 15 is an illustration of a light source in accordance with some embodiments of the invention.

FIG. 15 illustrates an injector comprising a light guide, in accordance with an exemplary embodiment of the invention. In an exemplary embodiment, the light guide is an optical fiber coated with metal. For example, light is produced by light source 1502 which is powered by power source 1500 and emanates light 1504. Optionally, power source 1500 is electrical.

In some embodiments, power source 1500 emits ions 1508 directly into the scalp beneath the scalp surface 1506. Optionally, power source 1500 emits electricity directly into the scalp beneath the scalp surface 1506. Optionally, power source 1500 emits heat directly into the scalp beneath the scalp surface 1506. Optionally, the discs, needles and/or optical fibers also vibrate.

In some embodiments, the injector comprises a cavity 1512. Optionally, cavity 1512 comprises a light conducting core. For example, cavity 1512 may comprise light transmitting material. Optionally, the light transmitting material has structural rigidity. Optionally or alternatively, the light transmitting material has minimal structural rigidity.

In some embodiments, cavity 1512 comprises an internal optical fiber. For example, the internal optical fiber may comprise a metal coated thin optical fiber. Optionally or alternatively, the internal optical fiber may comprise an external shell conducting electricity. Optionally or alternatively, the internal optical fiber may comprise an external shell conducting heat. Optionally or alternatively, the internal optical fiber may comprise an external shell conducting injecting ions into the skin. Optionally or alternatively, the internal optical fiber may emit light into the skin.

In some embodiments, hollow cavity 1512 comprises a void which transmits light. Optionally, the outer portion 1510, inside outer layer 1512, of the injector comprises a source of vibration. Optionally or alternatively, the outer portion of the injector comprises a source of heat.

In some embodiments, the outer layer 1514 comprises an electrical conductor. For example, outer layer 1514 comprises metal. Optionally, outer layer 1514 is coated with ions to be deposited. For example, outer layer 1514 is coated with Cu. Alternatively, outer layer 1514 is coated with Zn. Optionally, outer layer 1514 comprises heat conducting material.

Various embodiments and aspects of the present invention as delineated hereinabove and/or as claimed in the claims section below find experimental support in the following examples:

Example—Experiment

Reference is now made to the following example, which together with the above descriptions illustrates some embodiments of the invention in a non-limiting fashion. In particular, features described below may be used without other described features and in conjunction with methods and/or apparatus as described above.

Figures 13A, 13B:
FIGS. 13A-13B are images of a scalp before and after hair stimulation treatment, useful in practicing some embodiments of the invention.

Patient Profile:

The subject of the experiment was one of the inventors, Mr. Dov Ingman. Mr. Ingman is 63 years old. He has been slowly balding for the past 30 years. FIG. 13A is an image of Mr. Ingman's scalp taken during October 2007, before treatment was started on February 2011. The state of hair at the beginning of the treatment was very similar to the one in the 2007 picture.

Treatment Parameters:

Mr. Ingman is a potential candidate for treatment using the hair stimulation device as in some embodiments described herein, for example, satisfying inclusion criteria, and not fitting any exclusion criteria.

Treatment was selected to be applied to the entire scalp, a total treatment area of about 40 000 $mm^2$ (e.g., 200 mm×200 mm). The treatment protocol was initially selected to be 2-4 minutes, applied on a daily basis. The treatment regimen results in mild pain. To try and reduce the pain, the treatment parameters were changed to 2-3 sessions per week, for about 5 minutes per treatment and at a reduced vibration amplitude. The change resulted in reducing the pain to a tolerable level of subtle pain. Furthermore, the frequency and/or time duration have been selected to achieve a balance between sufficient stimulation and sufficient recovery of the skin from the stimulation (e.g., to withstand another treatment session).

Device Selection:

The device used was the hand-held version of the hair stimulation device, as illustrated in FIG. 3A. The device uses discs with needles on the circumference of the discs, as illustrated in FIG. 3C. The design of 8 discs has been selected. Alternating discs are coated with copper and/or zinc. The radius of each disc is 16 mm Each needle on the disc is 1 mm apart. The area that each needle pricks is about 0.0001 $mm^2$ (e.g., using square needles of 0.1 mm×0.1 mm). Discs are 3 mm apart.

Mechanical Stimulation Protocol:

The density of pricks has been prescribed at about 10 pricks per $mm^2$ of the scalp. Examples of parameters to achieve this density:

With a circumference of about 100 mm (radius of 16 mm) and a needle spacing of 1 mm, one roll of the disc will prick the scalp 100 times. 8 discs, rolled 500 times over the scalp (in a single treatment session) will prick the scalp about 400 000 times.

The total area of all the pricks during the treatment session is about 40 mm$^2$. The percentage of the total area of the scalp that is treated per session is about 0.10%.

Vibration Protocol:

The vibration of the needles has been selected to be about 50 Hz, with vibrations both perpendicular to the scalp surface and sideways perpendicular to the path of motion.

In an exemplary embodiment of the invention, the area per prick can be increased about 10×, for example, by an omni-directional vibration of the needles (e.g., by vibrating the discs). A potential advantage is to increase the mechanical stimulation if the current parameters are evaluated as not being sufficiently effective.

Ion Deposition Protocol:

The density of type I alpha-reductase inhibitors (zinc and copper) has been selected to be about 8 nano-grams per cm$^2$ of skin for each of the ion types. Examples of parameters to achieve this density:

During one treatment, a total charge of 100 nano-Amperes per second through all of the zinc coated needles, and a similar charge through all of the copper coated needles, will result in a deposition density of over 8 nano-grams per cm$^2$ of skin for each of the ion type. (Atomic weight of zinc is 65.4 gram/mol, atomic weight of copper is 63.5 gram/mol, oxidation state of zinc and copper is 2.)

Thermal Stimulation Protocol:

The heat applied to the tissues has been selected to result in a tissue temperature in the range of 50-60 degrees Celsius.

Electrical Stimulation Protocol

The voltage applied between the discs coated with Zinc and the discs coated with Copper has been selected to be an alternating current (AC) at a frequency of 100 Hz, with a peak to peak voltage of 5 V. The current has been selected not to exceed 2 mA.

Results

FIG. 13B is an image of taken during September 2011. The increase in the amount of hair in comparison to FIG. 13A is significant. The increase in the amount/density of hair seems to vary among different regions. There seem to be more active follicles, with significant conversion from vellus hair to terminal hair. The treatment was applied to all balding areas. The impression provided is an expert's opinion. The expert was closely monitoring the progress.

Additional Example—Experiment

Additional experimental results suggest that the more a person uses the device, the quicker and/or more complete the restoration, enhancement and/or causation of hair growth. Results were improved when treatment was daily and when treatment was focused during a session on a smaller area. Specifically, results were apparently improved for use of the device on smaller area for less time as compared with use of the device on a larger area for more time.

Figure 16:
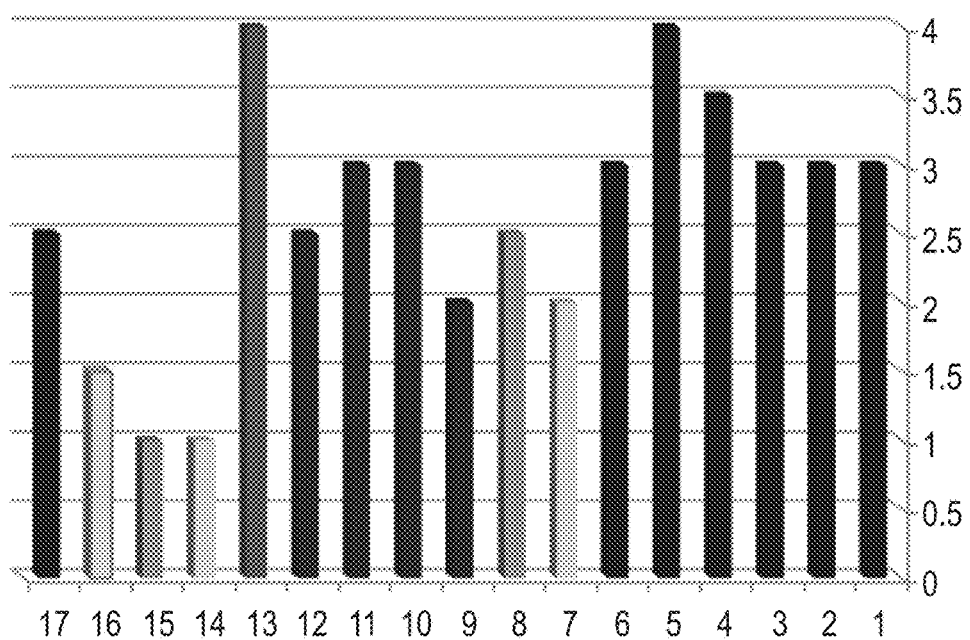
FIG. 16 is a bar chart summarizing experimental results achieved using methods in accordance with some embodiments of the invention.

For example, FIG. 16 is a bar chart summarizing interim results of treatment on subjects who were treated with the device. Overall, 96 patients appeared for the study, with an average age of 40 (89 men, comprising 93% of the sample, with an average age of 39, and 7 women, comprising 7% of the sample, with an average age of 55). 8 patients (8% of the sample), all male, with an average age of 46, did not receive a device because they were rejected from the study or were not interested in receiving the device. 88 patients received a device (Second Generations Pilogics Apparatus for Stimulating Hair Growth and/or Preventing Hair Loss) in total. 21 patients, 20% of the overall sample, all male, with an average age of 43 received a device but left the study before completing 6 months of treatment. 67 patients received a device, with a mean age of 40 (60 men, comprising 80% of patients receiving a device, at an average age of 51, and 7 women, comprising 20% of patients receiving a device, at an average age of 39).

The first 35 patients to receive the device entered the study between Nov. 1, 2011 and Feb. 29, 2012 (30 men and 5 women). Of those 35 patients, 17 men (56% of the 30 men who began treatment), average age of 41, and 4 women (80% of the 5 women who began treatment), average age of 53, completed 6 months or more of treatment with the device. [The age of one female patient, 80, was significantly above average]. 41% of men were age 20-30; 35% of men were age 30-35; and 23% of men were over age 50. 75% of women were age 30-50; 25% of women were over 50.

The bar chart in FIG. 16 summarizes the results of the 17 male subjects who completed at least six months of treatment with the device. Each subject was assigned a score between 0-4, as seen on the y-axis of the bar chart. 0 indicates that a patient withdrew from treatment before the completion of 6 months of treatment. 1 indicates no improvement from the beginning to the end of treatment, as seen in a comparison of the first and last photograph taken of the scalp of the subject. 2 indicates a slight improvement seen between the first and last photo. 3 indicates a tangible improvement seen between the first and last photo. 4 indicates a significant improvement between the first and last photo. Each patient who completed treatment was assigned a bar reaching a height of between 1 and 4, depending on their results.

Each patient was further assigned a color to their bar depending on the initial state of their hair loss. Subjects who began the treatment with a slight amount of hair on their scalp were assigned a black bar. Subjects with patches of baldness were assigned a gray bar. Subjects with large areas of baldness were assigned a white bar.

As reflected in the bar chart, 2 of the 17 male patients saw no improvement; 1 patient saw an improvement described as intermediate between no improvement and minor improvement, 2 patients saw minor improvement, 3 patients saw improvement described as intermediate between minor improvement and tangible improvement, indicates a significant improvement; 6 patients saw tangible improvement; 1 patient saw improvement described as intermediate between tangible improvement and significant improvement; and 2 patients saw significant improvement.

Of the 4 women who began treatment with the device, 3 completed at least 6 months of treatment. All 3 women who completed the treatment saw tangible improvement (a score of 3 if they were to be included in the bar chart).

None of the patients who used the device saw their hair recede during treatment.

Treatment Protocol

In accordance with the protocol of the study, patients received an average of 2-3 treatments a week for five minutes. Each patient received a Prologics Generation 2 device and a frequency of treatment of 5 minutes 3 times per week in the first month. According to the protocol, patients were permitted to increase the frequency of treatment.

Results:
1. Frequency of treatment: Men were found to be more likely to choose the option of increasing the frequency of treatment. Additionally, several patients failed to follow the prescribed frequency of treatment, for various reasons. Overall, diminished results were seen for those patients who received less than the prescribed treatment.
2. None of the patients who used the device saw their hair recede during treatment.
3. 53% of patients had improvement evaluated as between 3-4, according to the 0-4 evaluation scale described above, indicating tangible to significant improvement. The average age of the three patients receiving significant improvement (score 3.5 to 4) was 46 (53, 33 and 52). Three with the rank of alopecia hair medium short writers, and hereditary baldness. The 33-year-old patient received notable improvement, with a very significant change observed from test to test. That patient received treatment diligently every day for approximately 20 minutes. His hair is on the way back to full coverage.
4. Of the patients between age 50 and 59, they each began treatment with short hair and with the same moderate degree of baldness, spread out over the entire upper area of the scalp and seen more at the top. These patients underwent continuous treatment, with 80-100% conformity with the protocol.
5. 6 patients (35% of the patients) received scores of 3, indicating tangible improvement. These patients saw and felt their hair improving and the photographs also show a positive visual change. Two of these patients (33% of the patients) were between age 50 and age 59, and 66% of these patients were between age 20 and age 30. The majority of these patients began treatment with a moderate degree of baldness spread out over the entire upper area of the scalp and seen more at the top (as with the group which saw significant improvement). It is possible to conclude that men around the age of 50 with a moderate degree of baldness spread out over the entire upper area of the scalp have a high potential to improve significantly than younger people who have the same degree and location of baldness. The youngest patient in this group, 23-year old patient, received an additional point because, in his case, baldness began at a very young age and the receding of his hairline occurred very quickly and there was a significant change in relation to what would have been without treatment.
6. 3 patients (17% of the patients) received a score of 2.5, indicating an improvement that the patient feels and possibly sees, but is still not particularly striking, and can principally be seen in photographs.
7. 5 patients (29% of the patients) received disappointing results in relation to the others, receiving scores between 1 and 2. The majority of these patients were between age 30 and age 39.
8. In all a significant improvement was seen in 18% of the patients; tangible improvement was seen in 35% of the patients; a moderate improvement was seen in 18% of the patients; and a minor improvement or no improvement was seen in 29% of the patients.

To summarize the results, 70% of the male patients who underwent treatment for 6 months or more received results ranked between 2.5 and 4 and self reported that the treatment had a positive effect on their hair, that the treatment brought a cessation to the consistent and sustained, multi-year, gradual decline in the density of their hair and in the area of coverage their hair supplied to their scalp was. The patients further reported a sharp and fast change from receding hair to improving hair density and coverage at a level marked by visual improvement during treatment.

Patients reported feeling positive about the progress of the treatment even when visible change was difficult to detect. Most patients were satisfied with the results they received. No patients reported complaints about pain during treatment.

Additional Embodiments

Figure 17:
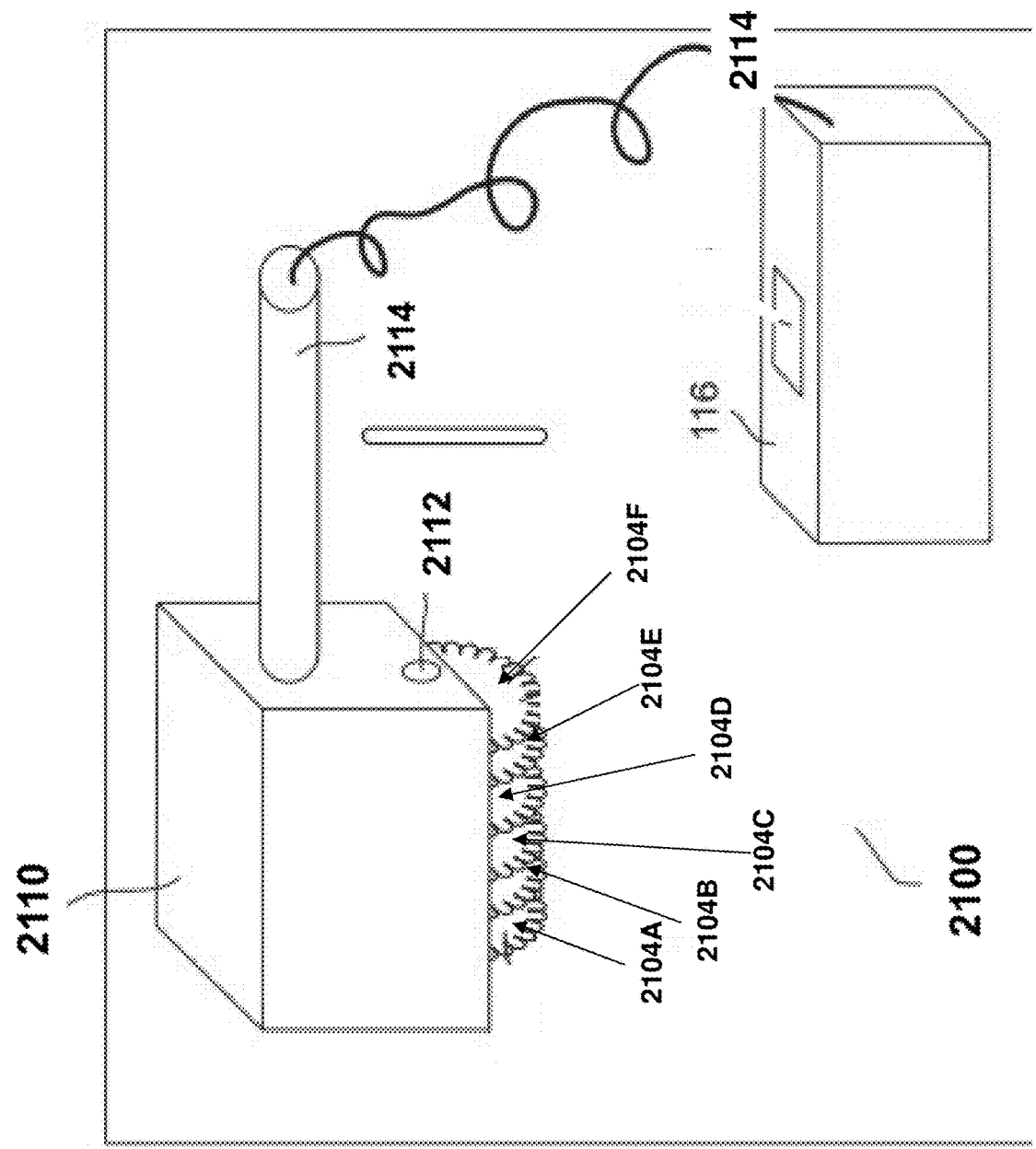
FIGS. 17-21 relate to a device or portion(s) thereof for depositing metal ions on the scalp, for example, to treat a hair-condition such as baldness.
Figure 18:
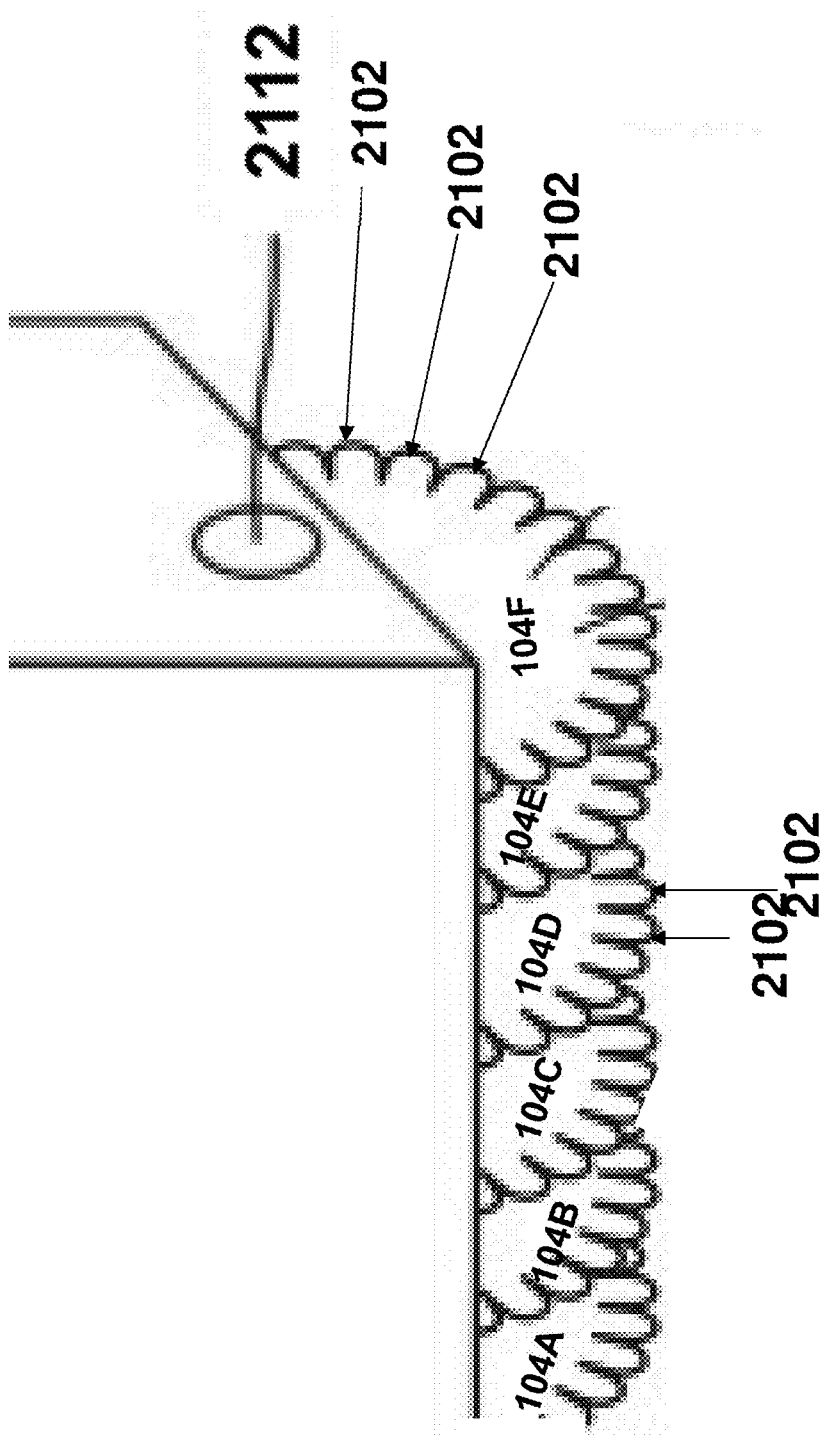

FIG. 17 is an illustration of an exemplary device 2100 for promoting hair growth, in accordance with an exemplary embodiment of the invention. FIG. 18 is a close-up of a portion of the device of FIG. 17. As illustrated in FIGS. 17-18, protrusion-electrodes 2102 are arranged along the circumference of at least one disc 2104, for example, 2, 4, 6, 8, or other smaller, intermediate or larger numbers of discs 2104 are used. In FIG. 17, six discs labeled as 2104A-2104F, are illustrated. The diameter of discs 2104 is, for example, about 2 cm, about 4 cm, about 6 cm, or other smaller, intermediate or larger diameters are used. The thickness of discs and/or electrodes is, for example, about 0.05 mm, about 0.1 mm, about 0.15 mm, or other smaller, intermediate or larger thickness are used.

In some embodiments, the protrusion-electrode as 'ion-releasing' as discussed below. Nevertheless, this is not a limitation—in fact, any feature or combination or feature(s) or embodiment referring to or requiring 'ion-releasing electrode' may, in other embodiments, also refer to an electrode that is not ion-releasing in any context in the present document.

In an exemplary embodiment of the invention, electrodes 2102 and/or discs 2104 are arranged to allow existing hair on the scalp to be displaced (e.g., brushed) away from the electrodes during use. Optionally, discs 2104 are arranged parallel to one another, to allow hair to be brushed between the discs. Discs 2104 are located about 1 mm apart, 3 mm apart, about 5 mm apart, or other smaller, intermediate or larger distances are used.

The shapes of the protrusions 2102 are non-limiting—other examples (which may be used in any embodiment including but not limited to roller-relating embodiments, scalp-brush related embodiments)

In an exemplary embodiment of the invention, electrodes 2102 are coated by at least one metal. Alternatively, electrodes 2102 are made from the metal.

In one non-limiting example related to FIGS. 17-18, a first set of discs (e.g. discs 2104A, 2104C, and 2104E) are coated with a cation (e.g. copper) while a second set of discs (e.g. 2104B, 2104D and 2104F) are coated with an anion (e.g. zinc). In this situation, (i) metal deposition ions comprising the cation are formed contact of electrodes by discs of the first set and (ii) metal deposition ions comprising the anion are formed contact of electrodes by discs of the second set.

As will be discussed below, the alternating cation/anion disc pattern described in the previous paragraph may be useful for ensuring that, after treatment, metal-ion-deposition islands comprising the cation are relatively proximate on the scalp to metal-ion-deposition islands comprising the anion. This may be useful for depositing miniature half-batteries on the user's scalp so that small currents between the deposition islands are sustained after treatment.

For the present disclosure, when a 'metal-ion-deposition island' is formed there is a localized region of scalp wherein for at least one metal, the ion is deposited within the 'deposition island'

Figure 19:
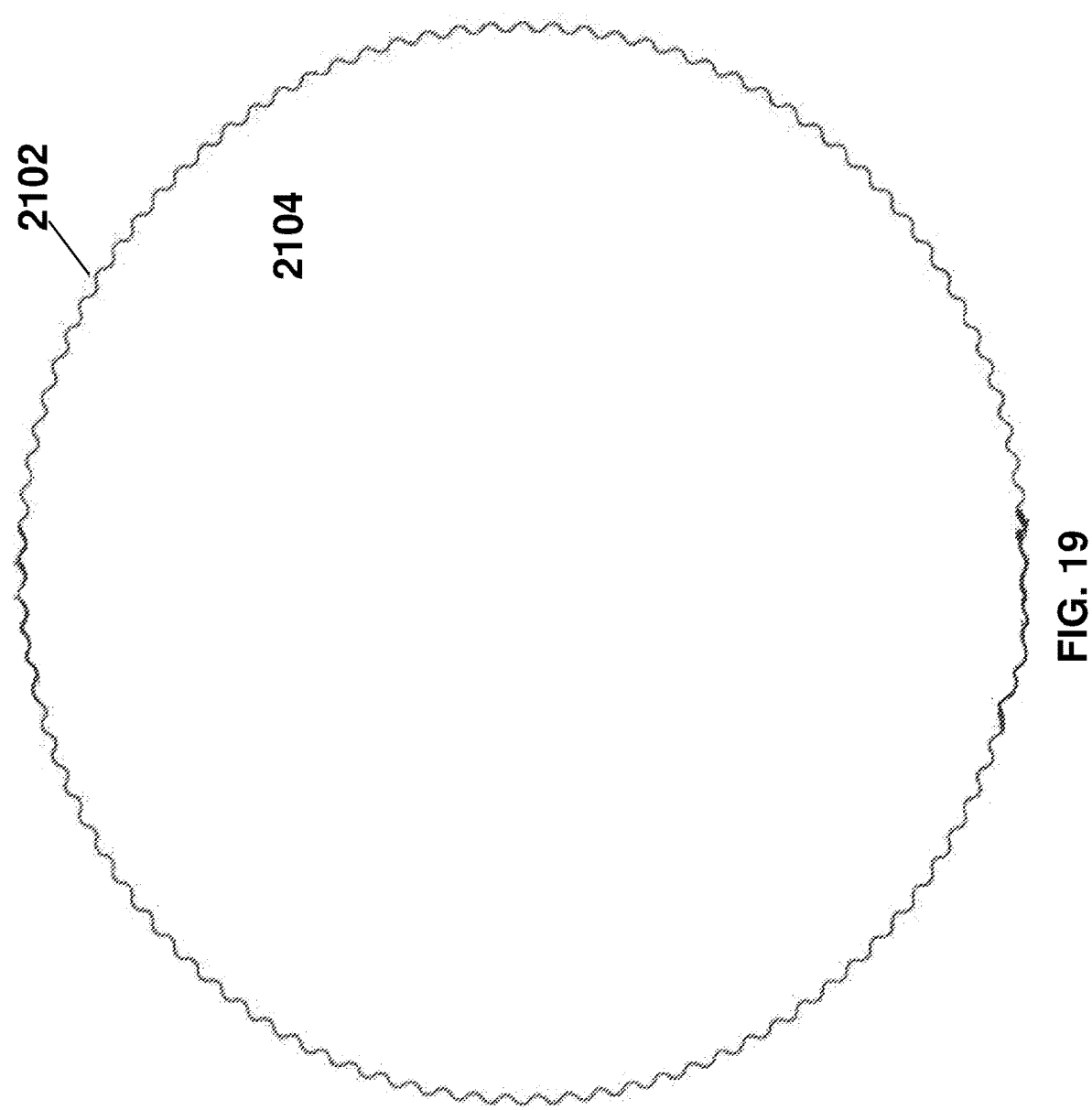

FIG. 19 illustrates an exemplary disc including a plurality of distinct protruding electrodes 2102 disposed uniformly around the disc 2104. The 'uniform distribution feature' is not intended as a limitation.

Figure 20:
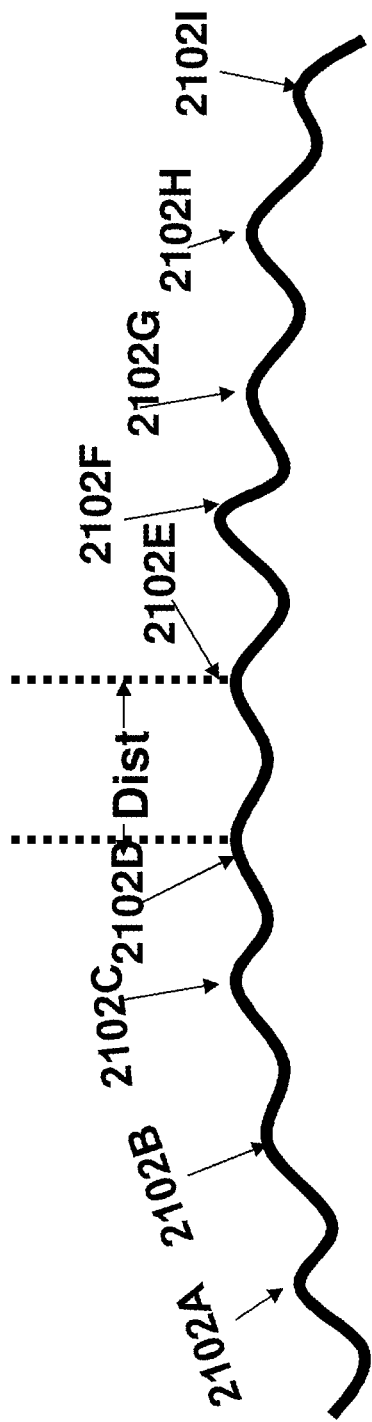
Figure 21:
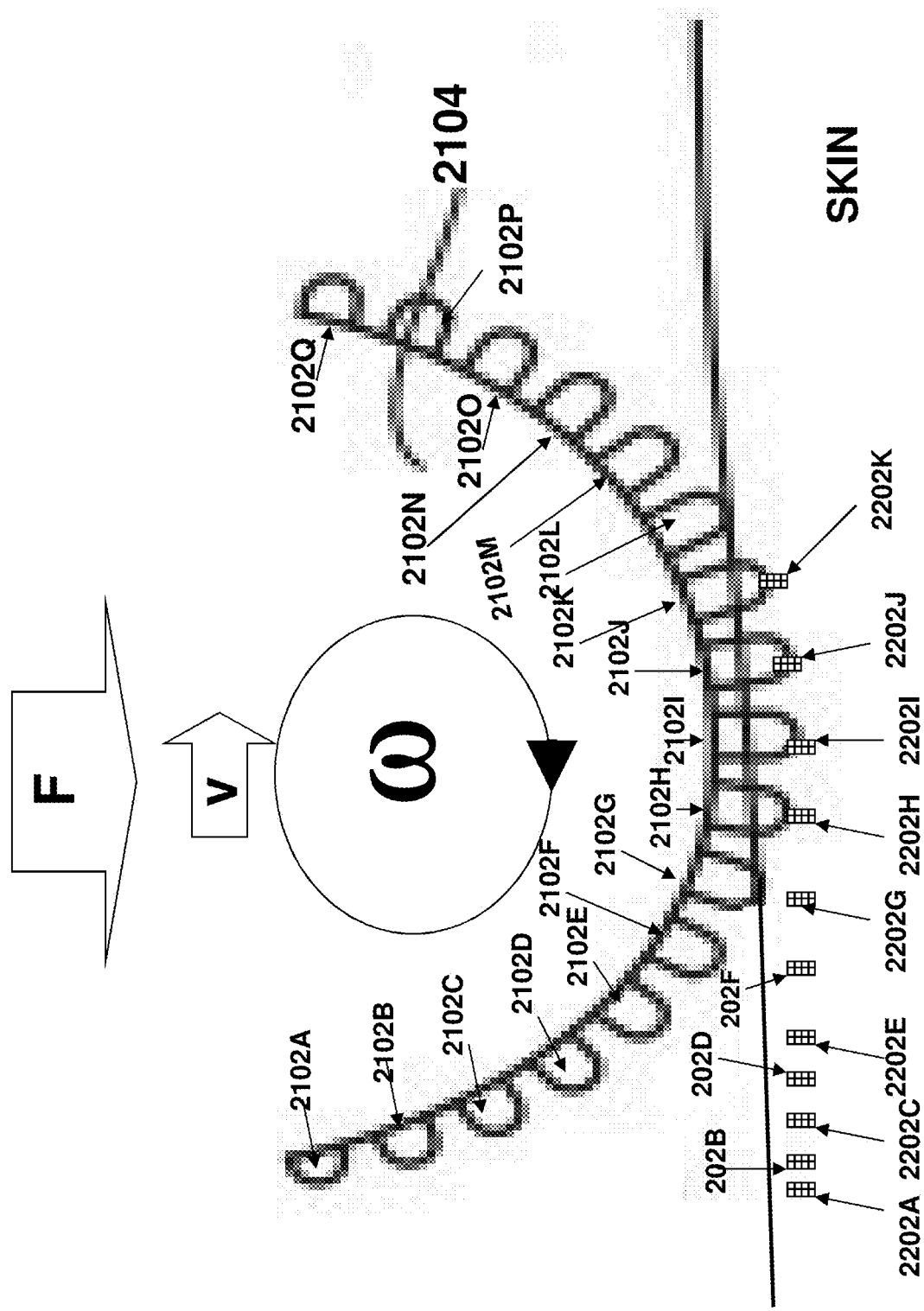

FIG. 20 is a close-up illustration of 10 electrodes 2102A-2102I of a disc illustrating an inter-electrode distance Dist. FIG. 21 illustrates application of a plurality of distinct metal-ion-deposition ions on the surface of the scalp (i.e. the skin thereof) by rolling, without slipping, a disc over the surface of the scalp. In the non-limiting example of FIG. 21, a center of mass of the roller moves linearly and horizontally from left-to-right (i.e. defining a direction of disc velocity v) as a result of counterclockwise rotation. A downward force F is applied in a direction normal to the scalp, or a local surface thereof. As will be discussed below, in some embodiments, when the downward force is localized along a contact-area of each the electrode, a pressure of at least 0.5 mega-Pascals per electrode may be applied to the scalp.

In the example of FIG. 21, whenever an electrode is brought into contact with the skin, the electrode releases metal ions (i.e. either from an interior of the electrode or from a metal-coating that is integrally formed with the electrode). In the example of FIG. 21, electrodes 2102A-2102K respectively form metal deposition islands 2202A-2202K. As illustrated in FIG. 21, in a direction parallel to vector v (representing a direction of linear velocity of the roller), these metal deposition ions are separated on the scalp by a distance that is comparable to the inter-electrode distance illustrated in FIG. 18.

As noted above, in some embodiments, alternating discs are zinc-electrodes and alternating discs are copper-electrodes. According to this non-limiting example, all electrodes 2102 of discs 2104A, 2104C, and 2104E deposit a cation (e.g. zinc) and all electrodes 2102 of discs 2104B, 2104D and 2104E deposit an anion.

Figure 22:
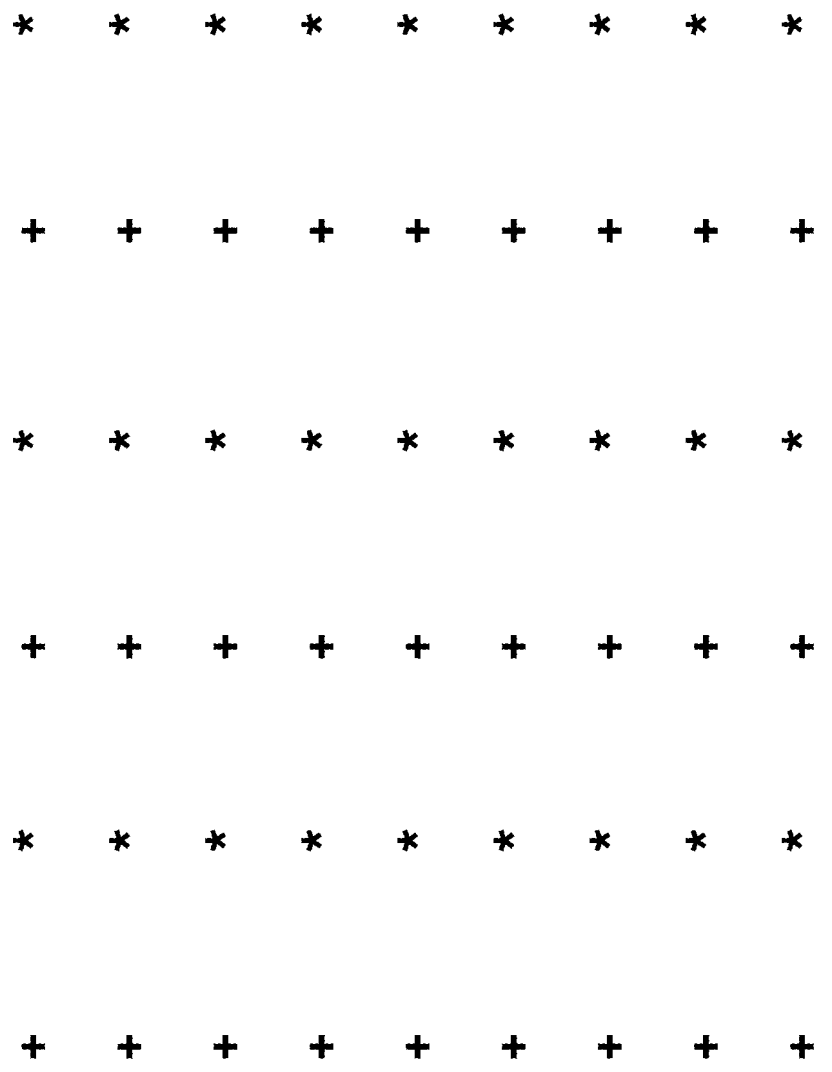

FIG. 22 schematically illustrates metal-ion-deposition islands on the scalp after rolling such a device over a user's scalp. In the schematic example of FIG. 22, cation metal-ion-deposition islands are represented as "+" (plus) while anion metal deposition islands are represented as "*" (star). In this example: (i) a distance between adjacent deposition islands of the same polarity (i.e. a distance between two neighboring pluses, or between two neighboring stars) is approximately equal to an inter-electrode distance for electrodes 2102 disposed along a circumference of a disc; and (ii) a distance between deposition islands of opposite polarity (i.e., a distance between a neighboring star and plus) is approximately equal to a lateral distance between laterally-adjacent discs FIG. 22 relates to the situation of a 'single pass'—i.e. the roller is moved in a single linear direction over the scalp. In some embodiments, the roller may be moved 'back and forth' to perform a 'multi-pass' treatment. For example, the roller may be manually moved, the user may not move the roller in exactly a straight line introducing some degree of randomness in the distances between neighboring deposition-islands.

Figure 23:
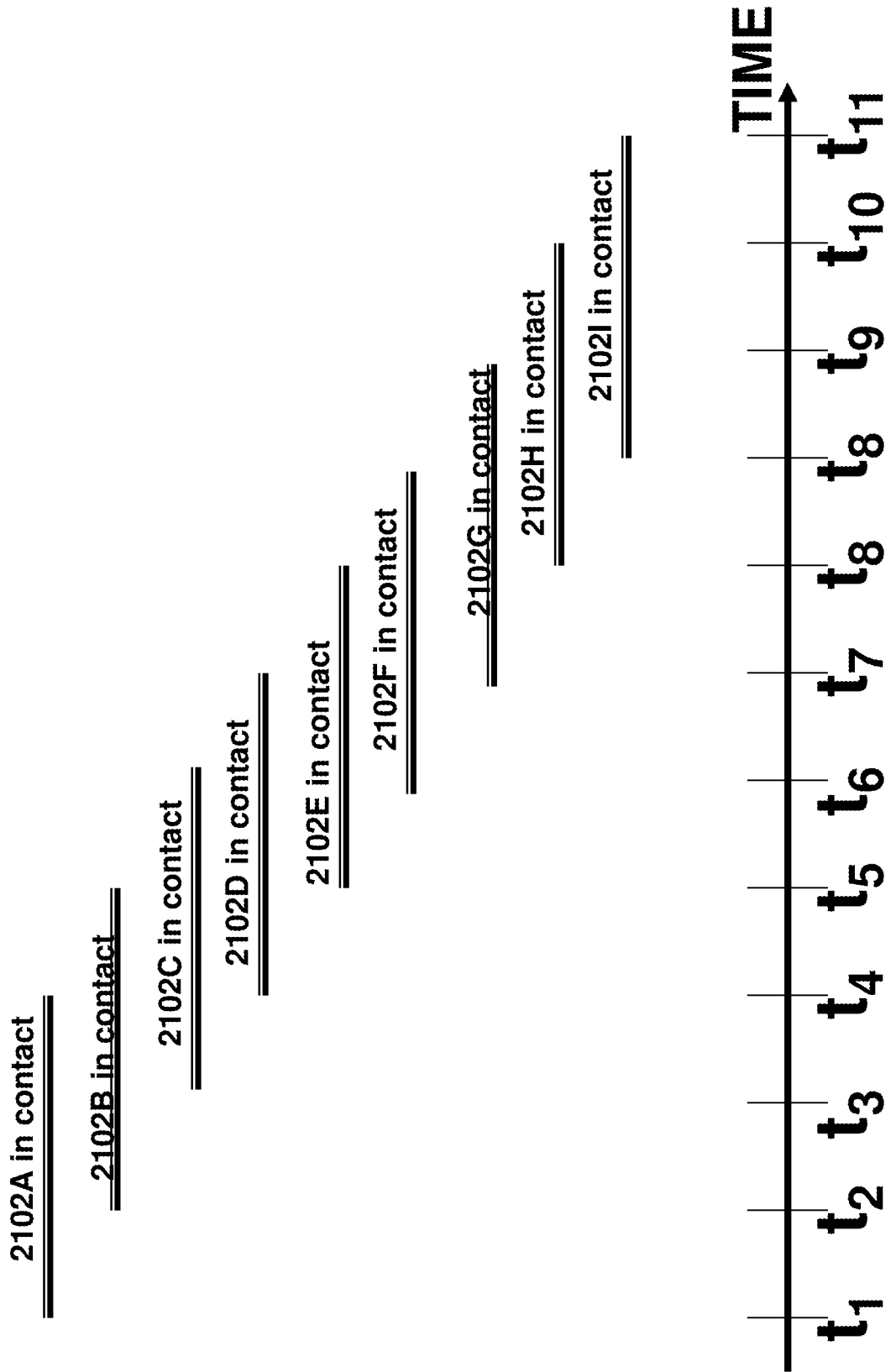
FIG. 23 illustrates a timeline showing where electrodes are brought into contact and out of contact with the scalp.

As illustrated in FIG. 21, in some embodiments, multiple electrodes of the same disc are simultaneously in contact with the scalp—in FIG. 21, electrodes 2102H-2102K are simultaneously in contact with the skin. FIG. 23 illustrates a timeline showing where electrodes 2102A-2102I are brought into contact and out of contact with the scalp—for example, electrode 2102A is in contact with the scalp between times t1 and t4, electrode 2102B is in contact with the scalp between times t2 and t5, and so-on.

When an electrode is in contact with the scalp, this is an 'electrode-scalp contact events'—FIG. 23 illustrates the commencement and conclusion of electrode-scalp contact events for electrodes 2102A-2102I in a heuristic example. Typically and as discussed below, each electrode-scalp contact event is quite brief—for example, at most 100 milliseconds. Nevertheless, the present inventors have found that even this very brief contact is sufficient to form a small metal-deposition island on the scalp, and that it is useful to form a large number of distinct metal-deposition islands, preferably, within a relatively short period of time.

It is possible to employ external electrical power to increase a current between electrodes of opposite polarity through the scalp while both electrodes are in contact with the skin, rather than relying exclusively on the galvanic current between electrodes. In some embodiments, this may allow for a therapeutically significant quantity of metal ions in the metal-deposition-island formed by each contact event selected from a plurality of contact events, despite the relatively short electrode-scalp contact period of each contact event.

In some embodiments, some but not all contact events cause deposition of metal ions on the skin or scalp. In these embodiments, it is still possible to discuss a feature of a specific set of contact events where all events are the specific set are metal-ion-depositing—however, it is understood that additional contact events may be performed before and/or after and/or after a time-frame of the 'specific set of contact event.s'

Figure 24:
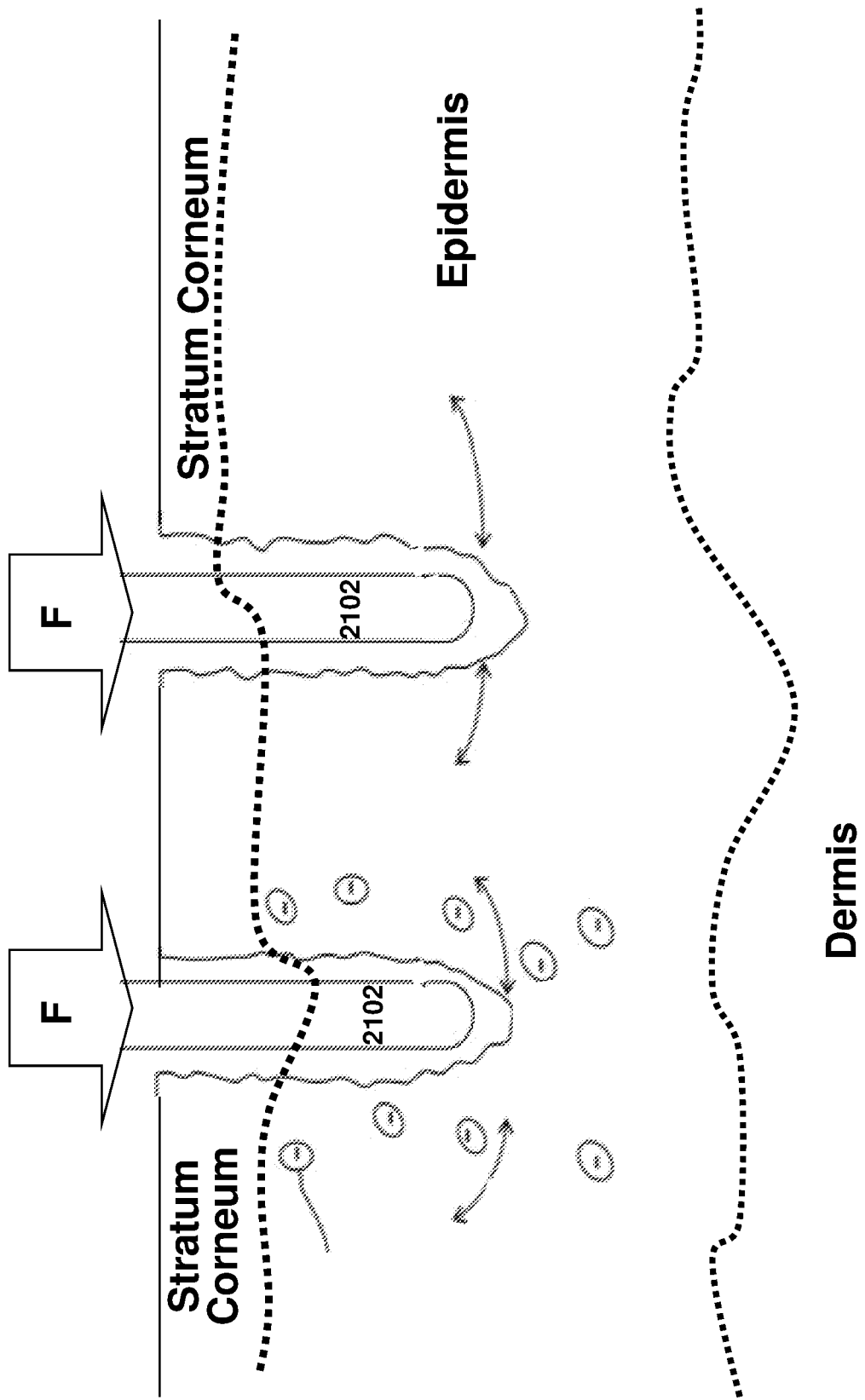
FIG. 24 illustrates a contact-event between electrodes and skin (e.g. of the scalp) wherein the electrodes do not penetrate into the dermis and ions are deposited on the skin (e.g. of the scalp).

In the example of FIG. 24, the electrodes 2102 are 'non-wounding' since they do not enter the dermis. The rounded tips of the electrodes allows the user to provide significant pressure (e.g. at 0.5 mega-Pascal) to achieve a less invasive but sufficiently-stimulating 'micromassage' effect rather than a wounding or dermis-penetrating effect.

In the example of FIG. 24, negatively-charged ions are deposited on the skin to create the metal-ion-deposition island.

Figure 25:
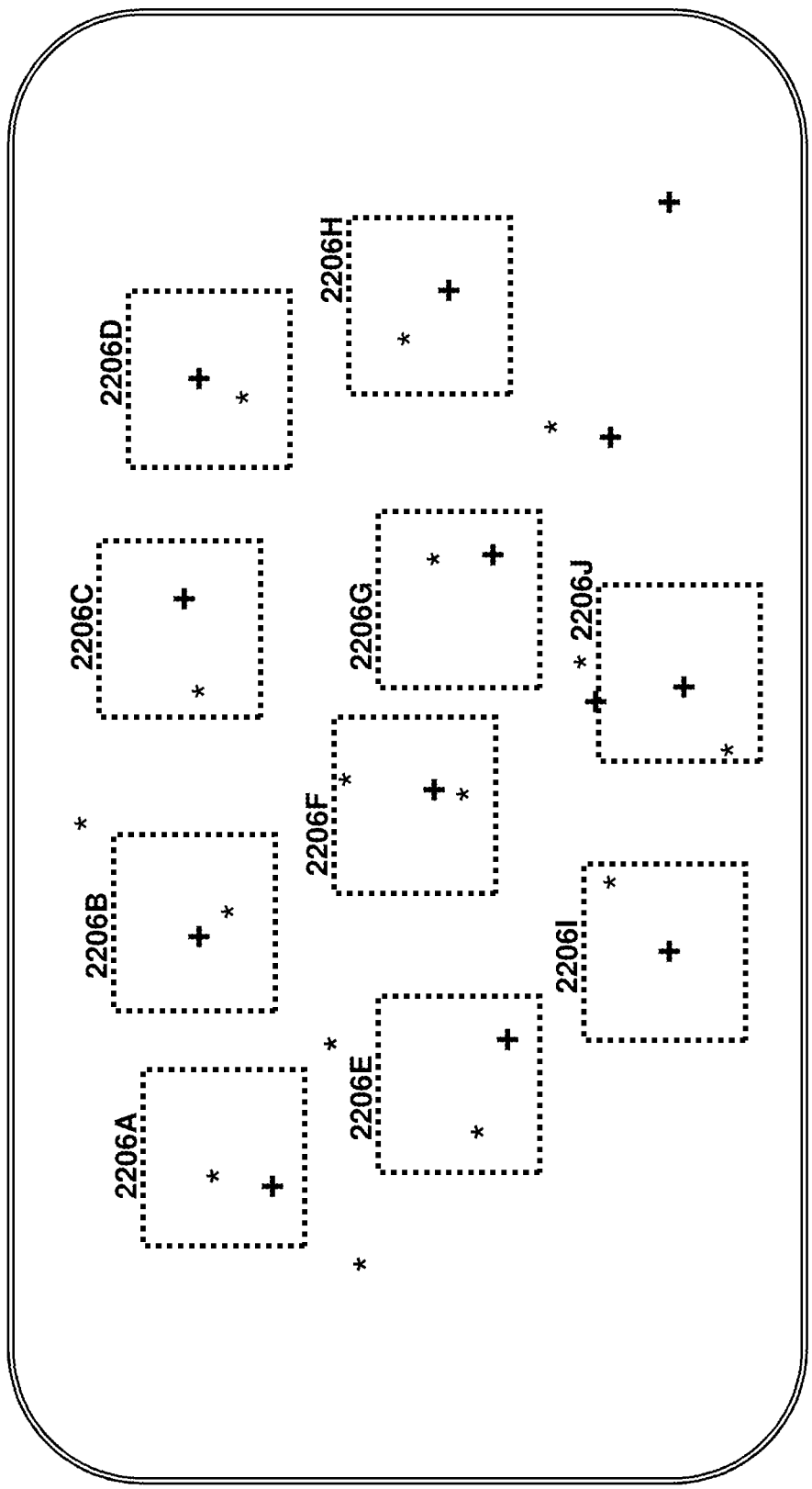

FIG. 22 illustrates on pattern of metal-ion-deposition islands. FIG. 25 illustrates another pattern. In the example of FIG. 25, a region of scalp comprises a plurality of different square 'patches' 2206 (patches 2206A-206J are illustrated) where a patch is a geometric construct to describe a portion of scalp. For example, a size of each scalp patch may be n mm×n mm where a n is a positive number having a value of at most 5. In the example of FIG. 25, cation and anion metal-deposition islands are both respectively applied to each patch of the ten patches.

Thus, it may be said that at least one first-metal-deposition-island (i.e. represented by a '+') and at least one second-metal-deposition-island (i.e. represented by a '*') are both respectively and distinctly formed on each n mm×n mm scalp scalp-patch 2206 selected from a 10-member scalp-patch sub-set of the scalp-patch set.—for example, the 10 member scalp patch set {2206A,2206B,2206C,2206D, 2206E,2206F,2206G,2206H,2206I,2206J}.

The term 'metal-ion-deposition' island refers to deposition of metal on the user's scalp such that at the moment of deposition, the metal is deposited as an ion. There is no requirement for the metal to remain in ionic form thereafter. A metal-ion-deposition island forms a localized portion of metal on the user's scalp.

Examples described above relate to deposition by a multi-disc roller. Alternatively or instead of using disks, the electrodes may protrude from a single solid roller (e.g. spherical or cylindrical). In one example, electrodes are disposed at different longitudinal positions along the roller. As discussed below, the method may be performed using a non-roller device.

Also illustrated in FIG. 17 are axle 2112, handle 2114, housing 2110, and power-source 2116.

Although some electrode-scalp contact events form metal-deposition-islands, not every contact event is required to deposit metal on the user's scalp.

Example Performance Parameters

One non-limiting use case relates to the following parameters: (i) a disc radius of 16 mm and circumference of about 100 mm; (ii) about 100 protrusions per disc so that a distance between neighboring protrusions along a disk circumference is about 1 mm; (iii) the user applies pressure (e.g. at least 0.5 mega-Pascal or at least 1 mega-Pascal per electrode) has he/she rolls the disc array over his/her scalp, and thus rolls the disc area at a rate of about 0.3 revolutions/second corresponding to a linear velocity, assuming.

Assume a 2-disk device, the number of distinct contact events per second (i.e. where a protrusion is brought into and out of contact with the scalp) in this example is about $0.3*100*2 \approx 65$ contact-events per second. In this situation, assuming the user continuously rolls the disc over his/her scalp for at least one minute, the scalp would be subjected to about 4000 electrode-scalp contact events per minute.

Assuming an 8-disk device, the user's scalp would be subjected to about 16,000 contact events per minute.

- Cross sectional area of individual electrode-scalp contact-location and/or metal-deposition island: In an exemplary embodiment of the invention, the cross sectional area of an electrode-scalp contact location is selected to be, for example, about 1 mm$^2$, about 0.1 mm$^2$, about 0.01 mm$^2$, about 0.001 mm$^2$, about 0.0001 mm$^2$, or other smaller, intermediate or larger sizes are used.
- Density: In an exemplary embodiment of the invention, the density of contact locations and/or deposition islands per unit area of scalp to be treated is selected, for example, about 1 locations/mm$^2$, about 5 locations/mm$^2$, about 8, locations/mm$^2$ about 10 locations/mm$^2$, or other smaller, intermediate or larger densities are used.
- Total electrode-scalp contact area per electrode per contact event: In an exemplary embodiment of the invention, the area of scalp to be subjected to ion-deposition from the total area of the scalp to be treated is selected. The 'fill factor' is selected to be, for example, about 10%, about 1%, about 0.1%, about 0.01% of the area to be treated, or other smaller, intermediate or larger values are used. In one non-limiting example, the fill factor is (i) at least 5% or at least about 7.5% and/or (ii) at most 50% or at most 40% or at most 30% or at most 20% or at most 15%.
- Gaps between deposition islands: In an exemplary embodiment of the invention, the distance between deposition-islands is selected. Optionally, the space between deposition-islands along a first axis is selected. Optionally or additionally, the space between deposition-islands along a second axis is selected, for example, the first and second axes are perpendicular to one another. In some embodiments, gaps along at least one axis are selected according to the existing amount of hair at the area to be treated, for example, relatively larger spaces are selected for a region with relative denser hair and/or hair having a relatively larger diameter. Existing hair may be displaced to the gaps between the deposition-islands. Spaces between deposition islands along the first axis are selected to be about, for example, 3 mm, about 4.5 mm, about 6 mm, or other smaller, intermediate or larger spaces are used. Spaces between electrode deposition islands along the second axis are selected to be, for example, about 0.3 mm, about 0.5 mm, about 1 mm, about 1.5 mm, about 2 mm, or other smaller, intermediate or larger values are used FIGS. 16A-16B are sides view of a electrode array 2604 using electrodes 2600 to cause a pattern of deposition islands in the scalp 2606.

Figure 26A:
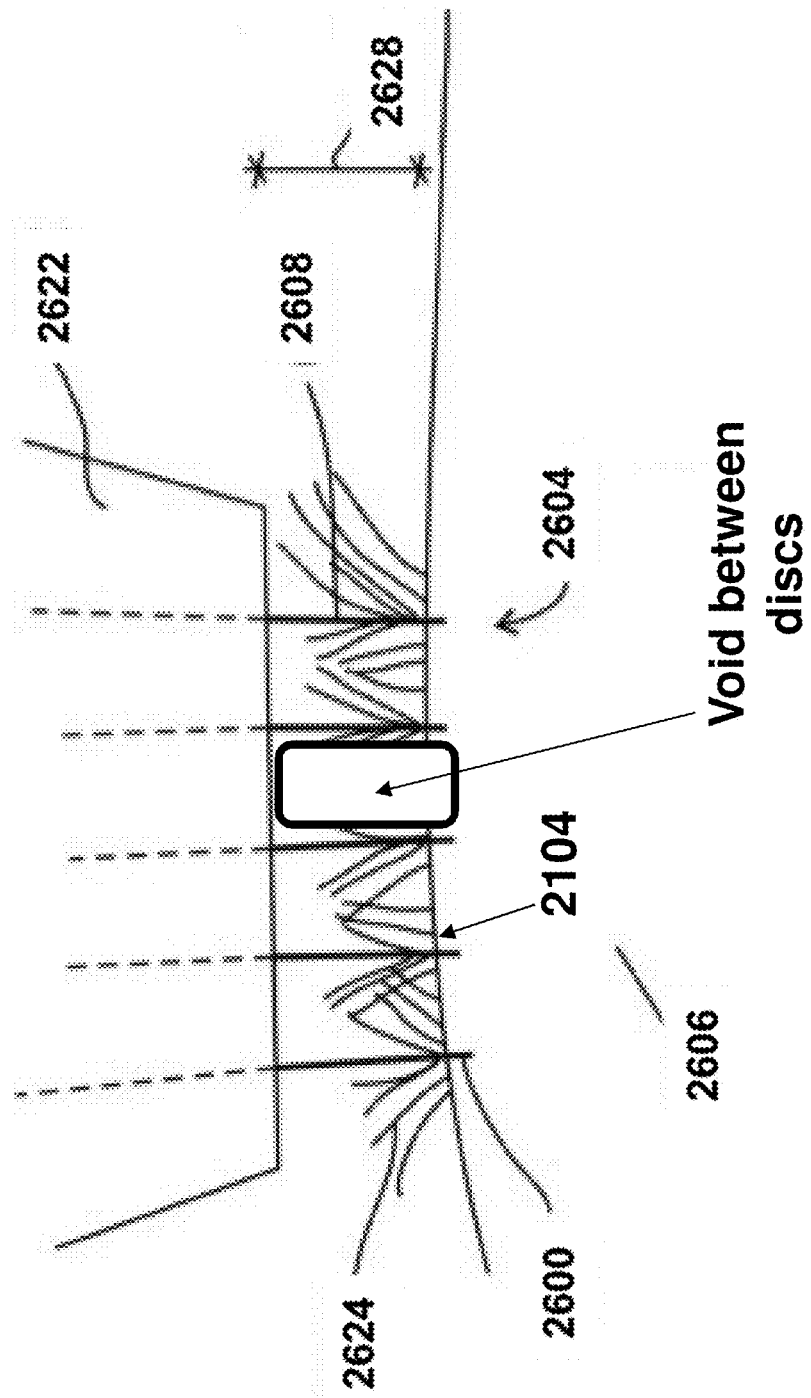

Also illustrated in FIG. 26A are voids between disc—this allows the discs to penetrate through the hair 2624—i.e. when the discs penetrate through the hair, the hair is located in the voids between the discs.

In an exemplary embodiment, an actuator moves the electrode up and/or down.

In some embodiments, a group of electrodes is attached to a single actuator.

In an exemplary embodiment of the invention, a distance 2626 and/or 2628 between scalp 2606 and device head 2620 and/or 2622 is set to provide a volume for hair 2624 during penetration of electrodes 2600 through the hair to contact scalp 2606. Hair 2624 can be displaced into the volume to let electrodes 2600 contact scalp 2606 to allow the full length of electrodes 2600 to enter. Distance 2628 can be set for example, by diameter of discs 2608 and/or by selecting the central hinge position within device head 2620.

In an exemplary embodiment of the invention, the pattern of deposition-islands is parallel straight lines, for example, for a roll of discs 2608. Optionally, complex and/or random patterns of deposition islands can be created by repeated rolling of discs 2608 over the scalp. Optionally, one or more discs each comprise multiple electrodes, arranged, for example, in a circumferential arrangement and/or along the thickness of the wheel, on the surface contacting the skin.

In an exemplary embodiment of the invention, electrodes 2600 are made out of a biocompatible material, non-limiting examples include; metals (e.g., steel, silver, gold), alloys, glass, plastic, ceramic.

In an exemplary embodiment of the invention, electrodes 2600 are coated with a type I 5a-reductase inhibitor, for example the metals zinc and/or copper.

It is noted that a series of discs disposed along a common rotation axis (see FIGS. 18, 26A) is just one example of a 'roller' having protrusions extending therefrom (e.g. ion-releasing and/or electrode-protrusions). For the case of the series of discs, each disc has substantially the same diameter so that the protrusions extended radially/outwardly from a common 'geometric-construct cylinder' that, for example, rotates at a common rotation rate (e.g. individual discs rotate in-tandem). This the series of discs is one example of a 'cylindrical roller.'

Figure 26B:
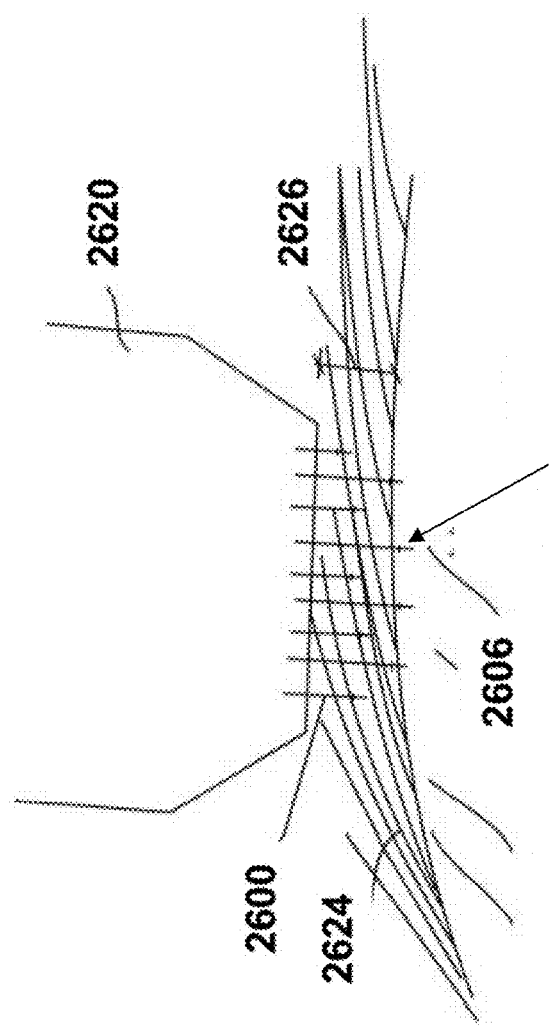
Figure 26C:
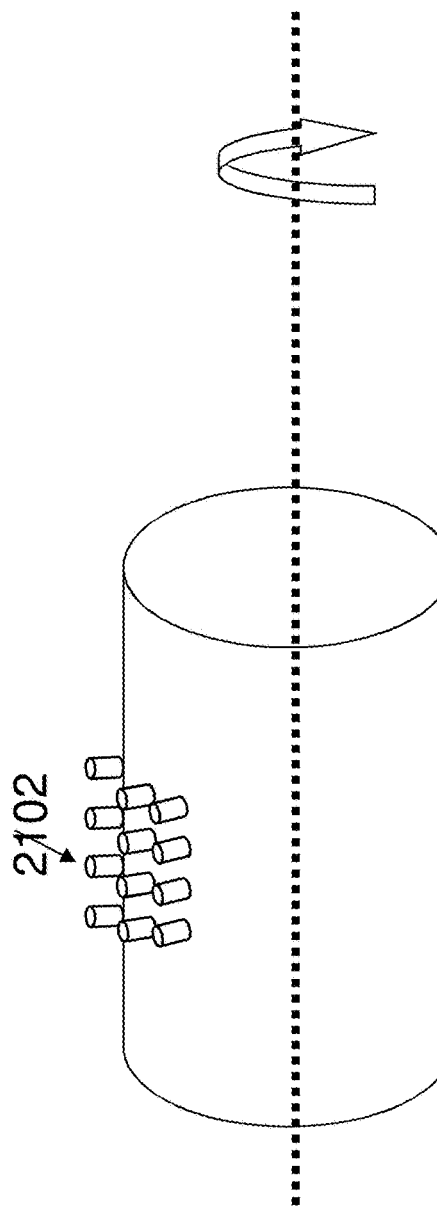

Another example of a cylindrical roller is illustrated in FIG. 26B—typically the protrusions would be distributed around a circumference of the roller as was the case for the disks—the fact that only a few protrusions as illustrated in FIG. 26C is for brevity, and is not meant to represent the typical case.

Figure 26D:
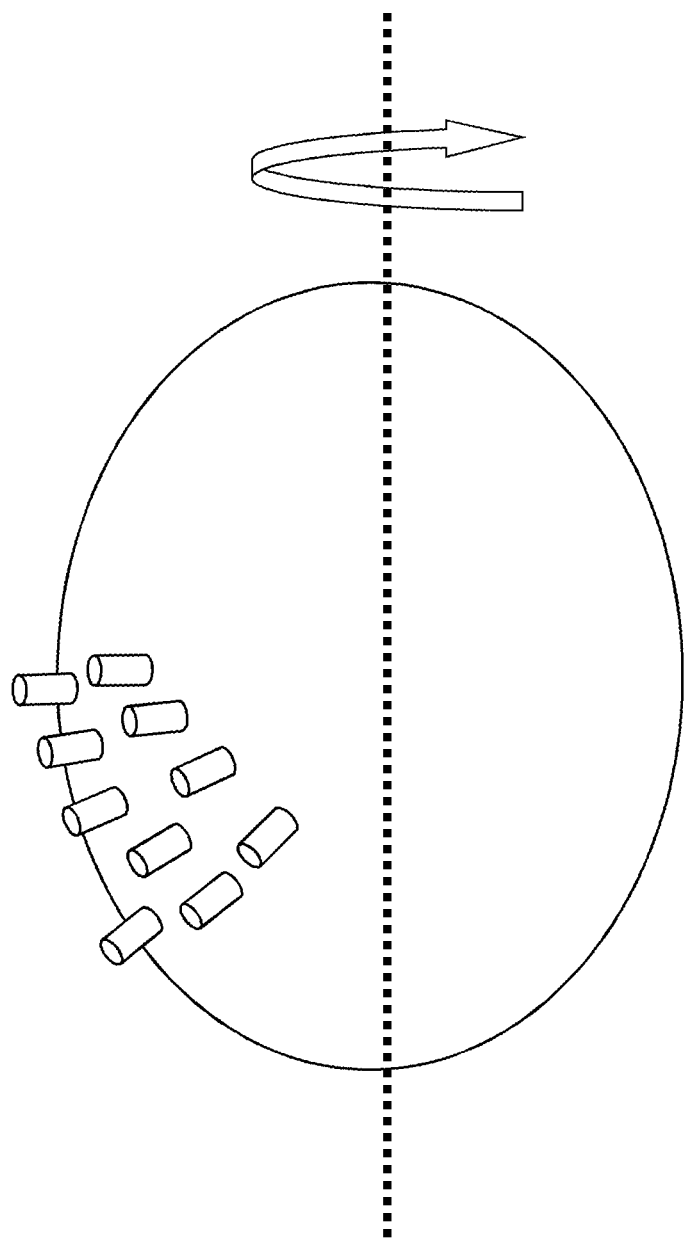

A cylindrical roller is one example of a 'round roller'—other examples may be a spherical roller shaped like an 'American football' illustrated in FIG. 26D.

Electrode/Protrusion Actuators

FIGS. 27A-27F are illustrations of embodiments of electrode actuators, in accordance with some embodiments of the invention. Optionally, electrode actuators act as vibrational elements, to vibrate electrodes according to the selected vibrational protocol.

In some embodiments of the inventions, one or more non-limiting examples of actuators include; piezoelectric elements, motorized linear actuators, and/or shape memory alloy actuators.

In some embodiments of the invention, electrodes are individually vibrated. Alternatively or additionally, groups of electrodes are vibrated together. Optionally, vibration is performed by an off-axis spinning mass, for example, the direction of the axis determines the plane of vibration. For example, translating the movement to a linear direction, pushing on a piston mass creates a linear vibration.

FIG. 27A is an isometric view, and FIG. 27B is a cross sectional view of a electrode array 2702, for example described with reference to FIG. 27B. Each electrode 2700 (of array 2702 is coupled to an actuator 2704. Optionally, each electrode 2700 is coupled to a separate actuator 2704. Optionally, actuators 2704 are attached to a power control 2705.

For example, the actuators 2704 may be controlled to maintain the electrode in contact with the scalp for only brief electrode-scalp contact events.

FIG. 27C is an isometric view, and FIG. 27D is a cross sectional view of a electrode array 2706. Two or more electrodes are controlled by actuators, for example, array of nine electrodes 2708 is controlled by actuator 2710 and, for example, array of electrodes 2706 is controlled by actuator 2711. There are two or more groups of electrodes, for example, four groups 2708, 2730, 2732 and 2734 of nine electrodes in each group are controlled by four actuators 2710, 2736, 2738 and 2740.

Electrode groups can be arranged in a variety of patterns. Non-limiting examples include the checkerboard pattern as illustrated in FIG. 27D, a bull's eye pattern as illustrated in FIG. 27E and/or a side by side tile pattern as illustrated in FIG. 27F. For example, the bull's eye pattern (FIG. 27E) may comprise one electrode 2715 in an inner circle and at least two electrodes in electrode array 2717 in an outer circle and, for example, the side by side tile pattern (FIG. 27F) may comprise eight groups 2721, 2722, 2723, 2724, 2725, 2726, 2727 and 2728 of electrodes.

In some embodiments, at least two groups (FIG. 27F) may touch the scalp simultaneously. For example, the device is configured so that several actuators receive a signal to "lower" and touch and/or penetrate the scalp simultaneously. Optionally or alternatively, several electrodes are connected to a single actuator 2710 and go up and down together. Optionally, the electrodes conform (or are advanced to conform) to the scalp curvature and penetrate together. In some embodiments, the electrodes are equipped with a spring to facilitate conformity to the scalp curvature.

In an exemplary embodiment, 2721 and 2722 may touch the scalp simultaneously, 2722 and 2723 may touch the scalp simultaneously, or 2723 and 2724 may touch the scalp simultaneously, or 2724 and 2725 may touch the scalp simultaneously, or 2725 and 2726 may touch the scalp simultaneously, or 2721, 2722 and 2728 may touch the scalp simultaneously, or 2722, 2725 and 2727 may touch the scalp simultaneously or another combination of groups may touch the scalp simultaneously. Optionally, more than two types of ions are discharged from the electrodes. FIG. 27G is an isometric view of a single injector.

FIG. 27H is an isometric view of a 1-dimensional array of electrodes. FIG. 27I is an isometric view of a 2-dimensional array of electrodes.

Reference is now made to FIGS. 28A-28D. In some embodiments, the number of ions deposited during treatment is controlled by adapting the voltage (see, for example, the methods described in Chizmadzhev et al, *Electrical Properties of Skin at Moderate Voltages: Contribution of Appendageal Macropores*), by adapting the temperature (see, for example, the methods described in Maulsby et al, *The interrelationship between the galvanic skin response, basal resistance, and temperature*), and/or by adapting the frequency. Increasing the voltage, temperature and frequency can each increase the number of ions deposited. For example, the number of ions deposited during treatment is controlled in an open loop manner by determining the voltage before beginning treatment. Alternatively, the number of ions deposited during treatment is controlled in a closed loop manner by determining the voltage during the treatment based on feedback received from sensors incorporated into the device.

In some embodiments, controlling the ions deposited is done directly by measuring the charge of each polarity (ion type) or of both, for example, by measuring and integrating the (absolute) current passed through each type of disk set or through both. The existence of current indicates the unit is in actual use. A degradation of current indicates a faulty unit, improper contact, or other means. Excessive current might indicate a faulty unit, or excessive moisture on the scalp (and therefore not enough current through the scalp).

In some embodiments, the mass of metal ions discharged from the electrodes may be calculated by a formula. For example, assuming the charge C is ionic, and the oxidation state Z, the mass m of metal ions discharged from the electrodes (w is the atomic mass, e the electron's charge, Na is Avogadro's number) is computed as follows:

$$m = \frac{C \cdot w}{e \cdot Z \cdot N_a}$$

In some embodiments, ion injecting electrodes that touch the scalp are connected to one terminal of a power source and an electrode that does not touch the scalp is connected to a second terminal of the power source. For example, the electrode that does not touch the scalp may be connected to a part of the body other than the scalp. For example, the device may comprise a handle comprising an electrode designed to touch the palm of a person holding the handle.

In some embodiments, the efficiency of the deposition of ions is enhanced, for all users or for a specific user, by performing a "calibration phase" in which the same region is treated for a period of a time while changing each parameter slightly and measuring the real-time response in current. Optionally, different treatment parameters may be chosen for different scalp areas of same user. Optionally, different treatment parameters may be chosen for different users.

In some embodiments, the efficiency of the deposition of ions is enhanced through general improvements in the parameters, for example, preparing a better cross section of the electrodes and/or starting with more efficient voltage and frequency. Optionally, the efficiency of the deposition of ions is enhanced through dynamic modification of changeable treatment parameters through closed-loop feedback/control.

In some embodiments, ion penetration increases blood flow when the electrical fields generated by the small charge deposits create a MENS (microcurrent electrical neuromuscular stimulation) effect in the skin. Optionally, the MENS effect shortens skin healing times. Optionally, the electrical fields invigorate movement of essential ions and stimulate the skin systems into an increased rate of activity.

FIG. 28A is an illustration of an array of electrodes 2802 depositing materials 2804 beneath the skin 2806 surface of scalp, in accordance with an exemplary embodiment of the invention. For simplicity purposes, array 2802 comprises four electrodes 2808, having the material 2804 to deposit located at the part of the electrode 2808 that contacts scalp 2806.

In an exemplary embodiment of the invention, electrodes 2808 are made of material 2804. Alternatively, electrodes 2808 are coated with material 2804. Optionally or alternatively, 2830, 2832, 2834 and/or 2836 represent electrical potentials which may exist on electrodes 2808.

In an exemplary embodiment of the invention, two different electrodes 2808 to be electrically coupled have two different materials 2804 at their ends. For example, alternating discs (e.g., as illustrated in FIG. 17) are made from different materials, for example, copper and zinc.

In some embodiments, scalp 2806 acts as a bridge, placing two electrodes having dissimilar metals in electrical contact. The metals can undergo galvanic corrosion, where one metal dissolves in scalp 2806, while the other metal absorbs ions from scalp 2806. For example, if one metal is zinc and the other metal is copper, the zinc will dissolve and the copper will accumulate. Optionally, material 2804 is chosen to have other depositing effects. Optionally or additionally, current is forced in the opposite direction.

FIG. 28B is an illustration of ion deposition into scalp 2806 for example using a galvanic cell set-up, in accordance with an exemplary embodiment of the invention. Optionally, a power source 2812 electrically couples a first electrode 2814 and a second electrode 2816. For example, each electrode 2814 and 2816 may be coated electrodes comprising different materials at the ends 2815 and 2817, for example, electrode 2814 touches scalp 2806 at end 2815 with zinc and electrode 2816 at end 2817 with copper. Optionally, power source 2812 emits Alternating Current (AC). Optionally, power source 2812 emits Direct Current (DC).

Figure 28D:
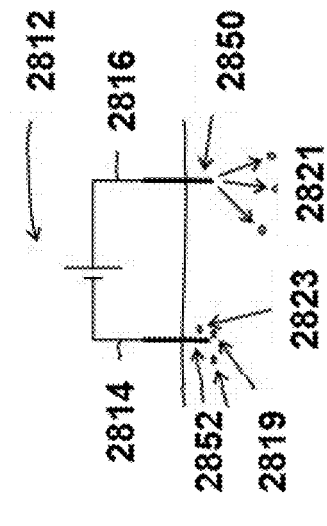
Figure 28C:
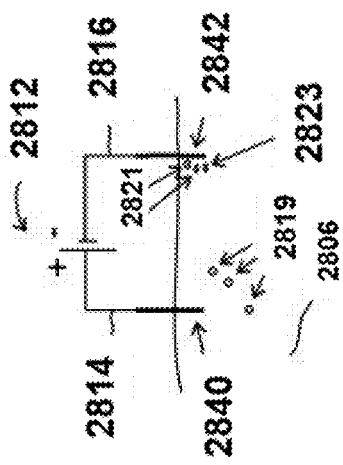
Figure 29B:
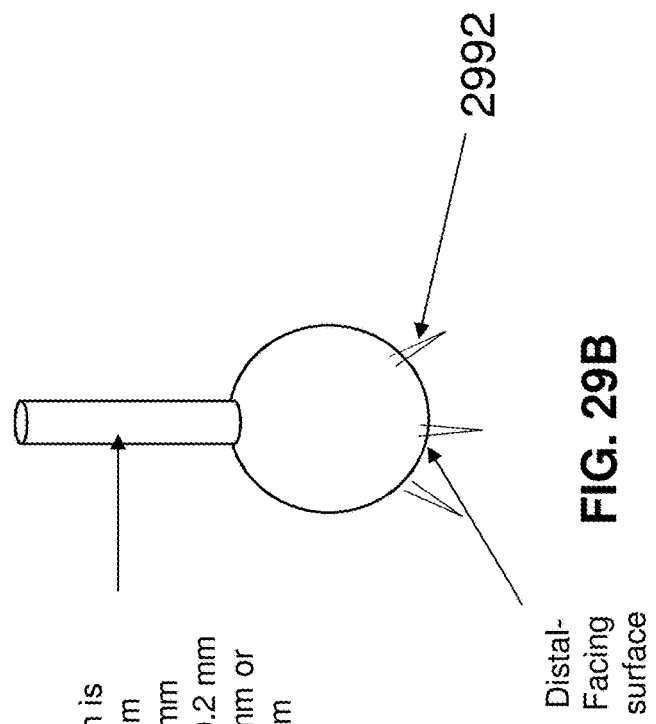
Figure 29A:
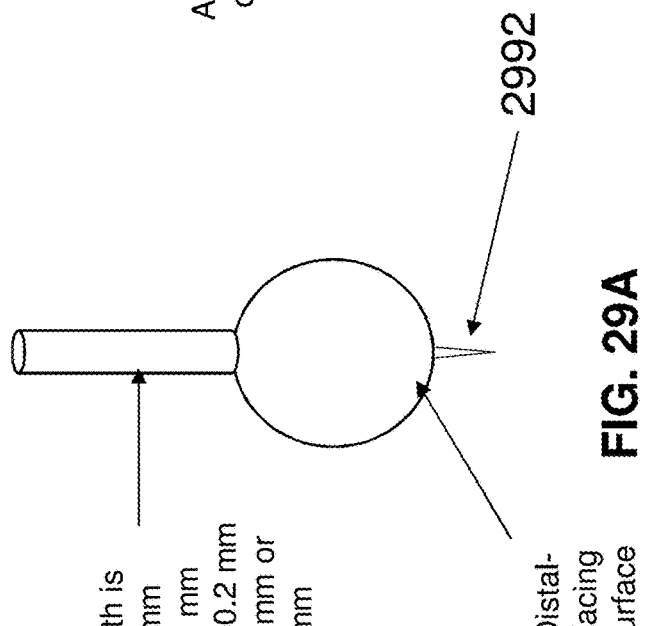

FIG. 28C is an illustration of using the set-up as in FIG. 28B to release zinc ions into scalp 2806, in accordance with an exemplary embodiment of the invention. The positive pole of power source 2812 is electrically connected to electrode 2814 with zinc (e.g., acting as the anode 2840), and the negative pole is electrically connected to electrode 2816 with copper (e.g., acting as the cathode 2842). Zinc ions 2819 are discharged from electrode 2814 into scalp 2806, and copper ions 2821 and/or other ions 2823 are accumulated from scalp 2806 onto electrode 2816.

In an exemplary embodiment of the invention, the voltage of power source 2812 as in FIG. 28C is, for example, about 1V, about 3V, about 5V, about 7V, about 10V, about 30V, or other smaller, intermediate or larger values are used.

FIG. 28D is an illustration of using the set-up of FIG. 28B to release copper ions into scalp 2806, in accordance with an exemplary embodiment of the invention. The positive pole of power source 2812 is electrically connected to electrode 2816 with copper (e.g., acting as the anode 2850), and the negative pole is electrically connected to electrode 2814 with zinc (e.g., acting as the cathode 2852). Copper ions 2821 are discharged from electrode 2816 into scalp 2806, and zinc ions 2819 and/or other ions 2823 are accumulated from scalp 2806 onto electrode 2814.

In an exemplary embodiment of the invention, the voltage of power source 2812 as in FIG. 28D is at least greater than the standard potential for the reaction, for example, above 1.10 Volt.

In an exemplary embodiment of the invention, power source 2812 is an alternating current source. The frequency of source 2812 can be selected to result in a desired ion deposition pattern, for example alternating between the set-ups as described in FIGS. 28C and 28D. For example, the frequency of source 2812 is selected to be substantially half of the rate of electrode-scalp contact events per second, for example when using the hair stimulation device with rolling discs, for example, as described with reference to FIG. 17. For example, if the device is rolled over the scalp to achieve a rate of scalp-electrode contact events of 30 events per second and the frequency of source 2812 is 15 Hz, the ions deposited during each electrode-contact will alternate, for example between copper and zinc. Furthermore, different ions will be deposited at different locations.

In some embodiments of the invention, the AC waveform (e.g., duty cycle) is selected according to the ratio of the desired material deposition. For example, to achieve a 10:1 ratio (e.g., of zinc:copper), a waveform having a 10:1 ratio (91% duty cycle) is selected. Alternatively or additionally, the number of electrodes coated with each material is selected according to the desired deposition ratio, for example, the number of electrodes coated with zinc relative to the number of electrodes coated with copper is 10:1.

In some embodiments of the invention, power source 2812 is a direct current source. The polarity of source 2812 can be selected to result in a desired ion type and/or deposition pattern. For example, according to the set-ups of FIGS. 28C and/or 28D. The set-up of FIG. 28C can also be achieved without source 2812, for example by electrically connecting electrodes 2814 and 2816.

In some embodiments of the invention, materials (e.g., ions) are added directly to the scalp, for example in the form of a lotion, gel and/or water. Non-limiting examples of ions in this form include $ZnSO_4$, $CuSO_4$. The lotion can be added in addition to the use of coated electrodes, or instead of coated electrodes (e.g., using uncoated electrodes). Optionally, the ions penetrate below the surface of the skin.

Electrical Stimulation

In an exemplary embodiment of the invention, the scalp is stimulated by applying one or more currents and/or voltages to areas of the skin, for example, an electrical stimulation protocol is selected. Optionally, a plurality of currents and/or voltages are applied to the scalp, for example different voltages and/or currents to different areas and/or between different electrodes.

In an exemplary embodiment of the invention, the electrical stimulation is separate from the current applied to the electrodes to release ions, for example, Optionally, electrical stimulation is applied by one or more discs and/or electrodes, and ion deposition is applied by different discs and/or electrodes. Optionally, the electrodes to apply electrical stimulation but not ion deposition are inert, for example, made from platinum. Alternatively, a voltage is applied to the electrodes to prevent ion deposition by the galvanic effect. Alternatively or additionally, electrical stimulation and ion deposition overlap, for example, applied by the same discs and/or electrodes.

Inventors hypothesize that selectively applying a plurality of electrical stimulation patterns (e.g., voltages and/or currents) to the scalp will promote hair growth. However, the efficacy of some embodiments of the invention can be unrelated to the underlying theory, and work even if the theory is incorrect.

In an exemplary embodiment of the invention, the electrical stimulation protocol comprises one or more variables. Non-limiting examples of selectable parameters include:

Geometric voltage and/or current distribution pattern: The pattern of applied voltages and/or current per electrode. For example, the voltage and/or current at each electrode is independently controlled and/or groups of electrodes have similar voltages and/or current (e.g., alternating electrodes have similar voltages and/or currents, electrodes having the same type of material (for example zinc or copper) have similar voltages and/or currents).

In some embodiments of the invention, the voltage and/or current pattern is substantially the same, for example, the same electrode is associated with the same charge and/or current. Alternatively or additionally, the voltage and/or current pattern is dynamic, for example dynamic throughout the array, and/or a region of the array. For example, in a relatively large array, a relatively small patch of the electrical pattern can be scanned across the array.

A potential advantage of two groups of electrodes with different voltages is the controlled patterning of current and/or ion deposition. For example, local stimulation may be superior to global. Potentially, division to several groups allows greater flexibility and/or controllability of the current. For example, current can be applied (e.g., to different groups, at different intensities) simultaneously or in a time-divided manner Voltage and/or current distribution pattern over time: The pattern of applied voltage and/or current per electrode can vary over time. For example, an alternating current and/or voltage can be applied to vary the voltage and/or current between two or more electrodes (or groups of electrodes). In the case of using the device with discs for example in FIG. 1 (e.g., rolling the discs with electrodes on the scalp), selecting an alternating frequency that is less than the frequency of rotation can result in increasing the diversity and/or gradients of voltages and/or currents applied underneath the skin surface. Inventors hypothesize that applying various patterns of voltage and currents to the skin stimulates hair growth. Potentially, applying varying time and/or location stimulations improves stimulation of local points, for example hair follicles Direct current (DC) offset: A voltage offset can be applied to the pattern applied to one or more electrodes. In an exemplary embodiment of the invention, the DC offset is calibrated, for example, from −3 volts to +3 volts, or other smaller, intermediate or larger values are used. In an exemplary embodiment of the invention, the DC disc to disc relative voltage ranges, for example, from 0 to 30 volt, or other smaller, intermediate or larger values are used.

Alternating current (AC) peak to peak voltage: In an exemplary embodiment of the invention, the peak to peak voltage of the AC varies, for example, from −10 volts to +10 volts, or other smaller, intermediate or larger values are used.

Frequency of AC: In an exemplary embodiment of the invention, the frequency of AC ranges, for example, from 10-1000 Hz, or other smaller intermediate or larger values are used.

Waveform of AC: In an exemplary of the invention, the waveform of AC is rectangular. Alternatively, other waveforms are used, non-limiting examples include sinusoidal, triangular, sawtooth.

Maximal Current: In an exemplary embodiment of the invention, the total electrical current is less, for example, than 0.5, less than 1, less than 2 milliAmperes, or other smaller, intermediate or larger values are used.

A Discussion of FIG. 29A-29D—Protrusions Designs to Penetrate Only a Short Depth of the Skin In some embodiments, the protrusions 2102 are designed to regulate a depth of skin-penetration during use—e.g. so the skin is penetrated to a depth of least 5 microns or at least 10 microns and/or at most 100 microns or at most 75 microns or at most 50 microns or at most 20 microns. This may be the penetration during 'ordinary use' and/or when a tip of the electrode-protrusion is pressed against a healthy human scalp at a pressure of between 0.1 to 5 MPa (e.g. a pressure of about 0.1 MPa or a pressure of about 0.5 MPa or a pressure of about 2 MPa or a pressure of about 3 MPa or a pressure of about 4 MPa or a pressure of about 4 MPa or a pressure of about 5 MPa)

For example, this may be at a localized electrode-scalp contact area of at mots 10 mm^2.

Examples of protrusions having this capability are illustrated in FIG. 29A-29D.

A 'greater thickness' refers to cross-section of the protrusion—there is a thickness in two orthogonal directions (i.e. orthogonal to each other and perpendicular to the longitudinal direction)—the 'greater thickness' is the greater of these dimensions.

In some embodiments, each of the protrusions comprises: (i) an electrode-protrusion main body 2994, characterized by a greater-thickness of at most 2 mm (e.g. at least 0.5 mm or at least 1 mm) and/or a length at least 0.2 mm or at least 0.5 mm or at least 1 mm, the main-body being blunt at its distal end and/or the main-body having a blunt distal-facing surface; and one or more sharp mini-needle(s) 2992 extending from the blunt distal end or the blunt distal-facing surface of the main body, the mini-needle 2992 being sharp at a distal surface thereof. In some embodiments, a length the sharp mini-needles is at least 10 microns or at least 20 microns and/or at most thereof being between 10 and 150 microns.

A Discussion of FIGS. 30-31

In some embodiments, instead of a roller a scalp-brush is provided. In the example of FIG. 30A, the base-surface is rigid, but as shown below (FIG. 31D) in some embodiments, the base-surface may be conformable—e.g. having a first configuration (top of 31D) where the protrusions are parallel to each other and a second configuration where due to conforming and/or base deformation that protrusions converge towards each other (bottom of FIG. 31D). The feature of FIG. 31D may allow the distal ends of the brush to conform to a shape of the scalp and the deformation of the base-surface may be in respond to higher pressure towards the center of the 'field of protrusions.'

As shown in FIG. 30B, in some embodiments, it is possible to drag or 'rake' the brush across the user's scalp to obtain 'streaks' instead of the ion-deposition ions discussed above.

Figure 31D:
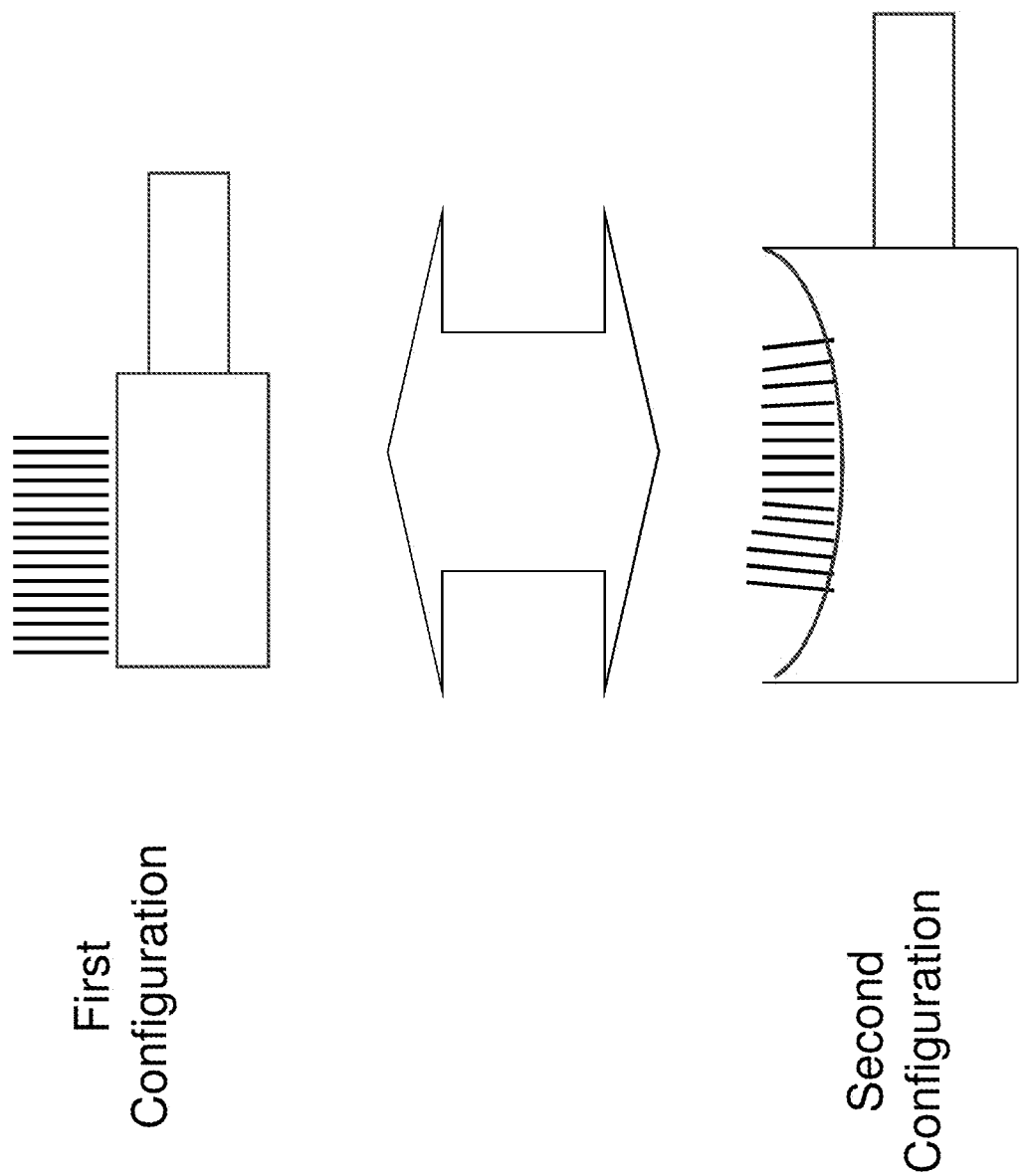

As shown in FIG. 31A-31C, it may be possible to provide a functionality similar to that of FIG. 31D (i.e. where the surface defined by the distal end of the protrusions 'conforms' to the scalp) by protrusion flexibility.

Ion-Deposition Heterogeneity (e.g. of Deposition Islands)

FIG. 25 illustrates one island-deposition pattern where there is some degree of 'deposition heterogeneity' (e.g. in two dimensions as opposed to FIG. 22 which illustrates such heterogeneity only in a single dimension).

Towards this end, it may be useful for any embodiments (e.g. brush or roller) to distribute protrusions capable of depositing different types of ions over the 'base' surface of the roller or brush.

Figure 32A:
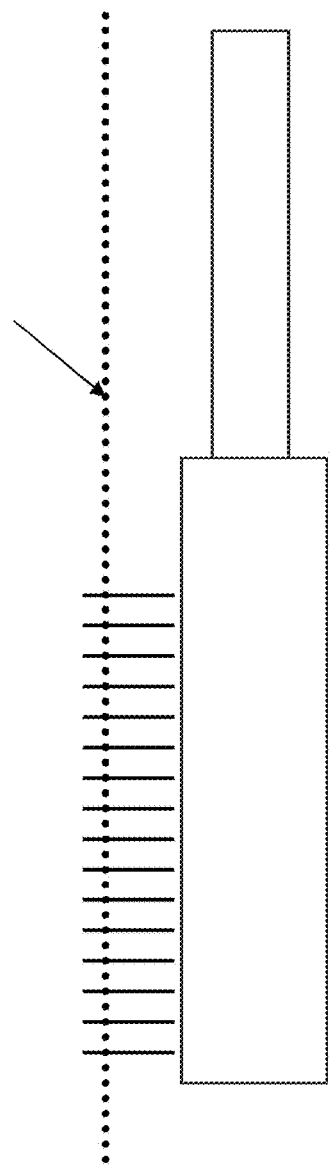
Figure 32B:
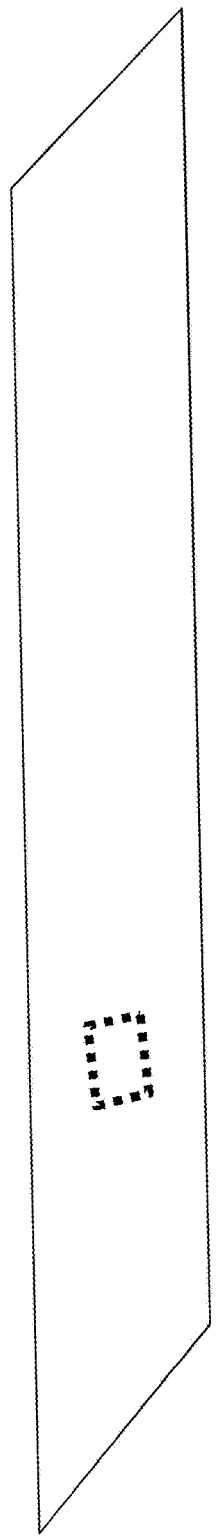
Figure 32D:
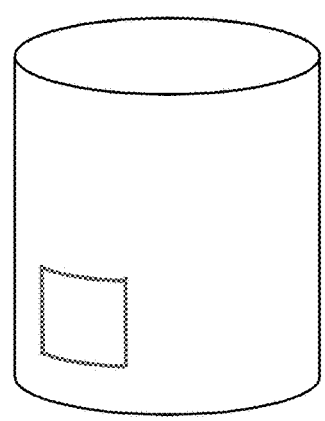
Figure 32C:
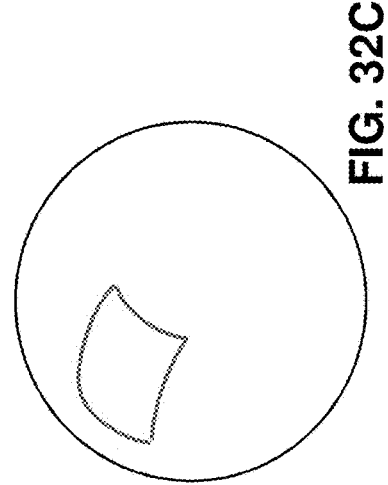

FIG. 32A illustrates a 'common plane' through which the protrusions pass. Just like it is possible to define the 'heterogeneity' in terms of island deposition on skin-patches, it is also possible to define 'heterogeneity' in terms of the capability of the ion deposition passing through a 'patch' of the 'common plane.' FIG. 32B illustrates a 'patch' for the device of FIG. 32B—for roller devices, the 'square patch' is a square in 'curvilinear coordinates' relative to a 'round common-surface' over the roller—this round common-surface' has the same shape the roller surface (i.e. the round common-surface is a geometric construct and its shape is identical to that of the roller surface—if the roller surface is cylindrical than the round common-surface is cylindrical and if the roller surface is spherical than the round common-surface is spherical). Examples of 'square patches' on the 'curvilinear' surface are illustrated in FIGS. 32C-32D.

Light-Guide

Figure 33:
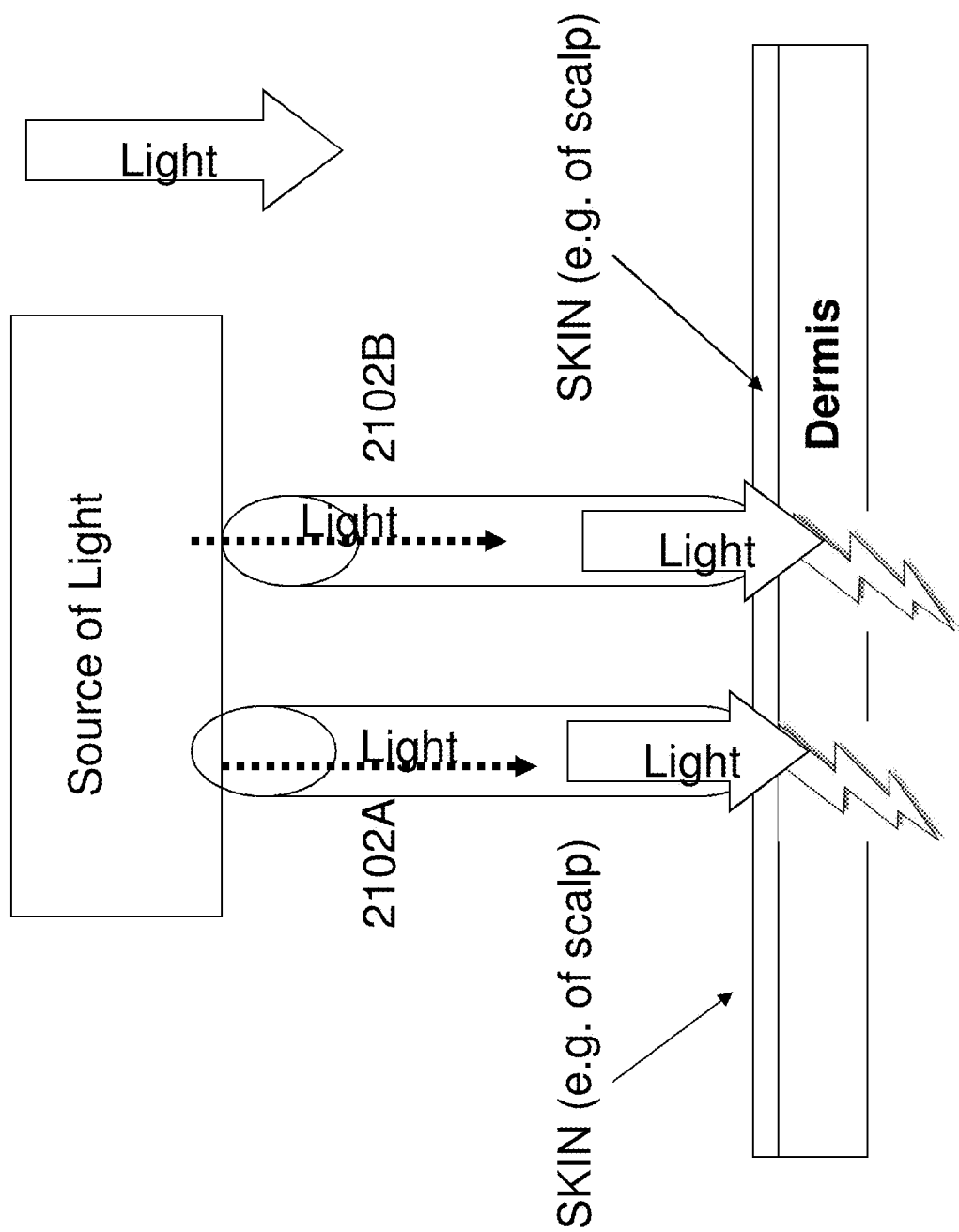

As shown in FIG. 33, in some embodiments, the electrode may be a 'hybrid electrode protrusion' for delivering both current (e.g., at least partially ionic) as well as light (e.g. through a light-guide optical properties of the protrusion).

Feedback—a Discussion of FIG. 34

Figure 34A:
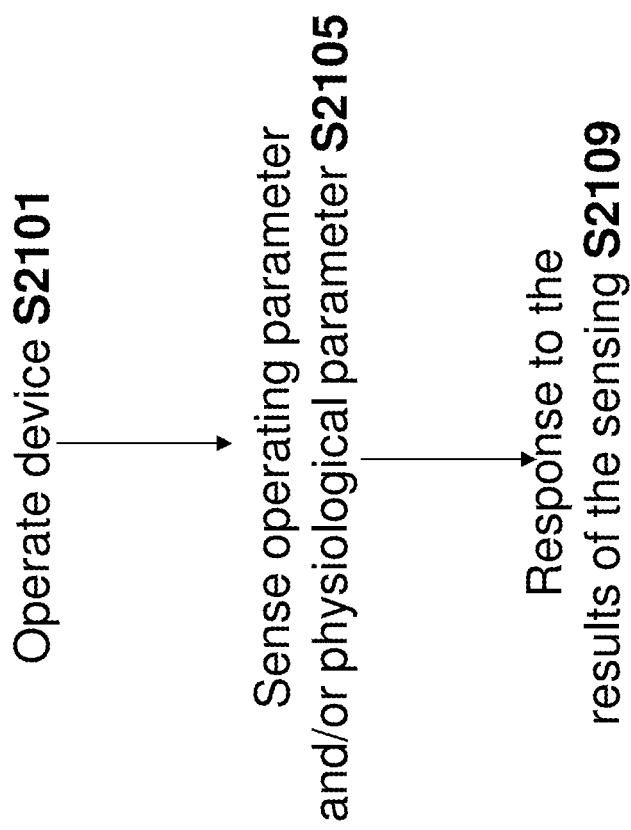
Figure 34B:
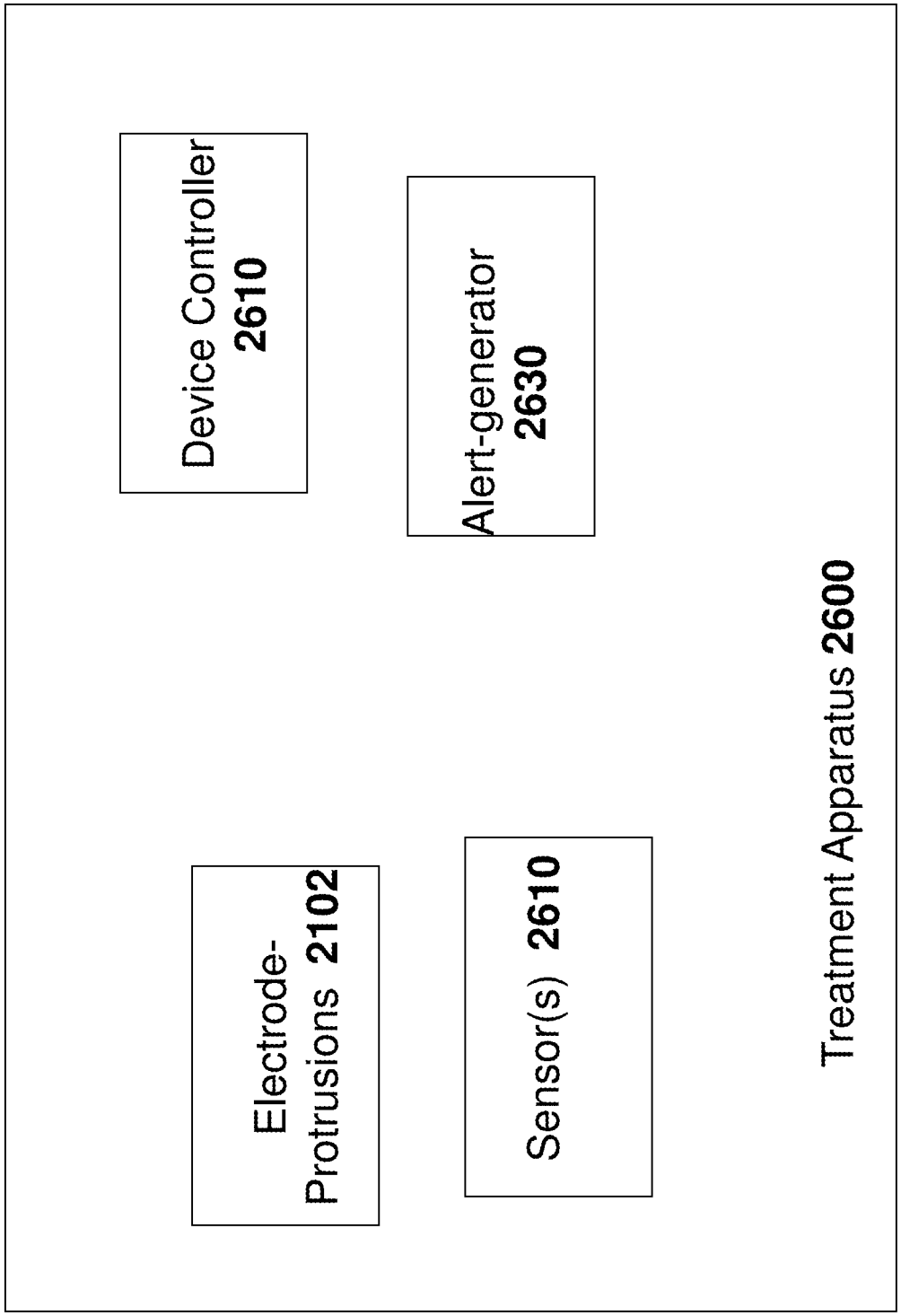

FIG. 34A is a flow chart of a method for operating a device according to feedback. FIG. 34B is a block diagram of a system for performing the method of FIG. 34.

It may be possible (step S2105) to measure an indication of how effective the treatment is—for example, to measure a rate at which ions are deposited on the scalp (greater deposition is more effective treatment) and/or an amount of current between electrodes (greater is more effective treatment) or a degree of color-change of the scalp (e.g. optically by a camera or in any other manner—greater change means irritation—more effective treatment).

If this indicator shows (step S2109) that the treatment is not effective enough it is possible to generate an alert (e.g an 'immediate alert') to encourage the user, for example, to press harder on his/her scalp with the device.

Alternatively or additionally, the device may provide the user an indication of an end of a given treatment session—e.g. by an treatment-end alert signal (e.g. audio or visual or tactile) or by shutting off the vibration, current or light. In this case, if the indications shows the treatment is not effective enough it is possible to compensate by increasing a treatment duration—e.g. the amount of time which must elapse before the treatment-end indication (e.g. alert signal or shutting off) is provide to the user.

Alternatively or additionally, it is possible to compensate by increasing a voltage applied between electrode (e.g. ion-releasing electrodes). For example, it may be possible to respond with several voltage or current pulses (e.g. brief in duration—e.g. <1 sec or <0.5 sec or <0.1 sec or <0.05 sec)

For the first case (the 'alert signal'), alert signal may be provided if the user is not pressing hard enough (even if painful)—this would encourage the user to press harder. For roller embodiments, the resistance to rolling may be increased if the user is not pressing hard enough.

In one embodiment, a 'minimum treatment effectiveness' is characterized by minimum current or ion-deposition rate or force or roll-rate (or any combination thereof).

In yet another embodiment, it is possible to optically and/or mechanically detect a presence of tangled or trapped hair (e.g. trapped in the roller or in any other device form-factor) and to respond with an alert signal.

In yet another embodiment, it is possible to regulate the 'effective sharpness' and/or 'effective penetrating ability' of the protrusion—e.g. by regulating the length of the mini-needle of FIG. 29—e.g. if the treatment effectiveness indicator is below a threshold, it may be possible to cause the protrusion to be 'effectively sharper' to compensate for too-little ion-deposition by greater penetration.

Alternatively or additionally, a scalp thickness sensor (e.g. based on ultrasound) may be provided—for thicker scalps it is possible to increase the intensity of treatment (e.g. effective sharpness and/or ion-deposition rate and/or voltage between electrodes).

FIG. 35

FIG. 35 describes one embodiment of a brush form with a vibrating plate.

In this embodiment, the brush comprises an optionally conforming base (2191) and an optionally perforated vibration plate (2193) the bristles (2192) go through. The conformation of the base allows the bristles to move up and down through the perforate vibrating plate so a maximal number of bristles are in contact with the scalp simultaneously.

The vibration plate is located 5 mm, 10 mm, 15 mm, or 20 mm below the base and above the end of bristles. It is connected to a vibrator (2194) that can vibrate it laterally. Optionally, the vibration is in each axis, optionally independently controlled per axis.

This embodiment provides effective lateral vibration to the bristle ends, while adding configurable rigidity to the teeth. The distance between the base and vibrating plate determines the rigidity of the teeth.

Various embodiments and aspects of the present invention as delineated hereinabove and/or as claimed in the claims section below find experimental support in the following examples:

Example—Experiment

Reference is now made to the following example, which together with the above descriptions illustrates some embodiments of the invention in a non-limiting fashion. In particular, features described below may be used without other described features and in conjunction with methods and/or apparatus as described above.

Material and Methods—

An experiment over 2-4 months was conducted on 26 volunteers all of whom were suffering from baldness. Each volunteer was provided with a roller-like device (see, for example, FIG. 17) configured to form both zinc-ion-deposition islands and copper-ion-deposition islands when rolled over the scalp. As the user rolled the device over his respective scalp, electrodes of the roller device were each briefly brought into contact with and out of contact with the scalp. The device used included 8 disks with non-puncturing electrode protrusions, used for several minutes at least twice a week by users.

Each disk had about 100 protrusions, about 0.2 mm wide and a triangular protrusion with effective contact length of 1 mm (tip is about 0.1 mm)

Disks were alternatively coated with Zinc and Copper.

Electrical current applied was about 30V at 40 Hz.

No LLLT was applied.

For each subject, it was possible, per treatment site, to monitor a number of features related to hair density at the treatment site, such as the overall hair density, terminal hair-density and non-terminal hair density. Results are summarized in FIGS. 33A-33B. The skilled artisan who reviews FIGS. 33A-33B will appreciate that the device and method appeared to play a significant roll in reversing hair-loss.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

Additional Discussion

Figure 36:
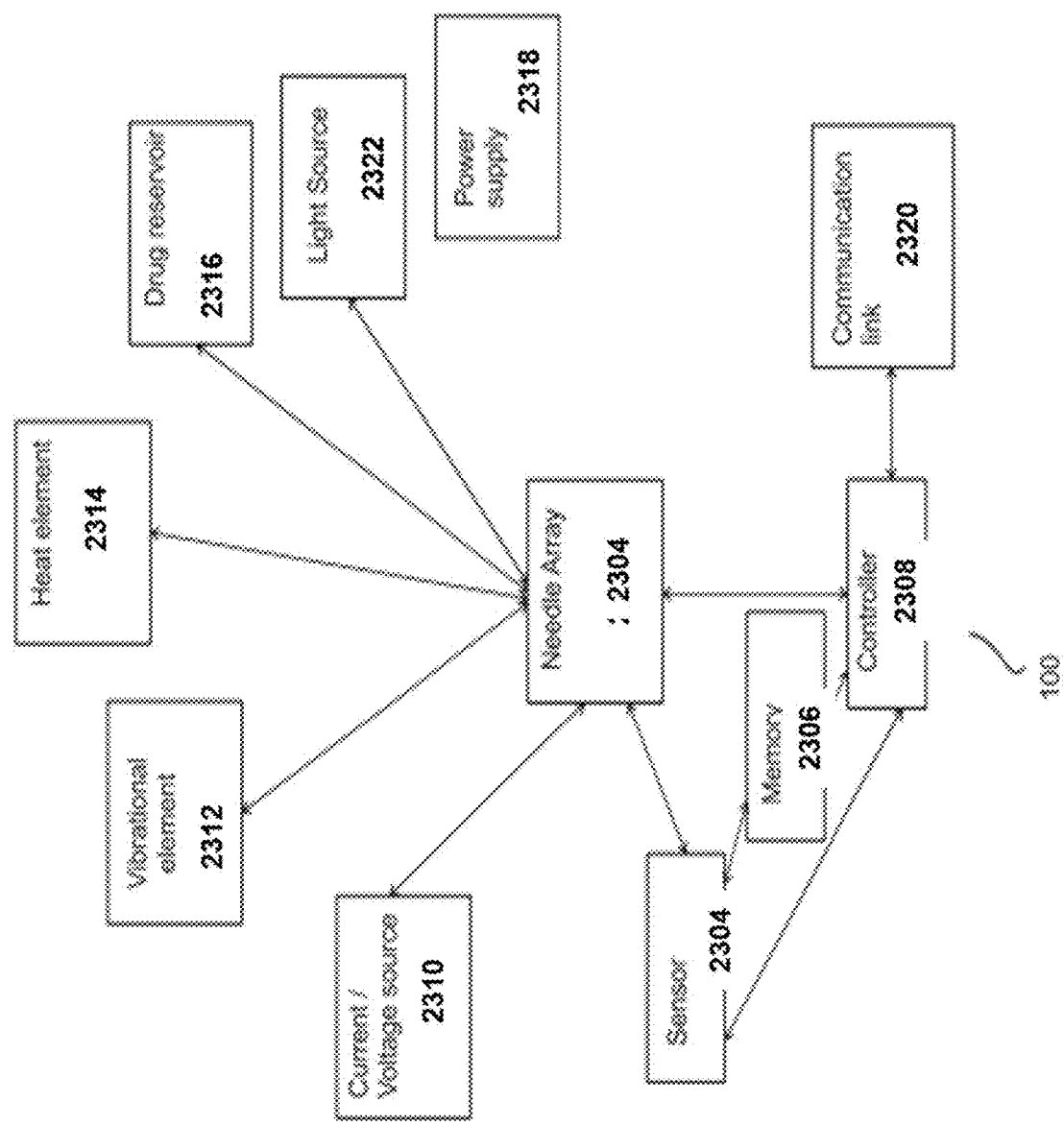

FIG. 36 is a general block diagram of the device, in accordance with an exemplary embodiment of the invention.

Figure 37:
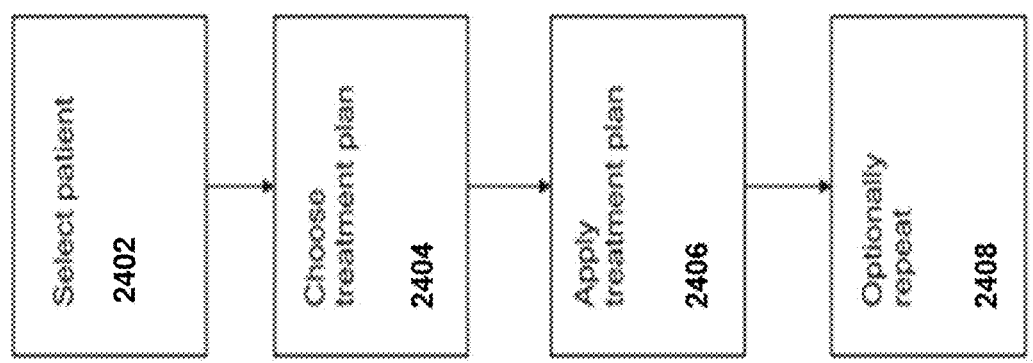

FIG. 37 is a flow chart of a method of stimulating hair growth, in accordance with an exemplary embodiment of the invention. FIG. 37 is a flowchart of an exemplary method of stimulating scalp hair growth, in accordance with an exemplary embodiment of the invention. Optionally, the method uses the hair stimulation device.

Optionally, at 2402, a patient is selected, in accordance with an exemplary embodiment of the invention. Optionally, the patient is male. Optionally or additionally, the patient has been diagnosed with androgenic alopecia. Optionally, the patient is at the early stages of hair loss (e.g., has not lost most of his hair).

Optionally, at 2404, the treatment plan is selected, in accordance with an exemplary embodiment of the invention. Optionally, a mechanical stimulation protocol is selected. Optionally or additionally, a vibration stimulation protocol is selected. Optionally or additionally, a thermal stimulation protocol is selected. Optionally or additionally, an ion deposition protocol is selected. Optionally or additionally, an electrical stimulation protocol is selected.

In some embodiments of the invention, at least some of the stimulation protocols (e.g., vibration, thermal, ion, electrical) are applied substantially simultaneously. Alternatively or additionally, at least some of the protocols are applied successively, for example, in no particular order. Alternatively or additionally, some protocols are selectively applied, while other protocols are not applied.

In some embodiments of the invention, the treatment plan is selected manually, for example by a physician, for example, based on personal experienced and/or clinical guidelines. Alternatively or additionally, the treatment plan is selected automatically, for example by software, for example, based on collected experimental data.

In some embodiments of the invention, the treatment plan is selected over a long period of time, for example, a single treatment session is to be repeated for a duration of time. For example, a single treatment plan is repeated four times a day, three times a day, twice a day, once a day, every other day, three days a week, twice a week, once a week, or other smaller, intermediate or larger time frames and/or repetition rates are used. For example, treatment is repeated over a month, over two months, over six months, over one year, over two years, indefinitely, or other smaller or intermediate time frames are used. Optionally, treatment is stopped when a desired growth effect is achieved and/or a certain time after, for example, a week or a month. Optionally or alternatively, stimulation is stopped, or at least paused for a week or more, if further progress is not seen. Optionally, the application and/or delay of treatment depends on scalp thickness, with treatment, for example, being continued as long as scalp thickness continues to increase and/or only if an increase is found.

In an exemplary embodiment of the invention, a maintenance level of treatment is defined and followed by the user. In some embodiments of the invention, the treatment plan is selected so that a different part of the scalp is treated during different treatments. For example, treatment may be twice a day with a different part of the scalp treated during each of the two daily treatments. Optionally, the areas of treatment during different treatment sessions partially overlap.

In some embodiments of the invention, the time per session is selected. For example, about 30 seconds, 1 minute, 2, 4, 6, 10 minutes, or other smaller, intermediate or larger times or subranges thereof are used. Optionally, the time is selected according to a pain level caused by the device and/or a user pain and/or comfort threshold.

In some embodiments of the invention, the treatment area is selected. For example, approximately 50% of the total area in need of treatment, 10%, 25%, 33%, 67%, 75%, 90%, 100% or other smaller, intermediate or larger areas or subranges thereof are used.

At 2406, the treatment plan and/or protocol is applied to the patient, in accordance with an exemplary embodiment of the invention. For example, the patient holds the device, and rolls the discs over the area of his scalp that requires stimulation. The needles on the discs prick his scalp according to the mechanical stimulation protocol. Optionally or additionally, the needles are vibrated according to the vibration protocol. Optionally or additionally, the skin is heated underneath the surface (e.g., heat transferred through the needles) according to the thermal stimulation protocol. Optionally or additionally, ions are deposited into below the skin (e.g., released from metallic coating on the needles) according to the ion deposition protocol. Optionally or additionally, electrical current and/or voltages are applied underneath the surface of the skin (e.g., using the needles as electrodes) according to the electrical stimulation protocol.

In a non-limiting example, a protocol comprises of treatments applied 3 times a week, for about 5 minutes per treatment. Each treatment comprises the following stimulations: 5 Volts, at 100 Hz AC, Zinc biased duty cycle, heating to a temperature of 60 degrees Celsius and vibration. Optionally, the protocol is selected according to trial and error, for example, the protocol is adjusted after a couple of weeks depending on the response of the scalp.

Optionally, at 2408, the treatment is repeated, for example, according to the plan as in 2404, in accordance with an exemplary embodiment of the invention. Optionally, the same treatment protocol is repeated. Alternatively, the treatment protocol is adjusted. For example, the initial treatment protocol is selected, the treatment is applied, and the treatment is adjusted based on feedback of success of the treatment.

Figure 38:
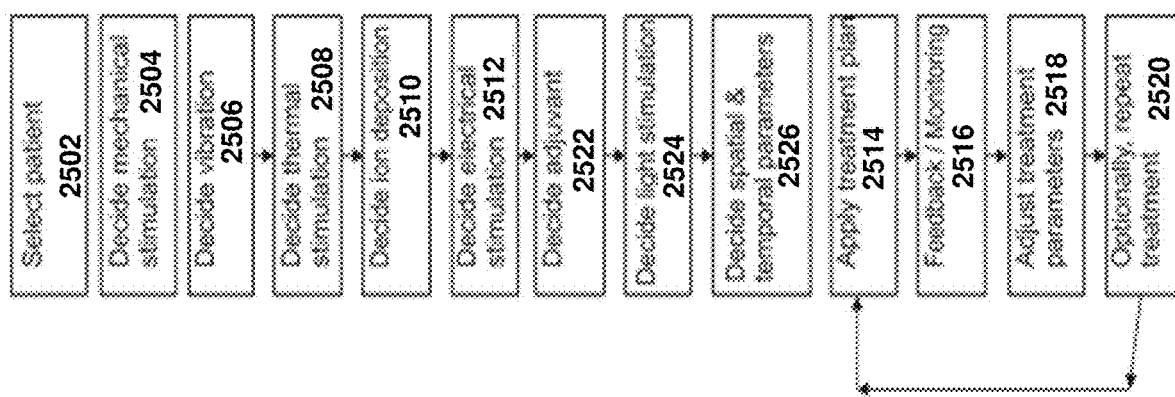
Figure 39:
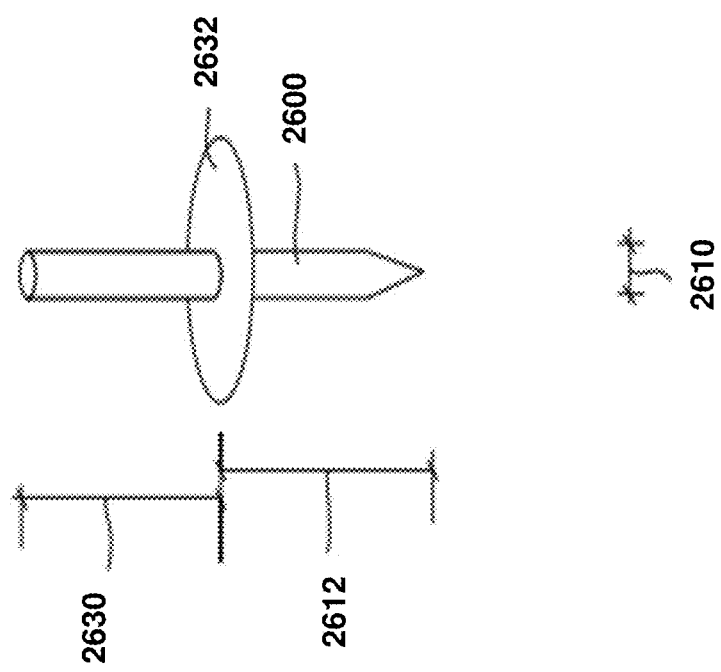

FIG. 38 is a flowchart of a detailed method of FIG. 37, in accordance with an exemplary embodiment of the invention;

Exemplary Method of Treatment

FIG. 38 is a detailed method of treatment of FIG. 37, in accordance with an exemplary embodiment of the invention. Optionally, at 2502, a patient is selected for treatment.
Optionally, at 2504, a decision is made with regards to the mechanical stimulation protocol.
Optionally, at 2506 a decision is made with regards to the vibration protocol.
Optionally, at 2508 a decision is made with regards to the thermal stimulation protocol.
Optionally, at 2510 a decision is made with regards to the ion application protocol.
Optionally, at 2512 a decision is made with regards to the electrical stimulation protocol.
Optionally, at 2522 a decision is made with regards to the use of adjuvant treatment.
Optionally, at 2524 a decision is made with regards to the use of light stimulation.
Optionally, at 2526 a decision is made with regards to the spatial and temporal parameters.
Optionally, at least one of the parameters chosen in steps 2504, 2506, 2508, 2510, 2512, 2522 and 2524 are specific per scalp area and are determined individually for each scalp area to be treated. For example, the temple area could receive one treatment and the vertex area could receive a different treatment. For example, it may be determined to treat the vertex area consecutively 5 minutes daily while the temples area is to be treated consecutively 4 minutes daily. At 2514, the treatment plan is applied.

Optionally, at 2516 feedback related to the treatment is obtained.

Optionally, at 2518 one or more variables of one or more treatment protocols are adjusted. Optionally, the adjustment is related to the feedback as in 2516.

Optionally, at 2520 treatment is repeated.

Per FIG. 22A, in an exemplary embodiment of the invention, needles, for example needles 2600, are selected and/or arranged as an array according to the selected mechanical stimulation protocol. Non-limiting examples include; a cross sectional diameter 2610 corresponding to the selected area of individual contacts and/or penetrations, a length 2612 corresponding to the selected depth of penetration (optionally, a stopper 2632, for example a flat disc, is used to set the needle length to prevent the needle from deeper penetration into the skin).

Figure 40:
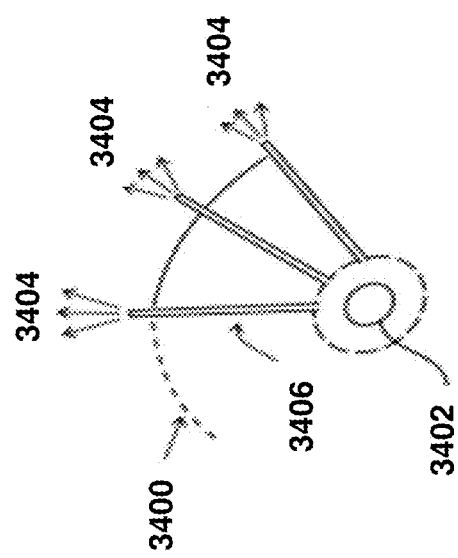
Figure 41:
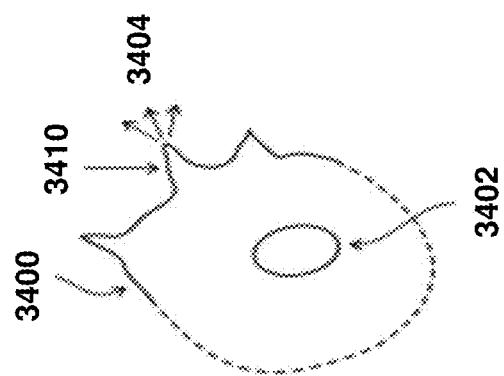

FIGS. 41 and 40 illustrate discs comprising a light source. In an exemplary embodiment, light conducting disc 3400 (FIG. 41) comprises light source 3402 causing light 3404 to emanate from spike 3410 on disc 3400. Optionally, disc 3400 comprises translucent material. Optionally or alternatively, spike 3410 comes to a sharp point. Optionally, spike 3410 is metallic.

FIG. 30B illustrates an exemplary embodiment in which light 3404 originates from light source 3402 and travels through optical fibers 3406 embedded in disc 3400. Optionally, the optical fibers 3406 penetrate directly into the skin. Optionally, optical fibers 3406 are thin enough to easily penetrate skin.

In some embodiments, one or more discs each comprise multiple fibers and/or needles. Optionally, at least one disc is for optical stimulation. Optionally or alternatively, at least one disc is metallic. Optionally or alternatively, at least one disc includes both optical needles and metallic needles. Optionally, at least one needle is both optical and metallic. Optionally or alternatively, fiber and/or needle are provided on parallel discs. Optionally or alternatively, fibers and/or needles are provided in a planar array.

Figure 42:
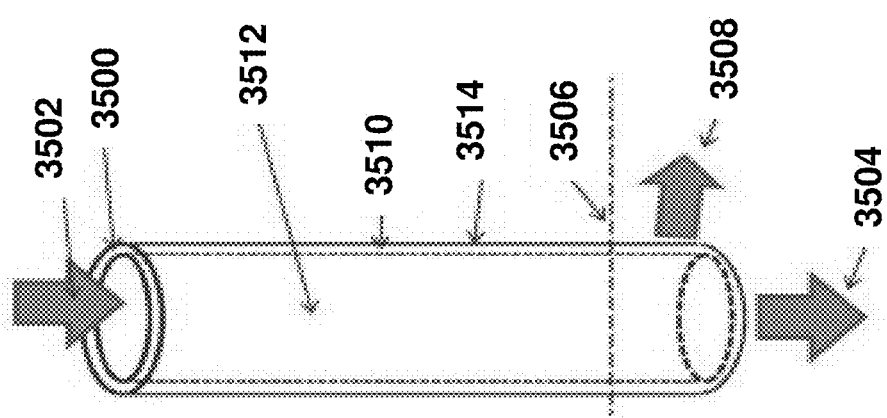

FIG. 42 illustrates an injector comprising a light guide, in accordance with an exemplary embodiment of the invention. In an exemplary embodiment, the light guide is an optical fiber coated with metal. For example, light is produced by light source 3502 which is powered by power source 3500 and emanates light 3504. Optionally, power source 3500 is electrical.

In some embodiments, power source 3500 emits ions 3508 directly into the scalp beneath the scalp surface 3506. Optionally, power source 3500 emits electricity directly into the scalp beneath the scalp surface 3506. Optionally, power source 3500 emits heat directly into the scalp beneath the scalp surface 3506. Optionally, the discs, needles and/or optical fibers also vibrate.

In some embodiments, the injector comprises a cavity 3512. Optionally, cavity 3512 comprises a light conducting core. For example, cavity 3512 may comprise light transmitting material. Optionally, the light transmitting material has structural rigidity. Optionally or alternatively, the light transmitting material has minimal structural rigidity.

In some embodiments, cavity 3512 comprises an internal optical fiber. For example, the internal optical fiber may comprise a metal coated thin optical fiber. Optionally or alternatively, the internal optical fiber may comprise an external shell conducting electricity. Optionally or alternatively, the internal optical fiber may comprise an external shell conducting heat. Optionally or alternatively, the internal optical fiber may comprise an external shell conducting injecting ions into the skin. Optionally or alternatively, the internal optical fiber may emit light into the skin.

In some embodiments, hollow cavity 3512 comprises a void which transmits light. Optionally, the outer portion 3510, inside outer layer 3512, of the injector comprises a source of vibration. Optionally or alternatively, the outer portion of the injector comprises a source of heat.

In some embodiments, the outer layer 3514 comprises an electrical conductor. For example, outer layer 3514 comprises metal. Optionally, outer layer 3514 is coated with ions to be deposited. For example, outer layer 3514 is coated with Cu. Alternatively, outer layer 3514 is coated with Zn. Optionally, outer layer 3514 comprises heat conducting material.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is expected that during the life of a patent maturing from this application many relevant hair stimulation devices will be developed and the scope of the term hair stimulation device is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A device for simultaneous stimulation of a scalp and direct ion-deposition into skin thereof, the device comprising:
   a. a wheel-array comprising a plurality of wheels that each have a thickness of at most 0.2 mm, the wheels of the wheel-array being parallel to each other and spaced apart from each other, at a spacing of at least 1 mm and at most 5 mm, along a common axis;
   b. an array of stimulating elements disposed along a respective circumference of each wheel of the wheel-array, each stimulating element comprising or being coated by a metal, each stimulating element being adapted to pierce said skin of said scalp no deeper than a thickness of a dermis; and
   c. an electrical power source, said stimulating elements coupled to the electrical power source, wherein the wheels of said wheel-array are adapted to roll over said scalp to drive said piercing by said stimulating elements such that:
      i. upon piercing contact between the stimulating elements and the skin and simultaneously therewith, the electrical power source causes the stimulating elements that are in said piercing contact with the skin to release ions of the metal directly into the skin of the scalp; and
      ii. the directly-released ions are supplied by the metal of the stimulating element or of the coating thereof so as to consume the stimulating element or the coating thereof.

2. The device of claim 1 wherein a type of ions delivered per stimulating element is controlled by controlling a polarity of voltage of each of the stimulating elements.

3. The device of claim 1, wherein,
   a first group of stimulating elements of said array comprises a first metal; and
   a second group of stimulating elements of said array comprises a second metal.

4. The device of claim 1, wherein said ions that are released upon said piercing of the skin comprise at least one of copper ions and zinc ions.

5. The device of claim 1 wherein the device is configured to operate according to operating parameters so that an efficiency of a deposition of the ions is enhanced through a dynamic modification of the operating parameters through closed-loop feedback/control.

6. The device of claim 1 wherein (i) the device comprises sensors incorporated in the device and (ii) the device is configured so that a number of ions deposited during treatment is controlled in a closed loop manner by setting an inter-stimulating-element voltage during the treatment based on feedback received from the sensors incorporated into the device.

7. The device of claim 1 configured to measure an impedance of the scalp and to compare a current impedance with a previously measured impedance.

8. The device of claim 1 wherein the device further comprises an encoder operable to count revolutions or partial revolutions of the wheel-array.

9. The device of claim 1, further comprising at least one element to vibrate at least one of the stimulating elements.

10. The device of claim 1 wherein the electrical power source is an alternating current source that is adapted to operate at a frequency of at most about 500 Hz.

11. The device of claim 1 wherein the electrical power source is an alternating current source that is adapted to operate at a frequency of at most about 100 Hz.

12. The device of claim 1 wherein the stimulating elements are shaped so as to form a wound in the skin having a cross sectional area of at most 0.01 mm$^2$ upon said piercing of the skin to directly release the ions therein.

13. A method comprising:
  a. providing the device of claim 1;
  b. rotating the wheels of the wheel-array to roll the wheels over said scalp to drive said piercing by said stimulating elements such that:
    i. upon piercing of the skin and simultaneously therewith, the electrical power source causes the stimulating elements to release ions of the metal directly into the skin of the scalp; and
    ii. the directly-released ions are supplied by the metal of the stimulating element or of the coating thereof so as to consume the stimulating element or the coating thereof.

14. The method of claim 13 wherein each piercing is of a duration of not less than 0.01 seconds and not more than 0.1 seconds.

\* \* \* \* \*